(12) United States Patent
Spencer et al.

(10) Patent No.: US 10,420,824 B2
(45) Date of Patent: *Sep. 24, 2019

(54) INDUCED ACTIVATION IN DENDRITIC CELLS

(71) Applicant: BAYLOR COLLEGE OF MEDICINE, Houston, TX (US)

(72) Inventors: David Spencer, Houston, TX (US); Brent Hanks, Durham, NC (US); Kevin Slawin, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/399,512

(22) Filed: Jan. 5, 2017

(65) Prior Publication Data

US 2017/0182140 A1  Jun. 29, 2017

Related U.S. Application Data

(63) Continuation of application No. 14/643,989, filed on Mar. 10, 2015, now Pat. No. 9,572,835, which is a continuation of application No. 13/786,339, filed on Mar. 5, 2013, now Pat. No. 8,999,949, which is a continuation of application No. 12/165,360, filed on Jun. 30, 2008, now Pat. No. 8,771,671, which is a continuation of application No. 10/781,384, filed on Feb. 18, 2004, now Pat. No. 7,404,950.

(60) Provisional application No. 60/448,046, filed on Feb. 18, 2003.

(51) Int. Cl.
| | | |
|---|---|---|
| A61K 35/15 | (2015.01) | |
| A61K 38/00 | (2006.01) | |
| A61K 39/00 | (2006.01) | |
| A61K 39/02 | (2006.01) | |
| A61K 38/17 | (2006.01) | |
| A61K 39/12 | (2006.01) | |
| C12N 5/10 | (2006.01) | |
| C07K 14/705 | (2006.01) | |
| C12N 9/48 | (2006.01) | |
| C12N 9/90 | (2006.01) | |
| C12N 5/16 | (2006.01) | |

(52) U.S. Cl.
CPC .............. *A61K 39/02* (2013.01); *A61K 35/15* (2013.01); *A61K 38/177* (2013.01); *A61K 39/0011* (2013.01); *A61K 39/12* (2013.01); *C07K 14/70578* (2013.01); *C12N 5/10* (2013.01); *C12N 9/485* (2013.01); *C12N 9/90* (2013.01); *C12Y 502/01008* (2013.01); *A61K 38/1774* (2013.01); *A61K 2039/5154* (2013.01); *A61K 2039/5156* (2013.01); *A61K 2039/53* (2013.01); *A61K 2039/55516* (2013.01); *C07K 2319/033* (2013.01); *C12N 5/16* (2013.01); *C12N 2710/10043* (2013.01); *C12Y 304/17021* (2013.01); *C12Y 502/01* (2013.01)

(58) Field of Classification Search
CPC .... A61K 35/15; A61K 38/00; A61K 38/1774; A61K 39/00; A61K 2039/5154; A61K 2039/5156; C12N 2710/10043
See application file for complete search history.

(56) References Cited

U.S. PATENT DOCUMENTS

| | | |
|---|---|---|
| 4,514,506 A | 4/1985 | Braatz et al. |
| 5,384,253 A | 1/1995 | Krzyek |
| 5,538,880 A | 7/1996 | Lundquist et al. |
| 5,550,214 A | 8/1996 | Eberlein et al. |
| 5,550,318 A | 8/1996 | Adams et al. |
| 5,589,343 A | 12/1996 | Marchand et al. |
| 5,610,042 A | 3/1997 | Chang et al. |
| 5,645,992 A | 7/1997 | Lott et al. |
| 5,648,226 A | 7/1997 | Van Den Eynde et al. |
| 5,709,995 A | 1/1998 | Chisari et al. |
| 5,719,054 A | 2/1998 | Boursnell et al. |
| 5,741,899 A | 4/1998 | Capon et al. |
| 5,750,395 A | 5/1998 | Fikes et al. |
| 5,780,036 A | 7/1998 | Chisari |
| 5,830,462 A | 11/1998 | Crabtree et al. |
| 5,834,266 A | 11/1998 | Crabtree et al. |
| 5,840,839 A | 11/1998 | Wang et al. |
| 5,869,337 A | 2/1999 | Crabtree et al. |
| 5,869,608 A | 2/1999 | Caldwell et al. |
| 5,871,753 A | 2/1999 | Crabtree et al. |
| 5,925,565 A | 7/1999 | Berlioz et al. |
| 5,935,819 A | 8/1999 | Eichner et al. |
| 5,955,596 A | 9/1999 | Zagursky et al. |
| 5,965,242 A | 10/1999 | Patton et al. |
| 5,994,313 A | 11/1999 | Crabtree et al. |
| 5,995,596 A | 11/1999 | Shaffer et al. |
| 6,011,018 A | 1/2000 | Crabtree et al. |
| 6,043,082 A | 3/2000 | Crabtree et al. |
| 6,046,047 A | 4/2000 | Crabtree et al. |
| 6,046,158 A | 4/2000 | Ariizumi et al. |
| 6,054,436 A | 4/2000 | Crabtree et al. |

(Continued)

FOREIGN PATENT DOCUMENTS

| | | |
|---|---|---|
| EP | 0 273 085 | 7/1984 |
| EP | 0 510 691 | 10/1992 |

(Continued)

OTHER PUBLICATIONS

Office Action dated Sep. 29, 2017 in U.S. Appl. No. 14/191,167, filed Feb. 26, 2014 and Published as 2014-0287490 on Sep. 25, 2014.

(Continued)

*Primary Examiner* — Kevin K Hill
(74) *Attorney, Agent, or Firm* — Jones Day

(57) ABSTRACT

The present invention is directed to a composition and method which to treat diseases and to enhance a regulated immune response. More particularly, the present invention is drawn to compositions that are based on dendritic cells modified to express an inducible form of a co-stimulatory polypeptide.

16 Claims, 20 Drawing Sheets

Specification includes a Sequence Listing.

(56) References Cited

U.S. PATENT DOCUMENTS

| | | | |
|---|---|---|---|
| 6,497,876 | B1 | 12/2002 | Maraskovsky et al. |
| 6,558,951 | B1 | 5/2003 | Tomai et al. |
| 6,670,186 | B1 | 12/2003 | Nair et al. |
| 6,943,245 | B2 | 9/2005 | Killary et al. |
| 7,404,950 | B2 | 7/2008 | Spencer |
| 8,486,693 | B2 | 7/2013 | Park et al. |
| 8,691,210 | B2 | 4/2014 | Lapteva et al. |
| 8,771,671 | B2 | 7/2014 | Spencer |
| 8,999,949 | B2 | 4/2015 | Spencer et al. |
| 9,428,569 | B2 | 8/2016 | Spencer |
| 9,572,835 | B2 * | 2/2017 | Spencer ............... A61K 38/177 |
| 2003/0082163 | A1 | 5/2003 | Shu |
| 2003/0091593 | A1 | 5/2003 | Bachmann et al. |
| 2003/0092132 | A1 | 5/2003 | Rodgers |
| 2003/0108527 | A1 | 6/2003 | Seya et al. |
| 2003/0153518 | A1 | 8/2003 | Foxwell et al. |
| 2003/0206917 | A1 | 11/2003 | Tykocinski et al. |
| 2003/0232055 | A1 | 12/2003 | Medzhitov |
| 2004/0019195 | A1 | 1/2004 | Scholm et al. |
| 2004/0040047 | A1 | 2/2004 | Spencer |
| 2004/0209836 | A1 | 10/2004 | Spencer |
| 2005/0181366 | A1 | 8/2005 | Ostermeier |
| 2005/0215472 | A1 | 9/2005 | Schulke et al. |
| 2007/0081963 | A1 | 4/2007 | Oh et al. |
| 2008/0269160 | A1 | 10/2008 | Spencer et al. |
| 2008/0274140 | A1 | 11/2008 | Weiner et al. |
| 2009/0175880 | A1 | 7/2009 | Keler et al. |
| 2009/0311183 | A1 | 12/2009 | Devy et al. |
| 2010/0196336 | A1 | 8/2010 | Park et al. |
| 2010/0203067 | A1 | 8/2010 | Spencer et al. |
| 2011/0033383 | A1 | 2/2011 | Spencer et al. |
| 2011/0034752 | A1 | 2/2011 | Kessler |
| 2011/0171221 | A1 | 7/2011 | Vieweg |
| 2011/0287038 | A1 | 11/2011 | Slawin et al. |
| 2013/0131315 | A1 | 5/2013 | Su |
| 2013/0183333 | A1 | 7/2013 | Spencer et al. |
| 2013/0287748 | A1 | 10/2013 | June |
| 2013/0295110 | A1 | 11/2013 | Binder |
| 2014/0023647 | A1 | 1/2014 | Slawin et al. |
| 2014/0087468 | A1 | 3/2014 | Spencer et al. |
| 2014/0120622 | A1 | 5/2014 | Gregory |
| 2014/0287490 | A1 | 9/2014 | Spencer et al. |
| 2015/0111294 | A1 | 4/2015 | Spencer et al. |
| 2015/0306140 | A1 | 10/2015 | Spencer et al. |
| 2017/0002321 | A1 | 1/2017 | Spencer et al. |
| 2018/0201663 | A1 | 7/2018 | Spencer et al. |

FOREIGN PATENT DOCUMENTS

| | | |
|---|---|---|
| WO | WO 94/009699 | 5/1994 |
| WO | WO 94/018317 | 8/1994 |
| WO | WO 96/012796 | 5/1996 |
| WO | WO 01/083551 | 11/2001 |
| WO | WO 02/036769 | 5/2002 |
| WO | WO 08/049113 | 4/2004 |
| WO | WO 04/073641 | 9/2004 |
| WO | WO 10/033949 | 3/2006 |
| WO | WO 11/130566 | 12/2007 |
| WO | WO 09/061996 | 5/2009 |
| WO | WO 14/151960 | 9/2014 |

OTHER PUBLICATIONS

Office Action dated Sep. 25, 2017 in U.S. Appl. No. 15/216,008, filed Jul. 21, 2016 and Published as US 2017-0002321 on Jan. 5, 2017.
Office Action dated Jan. 25, 2018 in U.S. Appl. No. 15/216,008, filed Jul. 21, 2016 and Published as US 2017-0002321 on Jan. 5, 2017.
Office Action dated Aug. 7, 2017 in U.S. Appl. No. 14/622,018, filed Feb. 13, 2015 and published as US 2016-0046700 on Feb. 18, 2016.
Office Action dated Feb. 1, 2018 in U.S. Appl. No. 14/622,018, filed Feb. 13, 2015 and published as US 2016-0046700 on Feb. 18, 2016.
Bonnert et al., "The cloning and characterization of human MyD88: a member of an IL-1 receptor related family" FEBS Lett (1997) 402:81-84.
Ahonen et al., "Combined TLR and CD40 triggering induces potent CD8+ T cell expansion with variable dependence on type I IFN" J. Exp. Med. (2004) 199(6):775-784.
Burns et al., "MyD88, an adapter protein involved in interleukin-1 signaling" J. Biol. Chem. (1998) 273(20):12203-12209.
Feinstein et al., "The death domain: a module shared by proteins with diverse cellular functions" Trends Biochem. Sci. (1995) 20(9):342-344.
Hacker et al., "Specificity in Toll-like receptor signalling through distinct effector functions of TRAF3 and TRAF6" Nature (2006) 439:204-207.
Office Action dated May 8, 2017 in U.S. Appl. No. 14/191,167, filed Feb. 26, 2014 and Published as 2014-0287490 on Sep. 25, 2014.
Office Action dated May 8, 2017 in U.S. Appl. No. 15/216,008, filed Jul. 21, 2016 and Published as US 2017-0002321 on Jan. 5, 2017.
Geng et al., "Amplifying TLR-MyD88 signals within tumor-specific T cells enhances antitumor activity to suboptimal levels of weakly immunogenic tumor antigens" Cancer Research (2010) 70(19):7442-7454.
Extended European Search Report dated Jul. 28, 2017 in European Patent Application No. 17169050.6, filed on Sep. 21, 2009.
"Sipuleucel-T:APC 8015, APC-8015, prostate cancer vaccine—Dendreon." Drugs R D. 2006;7(3):197-201.
Adam et al., "Cross-linking of The p55 Tumor Necrosis Factor Receptor Cytoplasmic Domain by a Dimeric Ligand Induces nuclear Factor-kB and Mediates Cell Death," the Journal of Biological Chemistry vol. 270, No. 29, Jul. 21, 1995, pp. 17482-17487.
Adema et al., "A dendritic-cell-deprived C-C chemokine that preferentially attracts naïve T cells." Nature. Jun. 12, 1997;387(6634):713-717.
Adema et al., "Migration of dendritic cell based cancer vaccines: in vivo veritas?" Curr Opin Immunol. Apr. 2005;17(2):170-174.
Albert et al., "Dendritic cell maturation is required for the cross-tolerization of CD8+ T cells." Nat Immunol. Nov. 2001;2(11):1010-1017.
Aliprantis et al., "The apoptotic signaling pathway activated by Toll-like receptor-2," EMBO J. 19(13):3325-3336, (2000).
Amara et al, "A versatile synthetic dimerizer for the regulation of protein-protein interactions." PNAS 1997;94:10618-10623.
Amara et al., "Cell surface tagging and a suicide mechanism in a single chimeric human protein" Hum. Gene Ther. (1999) 10(16):2651-5.
Anderson et al., "A homologue of the TNF receptor and its ligand enhance T-cell growth and dendritic-cell function." Nature. Nov. 13, 1997;390(6656):175-179.
Arcone et al., "Identification of sequences responsible for acute-phase induction of human C-reactive protein." Nucleic Acids Res. Apr. 25, 1988;16(8):3195-3207.
Ardeshna et al., "The P13 kinase, p38 SAP kinase, and NF-kappaB signal transduction pathways are involved in the survival and maturation of lipopolysaccharide-stimulated human monocyte-derived dendritic cells." Blood. Aug. 1, 2000;96(3):1039-1046.
Banchereau et al., "Dendritic cells and the control of immunity." Nature. Mar. 19, 1998;392(6673):245-252.
Banchereau et al., "Dendritic cells as therapeutic vaccines against cancer." Nat Rev Immunol. Apr. 2005;5(4):296-306.
Banchereau et al., "Dendritic cells: controllers of the immune system and a new promise for immunotherapy." Ann NY Acad Sci. Apr. 2003;987:180-187.
Banchereau et al., "Immunobiology of dendritic cells." Annu Rev Immunol. 2000; 18:767-811.
Bander et al., "Phase I trial of 177lutetium-labeled J591, a monoclonal antibody to prostate-specific membrane antigen, in patients with androgen-independent prostate cancer." J Clin Oncol. Jul. 20, 2005;23(21):4591-601.
Belshaw et al. (Sep. 1996). "Controlling programmed cell death with a cyclophilin-cyclosporin-based chemical inducer of dimerization." Chemistry & Biology. 3(9): pp. 731-738.

(56) References Cited

OTHER PUBLICATIONS

Bennett et al., "Apoptosis of rat vascular smooth muscle cells is regulated by p53-dependent and -independent pathways." Circ Res. Aug. 1995;77(2):266-273.
Bennett et al., "Help for cytotoxic-T-cell response is mediated by CD40 signalling." Nature. Jun. 4, 1998;393(6684):478-480.
Bernard et al., "HIV-specific cytotoxic T-lymphocyte activity in immunologically normal HIV-infected persons." AIDS. Nov. 12, 1998;12(16):2125-2139.
Beutler B., "Inferences, questions and possibilities in Toll-like receptor signalling." Nature. Jul. 8, 2004;430(6996):257-263.
Bianco FJ, et al., "Natural History of Biochemically-Recurrent Castrate-Resistant Disease in Men treated with maximal androgen blockage for a Rising PSA after Radical Prostatectomy," Cancer Symposium: Abstract 278, 2005.
Bisping et al., "Targeting receptor kinases by a novel indolinone derivative in multiple myeloma: abrogation of stroma-derived interleukin-6 secretion and induction of apoptosis in cytogenetically defined subgroups." Blood. Mar. 1, 2006;107(5):2079-2089.
Blau et al., "A proliferation switch for genetically modified cells." Proc Natl Acad Sci USA. Apr. 1, 1997;94(7):3076-3081.
Bojak et al., "Muscle specific versus ubiquitous expression of Gag based HIV-1 DNA vaccines: a comparative analysis." Vaccine. May 6, 2002;20(15):1975-1979.
Boldin et al., "Involvement of Mach, a Novel MORT1/FADD-Interacting Protease, in FAS/APO-1- and TNF Receptor—Induced Cell Death," Cell vol. 85, 803-815, Jun. 14, 1996.
Bollard et al., "Adapting a transforming growth factor beta-related tumor protection strategy to enhance antitumor immunity" Blood (2002) 99:3179-3187.
Bonnert et al., GeneBank: AAC50954.1; GI: 1814020; Feb. 2, 1997.
Bonnert et al., GenBank Accession No. U84408, 1997.
Bowie et al, "Deciphering the message in protein sequences: tolerance to amino acid substitutions." Science Mar. 1990; 247:1306-1310.
Burns et al., Inhibition of Interleukin 1 Receptor/Toll-like Receptor Signaling through the Alternatively Spliced, Short Form of MyD88 Is Due to Its Failure to Recruit IRAK-4, J. Exp. Med 197(2):263-268, Jan. 20, 2003.
Carter et al., "Prostate-specific membrane antigen is a hydrolase with substrate and pharmacologic characteristics of a neuropeptidase." Proc Natl Acad Sci U S A. Jan. 23, 1996;93(2):749-53.
Caux et al., "Activation of human dendritic cells through CD40 cross-linking" J. Exp. Med. (1994) 180:1263-72.
Caux et al., "CD34+ hematopoietic progenitors from human cord blood differentiate along two independent dendritic cell pathways in response to GM–CSF+TNF alpha." Adv Exp Med Biol. 1997;417:21-25.
Caux et al., "In vitro regulation of development and function of dendritic cells." Hematol Cell Ther. Oct. 1996;38(5):463.
Cazeaux et al., "Comparative study of immune responses induced after immunization with plasmids encoding the HIV-1 Nef protein under the control of the CMV-IE or the muscle-specific desmin promoter." Vaccine. Sep. 10, 2002;20(27-28):3322-31.
Chan et al., "A Domain in TNF Receptors that mediates ligand-independent receptor assembly and signaling," Science 288, 2351-2354, (2001).
Chan, Francis Ka-Ming, "Three is Better Than One: Pre-Ligand Receptor Assembly in the Regulation of TNF Receptor Signaling," Cytokine, Feb. 2007; 37(2) 101-107.
Chang et al., "Metastatic renal cell carcinoma neovasculature expresses prostate-specific membrane antigen." Urology. Apr. 2001;57(4):801-5.
Chang et al., "Prostate-specific membrane antigen is produced in tumor-associated neovasculature." Clin Cancer Res. Oct. 1999;5(10):2674-81.
Chatterjee et al., "Strategies for efficient gene transfer into hematopoietic cells. The use of adeno-associated virus vectors in gene therapy." Ann Ny Acad Sci. Dec. 29, 1995;770:7990.
Chen C, Okayama H., "High-efficiency transformation of mammalian cells by plasmid DNA." Mol Cell Biol. Aug. 1987;7(8):2745-2752.
Chen et al., "A testicular antigen aberrantly expressed in human cancers detected by autologous antibody screening." Proc Natl Acad Sci USA. Mar. 4, 1997;94(5):1914-1918.
Cheung et al., "Plasmid encoding papillomavirus Type 16 (HPV16) DNA construced with codon optimization improved the immunogenicity against HPV infection." Vaccine. Dec. 16, 2004;23(5):629-638.
Chiodoni et ai, "Dendritic Cells Infiltrating Tumors Cotransduced with Granulocyte/Macrophage Colony-Stimulating factor (GM-CSF) and CD40 Ligand Genes Take Up and Present Endo-genous Tumor-Associated Antigens, and Prime Naive Mice for a Cytotoxic T Lymphocyte Response," J. Exp. Med. vol. 190, No. 1, Jul. 5, 1999. pp. 125-133.
Choe et al., "Crystal structure of human toll-like receptor 3 (TLR3) ectodomain." Science. Jul. 22, 2005;309(5734):581-585.
Christiansen et al., "N-glycosylation and microtubule integrity are involved in apical targeting of prostate-specific membrane antigen: implications for immunotherapy." Mol Cancer Ther. May 2005;4(5):704-14.
Cisco et al., "Induction of human dendritic cell maturation using transfection with RNA encoding a dominant positive toll-like receptor 4." J Immunol. Jun. 1, 2004;172(11):7162-7168.
Clackson et al., "Redesigning an FKBP-ligand interface to generate chemical dimerizers with novel specificity." Proc Natl Acad Sci USA. Sep. 1, 1998;95(18):10437-10442.
Clackson T., "Dissecting the functions of proteins and pathways using chemically induced dimerization." Chem Biol Drug Des. Jun. 2006;67(6):440-442.
Clarke et al., "Randomized phase II trial of chemoradiotherapy followed by either dose-dense or metronomic temozolomide for newly diagnosed glioblastoma." J Clin Oncol. Aug. 10, 2009;27(23):3861-7.
Clarke SR., "The critical role of CD40/CD40L in the CD4-dependent generation of CD8+ T cell immunity." J Leukoc Biol. May 2000;67(5):607-614.
Clarke, S.J., et al., "A phase I, pharmacokinetic (PK), and preliminary efficacy assessment of ALD518, a humanized anti-IL-6 antibody, in patients with advanced cancer ," 2009, J. Clin. Oncol. 27:15s (suppl.; abstr. 3025).
Coffin "Molecular Mechanisms of Nucleic Acid Integration," Journal of Mecical Virology, 31:43-19 (1990).
Cohen et al., "Nucleotide sequence of the cDNA encoding human tyrosinase-related protein." Nucleic Acids Res. May 11, 1990;18(9):2807-2808.
Contin et al., "Membrane-anchored CD40 is processed by the tumor necrosis factor-alpha-converting enzyme. Implications for CD40 signaling." J Biol Chem. Aug. 29, 2003;278(35):32801-32809.
Coupar et al., "A general methods for the construction of recombinant vaccinia viruses expressing multiple foreign genes." Gene. Aug. 15, 1988;68(1):1-10.
Cranmer et al., "Clinical applications of dendritic cell vaccination in the treatment of cancer." Cancer Immunol Immunother. Apr. 2004;54(4):275-306.
Crawford et al., "A controlled trial of leuprolide with and without flutamide in prostatic carcinoma." N Engl J Med. Aug. 17, 1989;321(7):419-424, w/, erratum N Engl J Med Nov. 16, 1989;321(20):1420.
Cremer et al., "Long-lived immature dendritic cells mediated by Trance-Rank interaction." Blood. Nov. 15, 2002;100(10):3646-3655.
Cristofanilli et al., "Circulating tumor cells, disease progression, and survival in metastatic breast cancer." N Engl J Med. Aug. 19, 2004;351(8):781-91.
Cyster JG., "Chemokines and cell migration in secondary lymphoid organs." Science. Dec. 10, 1999;286(5447):2098-2102.
Dallal RM, Lotze MT., "The dendritic cell and human cancer vaccines." Curr Opin Immunol. Oct. 2000;12(5):583-588.
Davis et al., "Crystal structure of prostate-specific membrane antigen, a tumor marker and peptidase." Proc Natl Acad Sci USA. Apr. 26, 2005;102(17):5981-5986.

(56) References Cited

OTHER PUBLICATIONS

De Becker et al., "The adjuvant monophosphoryl lipid a increases the function of antigen-presenting cells." Int Immunol. Jun. 2000;12(6):807-815.
De Gruijl et al, "Prolonged Maturation and Enhanced Transduction of Dendritic Cells Migrated from Human Skin Explants After In Situ Delivery of CD40-Targeted Adenoviral Vectors," The Journal of Immunology vol. 169,2002 PQS 5322-5331.
De la Thille et al., "Detection of prostate-specific membrane antigen expressing cells in blood obtained from renal cancer patients: a potential biomarker of vascular invasion." Cancer Detect Prev. 2000;24(6):579-88.
De Vries et al., "Effective migration of antigen-pulsed dendritic cells to lymph nodes in melanoma patients is determined by their maturation state." Cancer Res. Jan. 1, 2003;63(1):12-17.
Deml et al. "Multiple effects of codon usage optimization on expression and immunogenicity of DNA candidate vaccines encoding the human immunodeficiency virus type 1 Gag protein," 2001. J. Virol. 75:10991-11001.
Deonarain, "Ligand-targeted receptor-mediated vectors for gene delivery," 1998, Expert Opin. Ther. Pat., vol. 8, pp. 53-69.
Diehl et al., "CD40 activation in vivo overcomes peptide-induced peripheral cytotoxic T-lymphocyte tolerance and augments antitumor vaccine efficacy." Nat Med. Jul. 1999;5(7):774-779.
Donnelly et al., "DNA vaccines." Annu Rev Immunol. 1997;15:617-48.
Dudley et al., "Adoptive cell transfer therapy following non-myeloablative but lymphodepleting chemotherapy for the treatment of patients with refractory metastic melanoma." J Clin Oncol. Apr. 1, 2005;23(10):2346-2357.
Elgueta et al., "Molecular mechanism and function of CD40/CD40L engagement in the immune system," Immunological Reviews, 229, (2009) 152-172.
Evel-Kabler et al., "SOCS1 restricts dendritic cells' ability to break self tolerance and induce antitumor immunity by regulating IL-12 production and signaling." J Clin Invest. Jan. 2006;116(1):90-100.
Fan et al., "Improved artificial death switches based on caspases and FADD." Hum Gene Ther. Sep. 20, 1999;10(14):2273-2285.
Farrar et al., "Activation of the Raf-1 kinase cascade by coumermycin-induced dimerization," Nature, Sep. 12, 1996;383(6596):178-181.
Fearon et al., "The instructive role of innate immunity in the acquired immune response," Science, Apr. 5, 1996;272(5258):50-53.
Fechheimer et al., "Transfection of mammalian cells with plasmid DNA by scrape loading and sonication loading." Proc Natl Acad Sci USA. Dec. 1987;84(23):8463-8467.
Fernandez et al., "Dendritic cells directly trigger NK cell functions: cross-talk relevant in innate anti-tumor immune responses in vivo." Nat Med. Apr. 1999;5(4):405-411.
Ferrari et al., "Second-strand synthesis is a rate-limiting step for efficient transduction by recombinant adeno-associated virus vectors." J Virol. May 1996;70(5):3227-3234.
Ferraro et al., "Co-delivery of PSA and PSMA DNA vaccines with electroporation induces potent immune responses" Human Vaccines (2011) 7:120-127.
Fisher et al., "Transduction with recombinant adeno-associated virus for gene therapy is limited by leading-strand synthesis." J Virol. Jan. 1996;70(1):520-532.
Flotte et al., "Stable in vivo expression of the cystic fibrosis transmembrane conductance regulator with an adeno-associated virus vector." Proc Natl Acad Sci USA. Nov. 15, 1993;90(22):10613-10617.
Flotte TR, Carter BJ. "Adeno-associated virus vectors for gene therapy." Gene Ther. Aug. 1995;2(6):357-362.
Flotte, "Prospects for Virus-Based Gene Therapy for Cystic Fibrosis," Journal of Bioenergetics and Bioinformatics, vol. 25, No. 1, 1993.
Freeman et al., "The role of (111)in Capromab Pendetide (Prosta-ScintR) immunoscintigraphy in the management of prostate cancer." Q J Nucl Med. Jun. 2002;46(2):131-7.
Fujio Y, Walsh K., "Akt mediates cytoprotection of endothelial cells by vascular endothelial growth factor in an anchorage-dependent manner." J Biol Chem. Jun. 4, 1999;274(23):16349-16354.
Galbiati et al., "N-terminal fatty acylation of the alpha-subunit of the G-protein Gi1: only the myristoylated protein is a substrate for palmitoylation." Biochem J. Nov. 1, 1994;303(Pt 3):697-700.
Gauthier-Campbell et al., "Regulation of dendritic branching and pilopodia formation in hippocampal neurons by specific acylated protein motifs." Mol Biol Cell. May 2004;15(5):2205-2217.
Gay et al., "Assembly and localization of Toll-like receptor signaling complexes", Nature Reviews Immunology (2014) 14:546-558.
Gefter et al., "A simple method for polyethylene glycol-promoted hybridization of mouse myeloma cells." Somatic Cell Genet. Mar. 1977;3(2):231-236.
GenBank Accession No. M29540,Human carcinoembryonic antigen mRNA (CEA), complete cds, Nov. 1, 1994.
Gestwicki JE, Marinec PS., Chemical control over protein-protein interactions: beyond inhibitors. Comb Chem High Throughput Screen. Sep. 2007;10(8):667-675.
Gilboa E, Vieweg J., "Cancer immunotherapy with mRNA-transfected dendritic cells." Immunol Rev. Jun. 2004;199:251-263.
Gilboa E., "The promise of cancer vaccines." Nat Rev Cancer. May 2004;4(5):401-411.
Gittes RF., "Carcinoma of the prostate." N Engl J Med. Jan. 24, 1991;324(4):236-245.
Glode, "The case for adjuvant therapy for prostate cancer" Journal of Urology (2006) 176:S30-S33.
Goodman et al., "Recombinant adeno-associated virus-mediated gene transfer into hematopoietic progenitor cells." Blood. Sep. 1, 1994;84(5):1492-1500.
Goodwin et al., "Suppression of human T-cell mitogenesis by prostaglandin. Existence of a prostaglandin-producing suppressor cell." J Exp Med. Dec. 1, 1977;146(6):1719-1734.
Goodwin JS., "Immunomodulation by eicosanoids and anti-anflammatory drugs." Curr Opin Immunol. Dec. 1989;2(2):264-268.
Gopal TV., "Gene transfer method for transient gene expression, stable transformation, and cotransformation of suspension cell cultures." Mol Cell Biol. May 1985;5(5):1188-1190.
Gossen et al., "Transcriptional activation by tetracyclines in mammalian cells." Science. Jun. 23, 1995;268(5218):1766-1769.
Gossen M, Bujard H., "Tight control of gene expression in mammalian cells by tetracycline-responsive promoters." Proc Natil Acad Sci USA. Jun. 15, 1992;89(12):5547-5551.
Graham FL, van der Eb AJ., "A new technique for the assay of infectivity of human adenovirus 5 DNA." Virology. Apr. 1973;52(2):456-467.
Granucci et al., "Eerly events in dendritic cell maturation induced by LPS." Microbes Infect. Nov. 1999;1(13):1079-1084.
Granucci et al., "Inducible IL-2 production by dendritic cells revealed by global gene expression analysis." Nat Immunol. Sep. 2001;2(9):882-888.
Granucci et al., "Modulation of cytokine expression in mouse dendritic cell clones." Eur J Immunol. Oct. 1994;24(10):2522-2526.
Grewal IS, Flavell RA., "CD40 and CD154 in cell-mediated immunity." Annu Rev Immunol. 1998;16:111-135.
Hammad et al., "Monocyte-derived dendritic cells induce a house dust mite-specific Th2 allergic inflammation in the lung of humanized SCID mice:involvement of CCR7." J Immunol. Aug. 1, 2002;169(3):1524-1534.
Hanks B.A., et al., "Re-engineered CD40 receptor enables potent pharmacological activation of dendritic-cell cancer vaccines in vivo" Nature Medicine, vol. 11, No. 2. 2005 pp. 130-137.
Harbury et al., "Crystal structure of an isoleucine-zipper trimer," Nature, vol. 371, Sep. 1, 1994, 80-83.
Hauer et al., "TNF receptor (TNFR)-associated factor (TRAF) 3 serves as an Inhibitor of TRAF2 5-mediated activation of the noncanonical NF-B pathway by TRAF-binding TNFRs." PNAS, vol. 102, No. 8, Feb. 22, 2005; pp. 2874-2879.
Hay et al., "Replication of Adenovirus Mini-Chromasomes," J. Mol. Biol. (1984) 175, 493-510.

(56) References Cited

OTHER PUBLICATIONS

He et al., "A simplified system for generating recombinant adenoviruses." Proc Natl Acad Sci USA. Mar. 3, 1998;95(5):2509-2514.
Hearing et al., "Identification of a repeated sequence element required for efficient encapsidation of the adenovirus type 5 chromosome." J Virol. Aug. 1987;61(8):2555-2558.
Hearing P., Shenk T., "Functional analysis of the nucleotide sequence surrounding the cap site for adenovirus type 5 region E1A messenger RNAs." J Mol Biol. Jul. 15, 1983;167(4):809-822.
Hermans et al., "CD8+ T cell-dependent elimination of dendritic cells in vivo limits the induction of antitumor immunity." J Immunol. Mar. 15, 2000;164(6):3095-3101.
Ho et al., "Dimeric ligands define a role for transcriptional activation domains in reinitiation." Nature. Aug. 29, 1996;382(6594):822-826.
Hodge et al., "Vector-based delivery of tumor-associated antigens and T-cell co-stimulatory molecules in the induction of immune responses and anti-tumor immunity," Cancer Detect Prevent 2002; 26;275-291.
Holler et al., "Development of improved soluble inhibitors of FasL and CD40L based on oligomerized receptors," Journal of Immunologial Methods 237(2000) 159-173.
Hollstein et al., "Database of p53 gene somatic mutations in human tumors and cell lines." Nucleic Acids Ress. Sep. 1994;22(17):3551-3555.
Holsinger et al., "Signal transduction in T lymphocytes using a conditional allele of Sos." Proc Natl Acad Sci USA. Oct. 10, 1995;92(21):9810-9814.
Horng et al., "*Drosophila* MyD88 is an adapter in the Toll signaling pathway," PNAS 98(22):12654-12658, Oct. 23, 2001.
Hoshino et al., "Cutting edge:Toll-like receptor 4(TLR4)-deficient mice are hyporesponsive to lipopolysaccharide: evidence for TLR4 as the Lps gene product." J Immunol. Apr. 1, 1999;162(7):3749-3752.
Hostager et al., "Different: CD40-mediated Signaling Events Require Distinct CD40 Structural features," J. Immunol. 157:1047-1053, Aug. 1, 1996.
Hou WS, Van Parijs L., "A Bcl-2-dependent molecular timer regulates the lifespan and immunogenicity of dendritic cells." Nat Immunol. Jun. 2004;5(6):583-589.
Inaba et al., "Generation of large numbers of dendritic cells from mouse bone marrow cultures supplemented with granulocyte/macrophage colony-stimulating factor" J. Exp. Med. (1992) 176:1693-702.
Inman et al., "Costimulation, coinhibition and cancer", Current Cancer Drug Targets (2007) 7:15-30.
Ismaili et al., "Monophosphoryl lipid a activates both human dendritic cells and T cells." J Immunol. Jan. 15, 2002;168(2):926-932.
Israeli et al., "Expression of the prostate-specific membrane antigen." Cancer Res. Apr. 1, 1994;54(7):1807-11.
Israeli et al., "Sensitive nested reverse transcription polymerase chain reaction detection of circulating prostatic tumor cells: comparison of prostate-specific membrane antigen and prostate-specific antigen-based assays." Cancer Res. Dec. 15, 1994;54(24):6306-10.
Israeli et al., Molecular cloning of a complementary DNA encoding a prostate-specific membrane antigen. Cancer Res. Jan. 15, 1993;53(2):227-230.
Iuliucci et al., "Intravenous safety and pharmacokinetics of a novel dimerizer drug, AP1903, in healthy volunteers." J Clin Pharmacol. Aug. 2001;41(8):870-9.
Jackson et al., "A second tyrosinase-related protein, TRP-2, maps to and is mutated at the mouse slaty locus." EMBO J. Feb. 1992;11(2):527-535.
Jacquot et al, "CD154/CD40 and CD70/CD27 interactions have different and sequential functions in T cell-dependent B cell responses: enhancement of plasma cell differentiation by CD27 signaling," J Immunol 1997; 159: 2652-2657.
Janeway et al., "Approaching the asymptote? Evolution and revolution in immunology." Cold Spring Harb Symp Quant Biol. 1989;54 Pt 1:1-13.
Jemal et al., "Cancer statastics, 2008." CA Cancer J Clin. Mar.-Apr. 2008;58(2):71-96.
Jonuleit et al., "Pro-inflammatory cytokines and prostaglandins induce maturation of potent immunostimulatory dendritic cells under fetal calf serum-free conditions," Eur. J. Immunol 27:3135-3142, Dec. 1997.
Josien et al., "TRANCE, a tumor necrosis factor family member, enhances the longevity and adjuvant properties of dendritic cells in vivo." J Exp Med. Feb. 7, 2000;191(3):495-502.
Kadowaki N. et al., "Subsets of human dendritic cell precursors express different toll-like receptors and respond to different microbial antigens," J Exp Med. 2001, vol. 194, pp. 863-869.
Kagan JC, Medzhitov R., "Phosphoinositide-mediated adaptor recruitment controls Toll-like receptor signaling." Cell. Jun. 2, 2006;125(5):943-955.
Kageyama et al., "Differing utilization of homologous transcription initiation sites of rat K and T kininogen genes under inflammation condition." J Biol Chem. Feb. 15, 1987;262(5):2345-2351.
Kalams et al., "The critical need for CD4 help in maintaining effective cytotoxic T lymphocyte responses." J Exp Med. Dec. 21, 1998;188(12):2199-2204.
Kalinski et al., "Dendritic cells, obtained from peripheral blood precursors in the presence of PGE2, promote Th2 responses." Adv Exp Med Biol. 1997;417:363-367.
Kalinski et al., "Prostaglandin E(2) is a selective inducer of interleukin-12 p40 (IL-12p40) production and an inhibitor of bioactive IL-12p70 heterodimer." Blood. Jun. 1, 2001;97(11):3466-3469.
Kalinski et al., "T-cell priming by type-1 and type-2 polarized dendritic cells: the concept of a third signal" Immunol. Today (1999) 20:561-7.
Kandel ES, Hay N., "The regulation and activities of the multifunctional serine/threonine kinase Akt/PKB." Exp Cell Res. Nov. 25, 1999;253(1):210-229.
Kanto et al., "Ceramide mediates tumor-induced dendritic cell apoptosis." J Immunol. Oct. 1, 2001;167(7):3773-3784.
Kantoff et al., "Overall survival analysis of a phase II randomized controlled trial of a Poxviral-based PSA-targeted immunotherapy in metastatic castration-resistant prostate cancer." J Clin Oncol. Mar. 1, 2010;28(7):1099-105.
Kantoff et al., "Sipuleucel-T immunotherapy for castration-resistant prostate cancer." N Engl J Med. Jul. 29, 2010;363(5):411-22.
Kaplitt et al., "Long-term gene expression and phenotypic correction using adeno-associated virus vectors in the mammalian brain." Nat Genet. Oct. 1994;8(2):148-154.
Kaplitt et al., "Long-term gene transfer in porcine myocardium after coronary infusion of an adeno-associated virus vector." Ann Thorac Surg. Dec. 1996;62(6):1669-76.
Kawakami et al., "Identification of a human melanoma antigen recognized by tumor-infiltrating lymphocytes associated with in vivo tumor rejection." Proc Natl Acad Sci USA. Jul. 5, 1994;91(14):6458-6462.
Kawakami et al., "Identification of the immunodominant peptides of the MART-1 human melanoma antigen recognized by the majority of HLA-A2-restricted tumor infiltrating lymphocytes." J Exp Med. Jul. 1, 1994;180(1):347-352.
Kehry, Marilyn R., "CD40-Mediated Signaling in B Cells, Balancing Cell Survival, Growth and Death," The American Association of Immunologists, 1996, 2345-2348.
Kelleher et al., "Lipopolysaccharide Modulation of Dendritic Cells is Insufficient to Mature Dendritic Cells to Generate CTLs from Native Polyclonal CD8+ T Cells In Vitro, Whereas CD40 Ligation is Essential," The Journal of Immunology, The American Society of Immunologists, vol. 167, No. 11, Jan. 1, 2001, pp. 6247-6255.
Kelly WK, Slovin SF., "Chemotherapy for androgen-independent prostate cancer: myth or reality." Curr Oncol Rep. Sep. 2000;2(5):394-401.
Kemnade et al., "Off-the-shelf Adenoviralmediated Immunotherapy via Bicistronic Expression of Tumor Antigen and iMyD88/CD40 Adjuvant" Mol. Ther. (2012) 20(7):1462-71.

(56) References Cited

OTHER PUBLICATIONS

Kempf et al, "Improved stimulation of human dendritic cells by receptor engagement with surface-modified microparticles," J Drug Target vol. 11 No. 1, Jan. 2003 pp. 11-18.
Kessler et al., "Gene delivery to skeletal muscle results in sustained expression and systemic delivery of a therapeutic protein." Proc Natl Acad Sci USA. Nov. 26, 1996;93(24):14082-14087.
Kikuchi et al., "Dendritic cells genetically modified to express CD40 ligand and pulsed with antigen can initiate antigen-specific humoral immunity independent of CD4+ T cells." Nat Med. Oct. 2000;6(10):1154-1159.
Klein et al., "High-velocity microprojectiles for delivering nucleic acids into living cells," (1987) Nature, 327,70-73.
Kobayashi et al., "IRAK-M is a negative regulator of Toll-like receptor signaling." Cell. Jul. 26, 2002;110(2):191-202.
Koeberl et al., "Persistent expression of human clotting factor IX from mouse liver after intravenous injection of adeno-associated virus vectors." Proc Natl Acad Sci USA. Feb. 18, 1997;94(4):1426-1431.
Kohler G, Milstein C., "Continuous cultures of fused cells secreting antibody of predefined specificity." Nature. Aug. 7, 1975;256(5517):495-497.
Kohler G, Milstein C., "Derivation of specific antibody-producing tissue culture and tumor lines by cell fusion." Eur J Immunol. Jul. 1976;6(7):511-519.
Kopytek et al., "Chemically induced dimerization of dihydrofolate reductase by a homobifunctional dimer of methotrexate." Chem Biol. May 2000;7(5):313-321.
Korst et al., "Effect of adenovirus gene transfer vectors on the immunologic functions of mouse dendritic cells." Mol Ther. Mar. 2002;5(3):307-315.
Kraaij et al., "Prostate specific membrane antigen (PSMA) is a tissue-specific target for adenoviral transduction of prostate cancer in vitro." Prostate. Feb. 15, 2005;62(3):253-9.
Krug et al., "Toll-like receptor expression reveals CpG DNA as a unique microbial stimulus for plasmacytoid dendritic cells which synergizes with CD40 ligand to induce high amounts of IL-12." Eur J. Immunol. 31:3026-3037.
Kumar et al., "Immunogenicity testing of a novel engineered HIV-1 envelope gp140 DNA vaccine construct." DNA Cell Biol. Jul. 2006;25(7):383-392.
Kutzler et al., "Coimmunization with an optimized IL-15 plasmid results in enhanced function and longevity of CD8 T cells that are partially independent of CD4 T cell help." J Immunol. Jul. 1, 2005;175(1):112-123.
Kutzler MA, Weiner DB., "DNA vaccines: ready for prime time?" Nat Rev Genet. Oct. 2008;9(10):776-788.
Kwon et al., "Isolation and sequence of a cDNA clone for human tyrosinase that maps at the mouse c-albino locus." Proc Natl Acad Sci USA. Nov. 1987;84(21):7473-7477.
Labeur et al., "Generation of tumor immunity by bone marrow-derived dendritic cells correlates with dendritic cell maturation stage." J Immunol. Jan. 1, 1999;162(1):168-175.
Laddy et al., "Heterosubtypic protection against pathogenic human and avian influenza viruses via in vivo electroporation of synthetic consensus DNA antigens." PLoS One. Jun. 25, 2008;3(6):e2517.
Langenkamp et al., "Kinetics of dendritic cell activation: impact on priming of TH1, TH1 and nonpolarized T cells." Nat Immunol. Oct. 2000;1(4):311-316.
Lanzavecchia A, Sallusto F., "Dynamics of T lymphocyte responses: intermediates, effectors, and memory cells." Science. Oct. 6, 2000;290(5489):92-97.
Lanzavecchia A, Sallusto F., "Regulation of T cell immunity by dendritic cells." Cell. Aug. 10, 2001;106(3):263-266.
Lapointe et al., "Human dendritic cells require multiple activation signals for the efficient generation of tumor antigen-specific T lymphocytes." Eur J Immunol. Nov. 2000;30(11):3291-3298.

Lapteva et al., "Development of Novel CD4-Independent iCD40-Dendritic Cell Vaccine for HIV-1 Immunotherapy," vol. 17, No. Suppl 1, May 2009, 12th Annual Meeting of the American Society of Gene Therapy: San Diego, CA, May 27-30, 2009.
Lapteva et al., "Enhance Activation of Human Dendritic Cells by inducible CD40 and Toll-like Receptor-4 Ligation," Cancer Research 2007, 67; (21) Nov. 1, 2007, pp. 10528-10537.
Lee et al., "A clinical grade cocktail of cytokines and PGE2 results in uniform maturation of human monocyte-derived dendritic cells: implications for immunotherapy." Vaccine. Dec. 19, 2002;20 Suppl 4:A8-A22.
Lee et al., "Cytoplasmic domain-mediated dimerizations of toll-like receptor 4 observed by beta-lactamase enzyme fragment complementation." J Biol Chem. Mar. 12, 2004;279(11):10564-10574.
Leo et al., "Partition coefficients and their uses." Chem Rev. Dec. 1971;71(6):525-616.
Levrero et al., "Defective and nondefective adenovirus vectors for expressing foreign genes in vitro and in vivo." Gene. May 30, 1991;101(2):195-202.
Leyton et al., "Humanized radioiodinated minibody for imaging of prostate stem cell antigen-expressing tumors", Clinical Cancer Research: an Official Journal of the American Association for Cancer Research (2008) 14:7488-7496.
Li et al., "A novel conditional Akt 'survival+A185 switch' reversibly protects cells from apoptosis." Gene Ther. Feb. 2002;9(4):233-244.
Li et al., "The HIV-1 Env protein signal sequence retards its cleavage and down-regulates the glycoprotein folding." Virology. Jul. 5, 2000;272(2):417-428.
Liu et al., "Constitutive and antibody-induced internalization of prostate-specific membrane antigen." Cancer Res. Sep. 15, 1998;58(18):4055-60.
Liu et al., "Differential regulation of interleukin (IL)-12 p35 and p40 gene expression and interferon (IFN)-gamma-primed IL-12 production by IFN regulatory factor 1." J Exp Med. Oct. 2003;198(8):1265-1276.
Liu et al., "Monoclonal antibodies to the extracellular domain of prostate-specific membrane antigen also react with tumor vascular endothelium." Cancer Res. Sep. 1, 1997;57(17):3629-34.
Livak et al., "Analysis of relative gene expression data using real-time quantitative PCR and the 2(-Delta Delta C(T)) Method." Methods. Dec. 2001;25(4):402-408.
Lodge et al., Dendridic Cell-based Immunotherapy of Prostate Cancer: Immune Monitoring of a Phase II Clincal Trial, Cancer Res. 60:829-833, 2000.
Loiarro et al., "Peptide-mediated interference of TIR domain dimerization in MyD88 inhibits interleukin-1-dependent activation of NF-{kappa}B." J Biol. Chem. Apr. 22, 2005;280(16):15809-15814.
Luft et al., "Functionally distinct dendritic cell (DC) populations induced by physiologic stimuli: prostaglandin E(2) regulates the migratory capacity of specific DC subsets." Blood. Aug. 15, 2002;100(4):1362-1372.
Luke et al., "The family of five: TIR-domain-containing adaptors in Toll-like receptors signaling" Nature Reviews Immunology (2007) 7:353-364.
Luo et al., "Oligomerization activates c-RAF-1 through a Ras-dependent mechanism." Nature. Sep. 12, 1996;383(6596):181-185.
MacCorkle et al., "Synthetic activation of caspases: artificial death switches." Proc Natl Acad Sci USA. Mar. 31, 1998;95(7):3655-3660.
Macejak DG, Sarnow P., "Internal initiation of translation mediated by the 5' leader of a cellular mRNA." Nature. Sep. 5, 1991;353(6339):90-94.
Machiels et al., "Prospective randomized study comparing docetaxel, estramustine, and prednisone with docetaxel and prednisone in metastatic hormone-refractory prostate cancer." J Clin Oncol. Nov. 10, 2008;26(32):5261-8.
Malin et al., "Vaccinia expression of *Mycobacterium tuberculosis*-secreted proteins: tissue plasminogen activator signal sequence enhances expression and immunogenicity of *M. tuberculosis* Ag85." Microbes Infect. Nov. 2000;2(14):1677-1685.
Malissen B, Ewbank JJ., "'TaiLoRing' the response of dendritic cells to pathogens." Nat Immunol. Aug. 2005;6(8):750-769.

(56) References Cited

OTHER PUBLICATIONS

Mann et al., "Construction of a retrovirus packaging mutant and its use to produce helper-free defective retrovirus." Cell. May 1983;33(1):153-159.
Marsland et al., "CCL19 and CCL21 induce a potent proinflammatory differentiation program in licensed dendritic cells." Immunity. Apr. 2005;22(4):493-505.
Martin, "CD40 signaling in CD8+CD40+ T cells turns on contra-T regulatory cell functions", J. Immunol. (2010) 184:5510-8.
Martln-Fontecha et al., "Regulation of dendritic cell migration to the draining lymph node: impact on T lymphocyte traffic and priming." J Exp Med. Aug. 18, 2003;198(4):615-621.
Mazouz et al., "CD40 triggering increases the efficiency of dendritic cells for antitumoral immunization." Cancer Immun. Mar. 27, 2002;2:2.
McCown et al., "Differential and persistent expression patterns of CNS gene transfer by an adeno-associated virus (AAV) vector." Brain Res. Mar. 25, 1996;713(1-2):99-107.
McIlroy et al., "Histamine and prostaglandin E up-regulate the production of Th2-attracting chemokines (CCL17 and CCL22) and down-regulate IFN-gamma-induced CXCL10 production by immature human dendritic cells." Immunology. Apr. 2006;117(4):507-516.
McWhirter et al., "Crystallographic analysis of CD40 recognition and signaling by human TRAF2." Proc Natl Acad Sci USA. Jul. 20, 1999;96(15):8408-8413.
Medema et al., "Expression of the serpin serine protease inhibitor 6 protects dendritic cells from cytotoxic T lymphocyte-induced apoptosis: differential modulation by T helper type 1 and type 2 cells." J Exp Med. Sep. 3, 2001;194(5):657-667.
Medzhitov et al., "A human homologue of the *Drosophila* Toll protein signals activation of adaptive immunity." Nature. Jul. 24, 1997;388(6640):394-397.
Medzhitov et al., Molecular Cell, 2:253-258, 1998.
Megiovanni et al., "Double-stranded RNA stimulation of CD40 ligation of monocyte-derived dendritic cells as models to study their activation and maturation process." Eur Cytokine Netw. Apr.-Jun. 2004;15(2):126-134.
Melief et al., "Effective therapeutic anticancer vaccines based on preCision guiding of cytolytic T lymphocytes" Immunol Rev. vol. 188, Oct. 2002, pp. 177-182.
Meyer et al., "Cutting edge: cyclooxygenase-2 activation suppresses Th1 polarization in response to helicobacter pylori." J Immunol. Oct. 15, 2003;171(8):3913-3917.
Meylan et al., "Intracellular pattern recognition receptors in the host response." Nature. Jul. 6, 2006;442(7098):39-44.
Miga et al., "Dendritic cell longevity and T cell persistence is controlled by CD154-CD40 interactions." EurJ Immunol. Mar. 2001;31(3):959-965.
Mizukami et al., "Adeno-associated virus type 2 binds to a 150-kilodalton cell membrane glycoprotein." Virology. Mar. 1, 1996;217(1):124-130.
Mochizuki et al., "Akt protein kinase inhibits non-apoptotic programmed cell death induced by ceramide." J Biol Chem. Jan. 25, 2002;277(4):2790-2797.
Montgomery et al., "Heterologous and homologous protection against influenza A by DNA vaccination: optimization of DNA vectors." DNA Cell Biol. Nov. 1993;12(9):777-783.
Morgan et al., "Cancer regression in patients after transfer of genetically engineered lymphocytes." Science. Oct. 6, 2006;314(5796):126-129.
Morse et al., "Migration of human dendritic cells after injection in patients with metastic malignancies." Cancer Res. Jan. 1, 1999;5((1):56-58.
Mukherjee et al., "Lipid-dependent recruitment of neuronal Src to lipid rafts in the brain." J Biol Chem. Oct. 17, 2003;278(42):40806-40814.
Nabel et al., "Recombinant gene expression in vivo within endothelial cells of the arterial wall." Science. Jun. 16, 1989;244(4910)1 342-1344.

Nakagami et al., "Safety and efficacy of docetaxel, estramustine phosphate and hydrocortisone in hormone-refractory prostate cancer patients." Int J Urol. Jul. 2010;17(7):629-34.
Napolitani et al., "Selected Toll-like receptor agonist combinations synergistically trigger a T helper type 1-polarizing program in dendrinic cells," Nat Immunol. Aug. 2005; vol. 6. No. 8, pp. 769-776.
Narayanan et al. A composite MyD88/CD40 switch synergistically activates mouse and human dendritic cells for enhanced antitumor efficacy. J Clin Invest. 2011, vol. 121(4), p. 1524-1534, and Supplementary Materials pp. 1-16.
Narayanan et al., "The iCD40.MyD88 combo-vector: A new platform for enhanced DC tumor immunotherapy", Proceedings of the American Association for Cancer Research Annual Meeting, vol. 51, Apr. 15, 2010, 1158.
Narum et al., "Codon optimization of gene fragments encoding Plasmodium falciparum merzoite proteins enhances DNA vaccine protein expression and immunogenicity in mice." Infect Immun. Dec. 2001;69(12):7250-7253.
Nestle et al., "Dendritic cells: On the move from bench to bedside." Nat Med. Jul. 2001;7(7):761-765.
Ni et al., "Molecular basis for CD40 signaling mediated by TRAF3." Proc Natl Acad Sci USA. Sep. 12, 2000;97(19):10395-10399.
Nicolau et al., "Liposomes as carriers for in vivo gene transfer and expression." Methods Enzymol. 1987;149:157-176.
Nishiya et al., "Ligand-regulated chimeric receptor approach reveals distinctive subcellular localization and signaling properties of the Toll-like receptors," J. Biol, Chem. 279(18):19008-19017, 2004.
Nociari et al., "A novel one-step, highly sensitive fluorometric assay to evaluate cell-mediated cytotoxicity." J Immunol Methods. Apr. 15, 1998;213(2):157-167.
Nopora A, Brocker T., "Bcl-2 controls dendritic cell longevity in vivo." J Immunol. Sep. 15, 2002;169(6):3006-3014.
Oehm et al., "Purification and Molecular Cloning of the APO-1 Cell Surface Antigen, a Member of the Tumor Necrosis Factorperve Growth Factor Receptor Superfamily, Sequence Identity With the Fas Antigen*," The Journal of Biological Chemistry, vol. 267, No. 15, May 25, 1992 10709-10715.
Ohshima et al., "Expression and function of OX40 ligand on human dendritic cells." J Immunol. Oct. 15, 1997;159(8):3838-3848.
Oliviero et al., "The human haptoglobin gene: transcriptional regulation during development and acute phase induction." EMBO J. Jul. 1987;6(7):1905-1912.
O'Neill et al., "Manipulating dendritic cell biology for the active immunotherapy of cancer." Blood. Oct. 15, 2004;104(8):2235-2246.
O'Sullivan B, Thomas R., "CD40 and dendritic cell function." Crit Rev Immunol. 2003;23(1-2):83-107.
Ozinsky et al., "The repertoire for pattern recognition of pathogens by the innate immune system is defined by cooperation between toll-like receptors." Proc Natl Acad Sci USA. Dec. 5, 2000;97(25):13766-13771.
Page et al., "A nonisotopic method for the measurement of cell membrane integrity." Anticancer Res. Jul.-Aug. 1998;18(4A):2313-2316.
Palecek et al., "Integrin-ligand binding properties govern cell migration speed through cell-substratum adhesiveness." Nature. Feb. 6, 1997;385(6616):537-540.
Park et al, "An essential role for Akt1 in dendritic cell function and tumor immunotherapy," Nature Biology, vol. 24, No. 12, Dec. 2006, pp. 1581-1590.
Park et al., "Cutting Edge: CpG DNA inhibits dendritic cell apoptosis by up-regulating cellular inhibitor of apoptosis proteins through the phosphatidylinositide-3'-OH kinase pathway." J Immunol. Jan. 1, 2002;168(1):5-8.
Pasare C, Medzhitov R., "Toll pathway-dependent blockade of CD4+CD25+ T cell-mediated suppression by dendritic cells." Science. Feb. 14, 2003;299(5609):1033-1036.
Paskind et al., "Dependence of Moloney murine leukemia virus production on cell growth." Virology. Sep. 1975;67(1):242-248.
Pelletier J, Sonenberg N., "Internal initiation of translation of eukaryotic mRNA directed by a sequence derived from poliovirus RNA." Nature. Jul. 28, 1998;334(6180):320-325.

(56) References Cited

OTHER PUBLICATIONS

Perales et al., "Gene transfer in vivo: sustained expression and regulation of genes introduced into the liver by receptor-targeted uptake." Proc Natl Acad Sci USA. Apr. 26, 1994;91(9):4086-4090.
Ping et al., "Altered beta-adrenergic receptor signaling in heart failure, in vivo gene transfer via adeno and adeno-associated virus." Microcirculation. Jun. 1996;3(2):225-228.
Pinto et al., "Prostate-specific membrane antigen: a novel folate hydrolase in human prostatic carcinoma cells." Clin Cancer Res. Sep. 1996;2(9):1445-51.
Poli V, Cortese R., "Interleukin 6 induces a liver-specific nuclear protein that binds to the promoter of acute-phase genes." Proc Natl Acad Sci USA. Nov. 1989;86(21):8202-8206.
Potter et al., "Enhancer-dependent expression of human kappa immunoglobulin genes introduced into mouse pre-B lymphocytes by electroporation." Proc Natl Acad Sci USA. Nov. 1984;81(22):7161-7165.
Prins et al., "The TLR-7 agonist, imiquimod, enhances dendritic cell survival and promotes tumor antigen-specific T cell priming: relation to central nervous system antitumor immunity." J Immunol. Jan. 1, 2006;176(1):157-164.
Prowse KR, Baumann H., "Hepatocyte-stimulating factor, beta 2 interferon, and interleukin-1 enhance expresson of the rat alpha 1-acid glycoprotein gene via a distal upstream regulatory region." Mol Cell Biol. Jan. 1988;8(1):42-51.
Pruschy et al., "Mechanistic Sutdies of a Signaling Pathway Activated by the Organic Dimerizer FK1012," Chemistry and Biology 1994 vol. 1, No. 3, 163-172.
Puccetti et al., "Effects of IL-12 and IL-23 on antigen-presenting cells at the interface between innate and adaptive immunity." Crit Rev Immunol. 2002;22(5-6):373-390.
Pullen et al., "CD40 signaling through tumor necrosis factor receptor-associated factors (TRAFs). Binding site specificity and activation of downstream pathways by distinct TRAFs." J Biol Chem. May 14, 1999;274(20):14246-14254.
Ramos et al., "An Inducible Caspase 9 Suicide Gene to Improve the Safety of Mesenchymal Stromal Cell Therapies," Stem Cells, Translational and Clinical Research, Apr. 15, 2010, pp. 1-16.
Re F, Strominger JL., "Toll-Ike receptor 2(TLR2) and TLR4 differentially activate human dendritic cells." J Biol Chem. Oct. 5, 2001;276(40):37692-37699.
Reis e Sousa C., "Dendritic cells as sensors of infection." Immunity. May 2001;14(5):495-498.
Renan MJ., "Cancer genes: current status, future prospects, and applications in radiotherapy/oncology." Radiother Oncol. Nov. 1990;19(3):197-218.
Rescigno et al., "Dendritic cell survival and maturation are regulated by different signaling pathways." J Exp Med. Dec. 7, 1998;188(11):2175-2180.
Richard et al, "Expansion of Genetically modified Primary Human HemopOietic cells Using Chemical Inducers of Dimerization," Blood vol. 95, 2000 pp. 430-436.
Rickert et al., "Signaling by the tumor necrosis factor receptor superfamily in B-cell biology and disease", Immunological Reviews (2011) 244:115-133.
Ridge et al., "A conditioned dendritic cell can be a temporal bridge between a CD4+ T-helper and a T-Killer cell." Nature. Jun. 4, 1998;393(6684):474-478.
Ridgway D., "The first 1000 dendritic cell vaccinees." Cancer Invest. 2003;21(6):873-886.
Riol-Blanco et al., "The chemokine receptor CCR7 activates in dendritic cells two signaling modules that independently regulate chemotaxis and migratory speed." J Immunol. Apr. 1, 2005;174(7):4070-4080.
Rippe et al., "DNA-mediated gene transfer into adult rat hepatocytes in primary culture." Mol Cell Biol. Feb. 1990;10(2):689-695.
Rivera et al., "A humanized system for pharmacologic control of gene expression." Nat Med. Sep. 1996;2(9):1028-1032.
Rivera, V.M., "Controlling Gene Expression USing SynthetiC Ligands," Methods: A companion to Methods in Enzymology vol. 14,1998 pp. 421-429.
Riviere et al., "Effects of retroviral vector design on expression of human adenosine deaminase in murine bone marrow transplant recipients engrafted with genetically modified cells" PNAS USA (1995) 92:6733-6737.
Ron et al., "Angiotensinogen gene-nducible enhancer-binding protein 1, a member of a new family of large nuclear proteins that recognize nuclear factor kappa B-binding sites through a zinc finger motif." Mol Cell Biol. May 1991;11(5):2887-2895.
Ronni et al., "Common interaction surfaces of the toll-like receptor 4 cytoplasmic domain stimulate multiple nuclear targets," Molecular and Cellular Biology, Apr. 2003, vol. 23, No. 7, pp. 2543-2555.
Rosenberg SA., "A new era for cancer immunotherapy based on the genes that encode cancer antigens." Immunity. Mar. 1999;10(3):281-287.
Roux et al., "A versatile and potentially general approach to the targeting of specific cell types by retrovirus: application to the infection of human cells by means of major histocompatibility complex class I and class II antigens by mouse ecotropic murine leukemia virus-derived viruses." Proc Natl Acad Sci USA. Dec. 1989;86(23):9079-9083.
Rudinger, "Characteristics in the amino acids as components of a peptide hormone sequence" Chapter 1 in Peptide Hormones, Biological Council, The Co-ordinating Committee for Symposia on Drug Action, Edited by J.A. Parsons, University Park Press, Baltimore, London, Tokyo, Jun. 1976; pp. 1-7.
Salkowski et al., "Lipopolysaccharide and monophosphoryl lipid a differentially regulate interleukin-12, gamma interferon, and interleukin-10 mRNA production in murine macrophages." Infect Immun. Aug. 1997;65(8):3239-3247.
Sallusto et al., "Rapid and coordinated switch in chemokine receptor expression during dendritic cell maturation." Eur J Immunol. Sep. 1998;28(9):2760-2769.
Samulski et al., "A recombinant plasmid from which an infectious adeno-associated virus genome can be excised in vitro and its use to study viral replication." J Virol. Oct. 1987;61(10):3096-3101.
Sanchez-Sanchez et al., "The multiple personalities of the chemokine receptor CCR7 in dendritic cells." J Immunol. May 1, 2006;176(9):5153-5159.
Sardesai et al., "Electroporation delivery of DNA vaccines: prospects for success" Current Opinion in Immunol. (2011) 23:421-9.
Sato et al., "Combination of monocyte-derived dendrinic cells and activated T cells which express CD40 ligand" an new approach to cancer Immunotherapy, Cancer Imminol Immunther, vol. 53, No. 1, Jan. 2004, pp. 53-61.
Scandella et al., "CCL19/CCL21-triggered signal transduction and migration of dendritic cells requires prostaglandin E2." Blood. Mar. 1, 2004;103(5):1595-1601.
Scandella et al., "Prostaglandin E2 is a key factor for CCR7 surface expression and migration of monocyte-derved dendritic cells." Blood. Aug. 15, 2002;100(4):1354-1361.
Schellhammer et al., "Prostate specific antigen decreases after withdrawal of antiandrogen therapy with bicalutamide or flutamide in patients receiving combined androgen blockade." J Urol. May 1997;157(5):1731-1735.
Schenten et al., "Signaling through the adaptor molecule MyD88 in CD4+ T cells is required to overcome suppression by regulatory T cells", Immunity (2014) 40:78-90.
Scher et al., "Clinical trials in relapsed prostate cancer: defining the target." J Natl Cancer Inst. Nov. 20, 1996;88(22):1623-1634.
Scher et al., "Design and end points of clinical trials for patients with progressive prostate cancer and castrate levels of testosterone: recommendations of the Prostate Cancer Clinical Trials Working Group." J Clin Oncol. Mar. 1, 2008;26(7):1148-59.
Scher Hi, Kelly WK., "Flutamide withdrawal syndrome: its impact on clinical trials in hormone-refractory prostate cancer." J Clin Oncol. Aug. 1993;11(8):1566-1572.
Schneider et al., "Inactivation of the human immunodeficiency virus type 1 inhibitory elements allows Rev-independent expression of Gag and Gag/protease and particle formation." J Virol. Jul. 1997;71(7):4892-4903.

(56) References Cited

OTHER PUBLICATIONS

Schoenberger et al., "T-cell help for cytotoxic T lymphocytes is mediated by CD40-CD40L interactions." Nature. Jun. 4, 1998;393(6684):480-483.

Schuler et al., "The use of dendritic cells in cancer immunotherapy." Curr Opin Immunol. Apr. 2003; 15(2):138-147.

Schuler et al., "Dendritic cells as adjuvants for immune-mediated resistance to tumors" J. Exp. Med. (1997) 186:1183-7.

Schultz et al., "CD40 triggering of heterodimeric IL-12 p70 production by dendritic cells in vivo requires a microbial priming signal," Immunity, vol. 13, No. 4, Oct. 2000. pp. 453-462.

Schuster, et al., "ALD518, a humanized anti-IL-6 antibody, treats anemia in patients with advanced non-small cell lung cancer (NSCLC): Results of a phase II, randomized, double-blind, placebo-controlled trial," 2010, J. Clin. Oncol. 28-7s (suppl.; abstr. 7631).

Schweitzer BA, Kool ET., "Aromatic Nonpolar Nucleosides as Hydrophobic Isosteres of Pyrimidine and Purine Nucleosides." J Org Chem. Dec. 1, 1994;59(24):7238-7242.

Shaffer et al., "Circulating tumor cell analysis in patients with progressive castration-resistant prostate cancer." Clin Cancer Res. Apr. 1, 2007;13(7):2023-9.

Shen et al., "Silencing of SOCS1 enhances antigen presentation by dendritic cells and antigen-specific anti-tumor immunity." Nat Biotechnol. Dec. 2004;22(12):1546-1553.

Silver et al., "Prostate-specific membrane antigen expression in normal and malignant human tissues." Clin Cancer Res. Jan. 1997;3(1):81-5.

Simpson et al., "Consequences of Fas-ligand and perforin expression by colon T cells in a mouse model of inflammatory bowel disease." Gastroenterology. Oct. 1998; 115(4):849-855.

Small EJ, Srinivas S., "The antiandrogen withdrawal syndrome. Experience in a large cohort of unselected patients with advanced prostate cancer." Cancer. Oct. 15, 1995;76(8):1428-1434.

Small EJ, Vogelzang NJ., "Second-line hormonal therapy for advanced prostate cancer: a shifting paradigm." J Clin Oncol. Jan. 1997;15(1):382-388.

Smith et al., "Cognate CD4(+) T cell licensing of dendritic cells in CD8(+) T cell immunity." Nat Immunol. Nov. 2004;5(11):1142-1148.

Smith et al., "DNA/MVA vaccine for HIV type 1:effects of codon-optimization and the expression of aggregates or virus-like particles on the immunogenicity of the DNA prime." AIDS Res Hum Retroviruses. Dec. 2004;20(12):1335-1347.

Snyder et al., "Prostaglandins modulate macrophage la expression." Nature. Sep. 9, 1982;299(5879):163-165.

Sonpavde, et al., "Vaccine therapy for prostate cancer", Urologic Oncology, Elsevier, NY, vol. 25, No. 6, Nov. 1, 2007, 451-459.

Sorensen et al., "Endostatin reduces cascularization, blood flow, and growth in a rat gliosarcoma." Neuro Oncol. Jan. 2002;4(1):1-8.

Spencer et al., "A general strategy for producing conditional alleles of Src-like tyrosine kinases." Proc Natl Acad Sci USA Oct. 10, 1995;92(21):9805-9809.

Spencer et al., "Controlling signal transduction with synthetic ligands." Science. Nov. 12, 1993;262(5136):1019-1024.

Spencer et al., "Functional analysis of Fas signaling in vivo using synthetic inducers of dimerization." Curr Biol. Jul. 1, 1996;6(7):839-847.

Sporri R, Reis e Sousa C., "Inflammatory mediators are insufficient for full dendritic cell activation and promote expansion of CD4+ T cell populations lacking helper function." Nat Immunol. Feb. 2005;6(2):163-170.

Steinman et al., "Tolerogenic dendritic cells." Annu Rev Immunol. 2003;21:685-711.

Steinman RM, Pope M., "Exploiting dendritic cells to improve vaccine efficacy." J Clin Invest. Jun. 2002;109(12):1519-1526.

Strasser et al., "Integrin Activation by Regulated Dimerization and Oligomerization of Platelet Endothelial Cell Adhesion Molecule (PECAM)-1 from Within the Cell," Immunity Review 30, Feb. 20 2009, 180-192.

Strober et al., "Signalling pathways and molecular interactions of NOD1 and NOD2." Nat Rev Immunol. Jan. 2006;6(1):9-20.

Su et al., "Alternatively spliced variants of prostate-specific membrane antigen RNA: ratio of expression as a potential measurement of progression." Cancer Res. Apr. 1, 1995;55(7):1441-1443.

Su et al., "Telomerase mRNA-transfected dendritic cells stimulate antigen-specific CD8+ and CD4+ T cell responses in patients with metastatic prostate cancer." J Immunol. Mar. 15, 2005;174(6):3798-3807.

Suarez-Alvarez et al, Epigenetic Mechanisms Regulate MHC and Antigen Processing Moleculers in Human Embryonic and Induced Pluripotent Stem Cells. PLoS ONE (April) 5(4):e10192, 2010, pp. 1-12.

Suda et al., "Molecular Cloning and Expression of the Fas Ligand, a Novel Member of the Tumor Necrosis Factor Family," Cell vol. 75, 1169-1176 Dec. 17, 1993.

Tai et al., "Mechanisms by which SGN-40, a Humanized Anti-CD40 Antibody, Induces Cytotoxicity in Human Multiple Myeloma Celis: ClinicalImplications," Cancer Research, Apr. 15, 2004, vol. 64, pp. 2846-2852.

Ten Klooster JP, Hordijk PL., "Targeting and localized signalling by small GTPases." Biol Cell. Jan. 2007;99(1):1-12.

Tepler et al., "The gene for the rat mast cell high affinity IgE receptor alpha chain. Structure and alternative mRNA splicing patterns." J Biol Chem. Apr. 5, 1989;264(10):5912-5915.

Termeer et al., "Oligosaccharides of hyaluronan are potent activators of dendritic cells." J Immunol. Aug. 15, 2000;165(4):1863-1870.

Thompson et al., "The low-toxicity versions of LPS, MPL adjuvant and RC529, are efficient adjuvants for CD4+ T Cells." J Leukoc Biol. Dec. 2005;78(6):1273-1280.

Tibbetts C., "Viral DNA sequence from incomplete particles of human adenovirus type 7." Cell. Sep. 1977;12(1):243-249.

Timmerman et al., "Dendritic cell vaccines for cancer immunotherapy", Annu. Rev. Med. (1999) 50:507-29.

Tone M . et al., "Regulation of CD40 function by its isoforms generated through alternative splicing," PNAS. Feb. 13, 2001, vol. 98, No. 4, pp. 1751-1756.

Tong et al, "Prospects for CD40-directed Experimental Therapy of Human Cancer," Cancer Gene Therapy vol. 10, 2003,pp. 1 -13.

Troyer et al., "Detection and characterization of the prostate-specific membrane antigen (PSMA) in tissue extracts and body fluids." Int J Cancer. Sep. 4, 1995;62(5):552-8.

Tur-Kaspa et al., "Use of electroporation to introduce biologically active foreign genes into primary rat hepatocytes." Mol Cell Biol. Feb. 1986;6(2):716-718.

Van der Pouw Krann T.C., et al., "Prostaglandin E2 is a potent inhibitor of human interleukinl2 production," J Exp Med., 1995, vol. 181, pp. 775-779.

Vassiliou et al., "Prostaglandin E2 promotes the survival of bone marrow-derived dendritic cells." J Immunol. Dec. 1, 2004;173(11):6955-6964.

Vidalain et al., "CD40 signaling in human dendritic cells is initiated within membrane rafts." EMBO J. 2000; 19:3304-3313.

Vieweg J, Jackson A., "Modulation of antitumor responses by dendritic cells." Springer Semin Immunopathol. Jan. 2005;26(3):329-341.

Vieweg, "Immunotherapy for Advanced Prostate Cancer," vol. 9 Suppl. 1 (2007) Reviews in Urology S29-S38.

Vincent et al., "Targeting of proteins to membranes through hedgehog auto-processing." Nat Biotechnol. Aug. 2003;21(8):936-940.

Vonderheide et al., "CD40 activation of carcinoma cells increases expression of adhesion and major histocompatibility molecules but fails to induce either CD80/CD86 expression or T cell alloreactivity." Int J Oncol. Oct. 2001;19(4):791-798.

Wagner et al., "IL-12p70-Dependent Th1 Induction by Human B Cells Requires Combined Activation with CD40 Ligand and CpG DNA", Journal of Immunology, vol. 172, 2004, 954-963.

Wagner et al., "Transferrin-polycation conjugates as carriers for DNA uptake into cells." Proc Natl Acad Sci USA. May 1990;87(9):3410-3414.

(56) References Cited

OTHER PUBLICATIONS

Wang et al., "Relative contributions of codon usage, promoter efficiency and leader sequence to the antigen expression and immunogenicity of HIV-1 Env DNA vaccine." Vaccine. May 22, 2006;24(21):4531-4540.
Werneburg et al., "Molecular Characterization of CD40 Signaling Intermediates," The Journal of Biological Chemistry, vol. 276, Nov. 16, 2001, 43334-43342.
Werts et al., "TIR, CARD and PYRIN: three domains for an antimicrobial triad." Cell Death Differ. May 2006;14(5):798-815.
Wesemann et al., "Suppressor of cytokine signaling 1 inhibits cytokine induction of CD40 expression in macrophages." J Immunol. Sep. 1, 2002;169(5):2354-2360.
Wilson et al., "A 58-base-par region of the human C3 gene confers synergistic inducibility by interleukin-1 and interleukin-6." Mol Cell Biol. Dec. 1990;10(12):6181-6191.
Wilson et al., "Implantation of vascular grafts lined with genetically modified endothelial cells." Science. Jun. 16, 1989;244(4910):1344-1346.
Wolchok et al., "Guidelines for the Evaluation of Immune Therapy Activity in Solid Tumors: Immune-Related Response Criteria," Clin Cancer Res 2009;15(23) Dec. 1, 2009, pp. 7412-7420.
Woltman et al., "Rapamycin specifically interferes with GM-CSF signaling in human dendritic cells, leading to apoptosis via increased p27KIP1 expression." Blood. Feb. 15, 2003;101(4):1439-1445.
Wong et al., "Fas Antigen and p55 TNF Receptor Signal Apoptosis Through Distinct Pathways," Journal of Immunology, 1994, 152: pp. 1751-1755.
Wong P, Famer EG., "Feedback regulation of pathogen-specific T cell priming." Immunity. Apr. 2003;18(4):499-511.
Wright et al., "Upregulation of prostate-specific membrane antigen after androgen-deprivation therapy." Urology. Aug. 1996;48(2):326-34.
Wu and Wu, "Liver-directed gene delivery," Adv Drug Delivery Rev, 1993;12:159-167.
Wu et al., "Codon optimization reveals critical factors for high level expression of two rare codon genes in *Escherichia coli*: RNA stability and secondary structure but not tRNA abundance." Biochem Biophys Res Commun. Jan. 2, 2004;313(1):89-96.
Wu GY, Wu CH., "Receptor-mediated in vitro gene transformation by a soluble DNA carrier system." J Biol Chem. Apr. 5, 1987;262(10):4429-32.
Xiao et al., "Efficient long-term gene transfer into muscle tissue of immunocompetent mice by adeno-associated virus vector." J Virol. Nov. 1996;70(11):8098-8108.
Xiao et al., "Establishment of a Cell Model Based on FKBP12 Dimerization for Screening of FK506-like Neurotrophic small Molecular Compounds." J Biomol Screen. Apr. 2006;11(3):225-235.
Xie et al., "Adenovirus-mediated tissue-targeted expression of a caspase-9-based artificial death switch for the treatment of prostate cancer." Cancer Res. Sep. 15, 2001;61(18):6795-6804.
Xu et al., "Optimization of transcriptional regulatory elements for constructing plasmid vectors." Gene. Jul. 11, 2001;272(1-2):149-156.
Yadava A, Ockenhouse CF., "Effect of codon optimization on expression levels of a functionally folded malaria vaccine candidate in prokaryotic and eukaryotic expression systems." Infect Immun. Sep. 2003;71(9):4961-4969.
Yan et al., "Enhanced cellular immune responses elicited by an engineered HIV-1 subtype B consensus-based envelope DNA vaccine." Mol Ther. Feb. 2007;15(2):411-421.
Yanagawa Y, Onoe K., "CCL19 induces rapid dendritic extension of murine dendritic cells." Blood. Sep. 15, 2002;100(6):1948-1956.
Yang et al., "In vivo and in vitro gene transfer to mammalian somatic cells by particle bombardment." Proc Natl Acad Sci USA. Dec. 1990;87(24):9568-9572.
Yang et al., "Induction of inflammation by West Nile virus capsid through the caspase-9 apoptotic pathway." Emerg Infect Dis. Dec. 2002;8(12):1379-1384.
Zechner et al., "Recombinant human cachectin/tumor necrosis factor by not interleukin-1 alpha downregulates lipoprotein lipase gene expression at the transcriptional level in mouse 3T3-L1 adipocytes." Mol Cell Biol. Jun. 1988;8(6):2394-2401.
Zhang et al., "Integrin-nucleated Toll-like receptor (TLR) dimerization reveals subcellular targeting of TLRs and distinct mechanisms of TLR4 activation and signaling." FEBS Lett. Dec. 4, 2002;532(1-2):171-176.
Zhang et al., "mRNA secondary structure at start AUG codon is a key limiting factor for human protein expression in *Escherichia coli*." Biochem Biophys Res Commun. Oct. 13, 2006;349(1):69-78.
Zhao et al., "Integrin Activation by Regulated Dimerization and Oligomerization of Platelet Endothelial Cell Adhesion Molecule (PECAM)-1 from Within the Cell," Jan. 8, 2001, The Journal of Cell Biology, vol. 152, 65-73.
Zhou et al., "Multiple RNA splicing and the presence of cryptic RNA splice donor and acceptor sites may contribute to low expression levels and poor immunogenicity of potential DNA vaccines containing the env gene of equine infectious anemia virus (EIAV)." Vet Microbiol. Aug. 25, 2002;88(2):127-151.
Zitvogel et al., "Therapy of murine tumors with tumor peptide-pulsed dendritic cells: dependence on T cells, B7 costimulation, and T helper cell 1-associated cytokines." J Exp Med. Jan. 1, 1996;183(1):87-97.
Zlatkine et al., "Retargeting of cytosolic proteins to the plasma membrane by the Lck protein tyrosine kinase dual acylation motif." J Cell Sci. Mar. 1997;110(Pt5):673-679.
Zur Medege et al., "Expression and immunogenicity of sequence-modified human immunodeficiency virus type 1 subtype B pol and gagpol DNA vaccines." J Virol. Jun. 2003; 77(11):6197-6207.
International Serch Report and Written Opinon dated Oct. 21, 2011 in International Application No. PCT/US11/032572 filed Apr. 14, 2011 and published as: WO/2011/130566 on Oct. 20, 2011.
International Preliminary Report on Patentability dated Mar. 31, 2011, for International Application No. PCT/US2009/057738, filed Sep. 21, 2009 and published as WO2010033949 on Mar. 25, 2010.
International Search Report and Written Opinion dated Feb. 2, 2010, for International Application No. PCT/US2009/057738, filed Sep. 21, 2009 and publiched as WO2010033949 on Mar. 25, 2010.
International Serch Report and Written Opinon dated Nov. 17, 2008 in International Application no. PCT/US07/81963 filed Oct. 19, 2007 and published as: WO/2008/049113 on Apr. 24, 2008.
International Preliminary Report on Patentability dated Apr. 22, 2009 in International Application No. PCT/US07/81963 filed Oct. 19, 2007 and published as: WO/2008/049113 on Apr. 24, 2008.
Office Action dated Mar. 21, 2008 in U.S. Appl. No. 10/781,384, filed Feb. 18, 2004 now U.S. Pat. No. 7,404,950 on: Jul. 29, 2008.
Office Action dated Jun. 27, 2007 in U.S. Appl. No. 10/781,384, filed Feb. 18, 2004 now U.S. Pat. No. 7,404,950 on: Jul. 29, 2008.
Office Action dated Dec. 27, 2006 in U.S. Appl. No. 10/781,384, filed Feb. 18, 2004 now U.S. Pat. No. 7,404,950 on: Jul. 29, 2008.
Office Action dated May 5, 2006 in U.S. Appl. No. 10/781,384, filed Feb. 18, 2004 now U.S. Pat. No. 7,404,950 on: Jul. 29, 2008.
Office Action dated May 20, 2011 in U.S. Appl. No. 12/165,360, filed Jun. 30, 2008 and Published as: 2008/0269160 on: Oct. 30, 2008.
Office Action dated Oct. 22, 2010 in U.S. Appl. No. 12/165,360, filed Jun. 30, 2008 and Published as: 2008/0269160 on: Oct. 30, 2008.
International Preliminary Report on Patentability dated Sep. 29, 2005 in International Patent Application: PCT/US2004/04757 filed on: Feb. 18, 2004 and published as WO 2004/073641 on: Sep. 2, 2004.
International Search Report dated Jan. 13, 2005 in International Patent Application: PCT/US2004/04757 filed on: Feb. 18, 2004 and published as WO 2004/073641 on: Sep. 2, 2004.
Supplementary European Search Report dated Oct. 4, 2006 in European Application EP04712328, filed on Feb. 18, 2004.
Office Action dated Aug. 17, 2012 in U.S. Appl. No. 12/563,991, filed Sep. 21, 2009 and Published as: 2010/0203067 on: Aug. 12, 2010.
Office Action dated Feb. 7, 2012 in U.S. Appl. No. 12/563,991, filed Sep. 21, 2009 and Published as: 2010/0203067 on: Aug. 12, 2010.

(56) References Cited

OTHER PUBLICATIONS

Extended European Search Report dated Sep. 5, 2012 in European Patent Application No. EP 11193762, filed: Oct. 19, 2007.
Extended European Search Report dated Sep. 12, 2012 in European Patent Application No. EP 11193768 filed: Oct. 19, 2007.
Office Action dated Jun. 3, 2013 in U.S. Appl. No. 12/445,939, filed Oct. 26, 2010 and Published as: 2011/0033383 on: Feb. 10, 2011.
Office Action dated Dec. 26, 2012 in U.S. Appl. No. 12/445,939, filed Oct. 26, 2010 and Published as: 2011/0033383 on: Feb. 10, 2011.
Office Action dated Mar. 13, 2013 in U.S. Appl. No. 13/087,329, filed Apr. 14, 2011 and Published as: 2011/0287038 on: Nov. 24, 2011.
Office Action dated May 22, 2015 in U.S. Appl. No. 13/763,591, filed Feb. 8, 2013 and Published as US 2014-0087468 on Mar. 27, 2014.
Extended European Search Report dated Aug. 9, 2012 in European Application No. EP 09815355, filed on Sep. 21, 2009 based on International Application No. PCT/US2009/057738.
Office Action dated Dec. 1, 2014 in U.S. Appl. No. 13/786,652, filed Mar. 6, 2013 and Published as 2014/0023647 on Jan. 23, 2014.
Office Action dated Aug. 7, 2014 in U.S. Appl. No. 13/786,652, filed Mar. 6, 2013 and Published as 2014/0023647 on Jan. 23, 2014.
Extended European Search Report dated Aug. 26, 2014 in European Application No. EP11769619, filed on Apr. 14, 2011 based on PCT Application No. PCT/US2011/032572.
Office Action dated Dec. 9, 2014 in U.S. Appl. No. 13/786,339, filed Mar. 5, 2013 and Published as US 2013/0183333 on Jul. 18, 2013.
Office Action dated Feb. 6, 2014 in U.S. Appl. No. 13/786,339, filed on Mar. 5, 2013 and Published as US 2013/0183333 on Jul. 18, 2013.
Office Action dated Aug. 15, 2014 in U.S. Appl. No. 13/786,339, filed on Mar. 5, 2013 now U.S. Pat. No. 8,999,949 on Apr. 7, 2015.
Office Action dated Feb. 24, 2014 in U.S. Appl. No. 12/165,360, filed Jun. 30, 2008 and Published as US 2008/0269160 on Oct. 30, 2008.
Office Action dated Nov. 5, 2013 in U.S. Appl. No. 12/165,360, filed Jun. 30, 2008 and Published as US 2008/0269160 on Oct. 30, 2008.
Office Action dated Nov. 18, 2013 in U.S. Appl. No. 12/445,939, filed Oct. 26, 2010 and Published as US 2011/0033383 on Feb. 10, 2011.
Office Action dated Nov. 22, 2013 in U.S. Appl. No. 13/087,329, filed Apr. 14, 2011 and Published as US 2011/0287038 on Nov. 24, 2011.
Extended European Search Report dated Jul. 10, 2015 in European Application No. EP 15157213.8, filed on Feb. 18, 2004 and published as EP 2 933 334 on Oct. 21, 2015.
Office Action dated Oct. 20, 2015 in U.S. Appl. No. 13/087,329, filed Apr. 14, 2011 and Published as US 2011/0287038 on Nov. 24, 2011.
Office Action dated Oct. 20, 2015 in U.S. Appl. No. 13/786,652, filed Mar. 6, 2013 and Published as 2014/0023647 on Jan. 23, 2014.
Office Action dated Nov. 24, 2015 in U.S. Appl. No. 14/191,167, filed Feb. 26, 2014 and Published as 2014-0287490 on Sep. 25, 2014.
Dicker et al., GenBank NM_001250, Oct. 17, 2005.
Office Action dated Dec. 15, 2015 in U.S. Appl. No. 13/763,591, filed Feb. 8, 2013 and Published as US 2014-0087468 on Mar. 27, 2014.
Office Action dated Dec. 22, 2015 in U.S. Appl. No. 13/786,351, filed Mar. 5, 2013 and Published as US 2015-0111294 on Apr. 23, 2015.
Office Action dated Mar. 10, 2016 in U.S. Appl. No. 14/643,989, filed Mar. 10, 2015 and Published as US 2015-0306140 on Oct. 29, 2015.
Office Action dated Apr. 18, 2016 in U.S. Appl. No. 14/191,167, filed Feb. 26, 2014 and Published as 2014-0287490 on Sep. 25, 2014.

Office Action dated Apr. 22, 2016 in U.S. Appl. No. 13/786,351, filed Mar. 5, 2013 and Published as US 2015-0111294 on Apr. 23, 2015.
Office Action dated Apr. 27, 2016 in U.S. Appl. No. 13/786,652, filed Mar. 6, 2013 and Published as 2014/0023647 on Jan. 23, 2014.
Office Action dated May 9, 2016 in U.S. Appl. No. 13/087,329, filed Apr. 14, 2011 and Published as US 2011/0287038 on Nov. 24, 2011.
Ariad Pharmaceuticals, Inc., "ARGENT Regulated Homodimerization Kit" Version 2.0, product brochure, Sep. 9, 2002.
Office Action dated Sep. 15, 2016 in U.S. Appl. No. 14/191,167, filed Feb. 26, 2014 and Published as 2014-0287490 on Sep. 25, 2014.
Office Action dated Oct. 7, 2016 in U.S. Appl. No. 14/643,989, filed Mar. 10, 2015 and Published as US 2015-0306140 on Oct. 29, 2015.
Bander et al., 1997, "MHC class I and II expression in prostate carcinoma and modulation by interferon-alpha and -gamma" Prostate. 3(4):233-239.
Boczkowski et al., 1996, "Dendritic cells pulsed with RNA are potent antigen-presenting cells in vitro and in vivo." J Exp Med. 84(2):465-472.
Gilboa et al., 1998, "Immunotherapy of cancer with dendritic-cell-based vaccines." Cancer Immunol Immunother. 46(2):82-87.
Kugler et al., 2003, Retraction: Regression of human metastatic renal cell carcinoma after vaccination with tumor cell-dendritic cell hybrids. Nat Med. 9(9):1221 (Retracted article).
Lutz et al., 1994, "Ricciardi-Castagnoli P. Retroviral immortalization of phagocytic and dendritic cell clones as a tool to investigate functional heterogeneity." J Immunol Methods. 174(1-2):269-279.
Maldonado-López et al., 1999, "CD8alpha+ and CD8alpha− subclasses of dendritic cells direct the development of distinct T helper cells in vivo." J Exp Med. 189 (3):587-592.
Martin et al., 2003, "Antigen-specific suppression of a primed immune response by dendritic cells mediated by regulatory T cells secreting interleukin-10." Immunity. 18(1):155-167.
Medzhitov and Janeway, 1997, "Innate immunity: impact on the adaptive immune response." Curr Opin Immunol. 9 (1):4-9.
Nair et al., 1996, "Cells treated with TAP-2 antisense oligonucleotides are potent antigen-presenting cells in vitro and in vivo." J Immunol. 156(5):1772-1780.
Nair et al., 1997, "Antigen-presenting cells pulsed with unfractionated tumor-derived peptides are potent tumor vaccines." Eur J Immunol. 27(3):589-597.
Nair SK. 1998, "Immunotherapy of cancer with dendritic cell-based vaccines." Gene Ther. 5(11):1445-1446.
O'Sullivan and Thomas, 2002, "CD40 ligation conditions dendritic cell antigen-presenting function through sustained activation of NF-kappaB." J Immunol. 168(11):5491-5498.
Ouaaz et al., 2002, "Dendritic cell development and survival require distinct NF-kappaB subunits. Immunity." 16(2):257-270.
Pettit et al., 1997, "Nuclear localization of RelB is associated with effective antigen-presenting cell function." J Immunol. 159(8):3681-3691.
Pirtskhalaishvili et al., 2000, "Transduction of dendritic cells with Bcl-xL increases their resistance to prostate cancer-induced apoptosis and antitumor effect in mice." J Immunol. 165(4):1956-1964.
Pound et al., 1997, "Prostate-specific antigen after anatomic radical retropubic prostatectomy. Patterns of recurrence and cancer control." Urol Clin North Am. 24(2):395-406.
Pound et al., 1999, "Natural history of progression after PSA elevation following radical prostatectomy." JAMA. 281(17):1591-1597.
Pulendran et al., 1999, "Distinct dendritic cell subsets differentially regulate the class of immune response in vivo." Proc Natl Acad Sci U S A. 96(3):1036-1041.
Pützer et al., 1997, "Interleukin 12 and B7-1 costimulatory molecule expressed by an adenovirus vector act synergistically to facilitate tumor regression." Proc Natl Acad Sci U S A. 94(20):10889-10894.
Rissoan et al., 1999, "Reciprocal control of T helper cell and dendritic cell differentiation." Science. 283(5405):1183-1186.
Shariat et al., 2001, "Adenovirus-mediated transfer of inducible caspases: a novel "death switch" gene therapeutic approach to prostate cancer." Cancer Res. 61(6):2562-2571.

(56) References Cited

OTHER PUBLICATIONS

Simons et al., 1999, "Induction of immunity to prostate cancer antigens: results of a clinical trial of vaccination with irradiated autologous prostate tumor cells engineered to secrete granulocyte-macrophage colony-stimulating factor using ex vivo gene transfer." Cancer Res. 59(20):5160-5168.
Slovin et al., 1998, "Immunological approaches for the treatment of prostate cancer." Semin Urol Oncol. 16(1):53-59.
Tamura et al., 1997, "Immunotherapy of tumors with autologous tumor-derived heat shock protein preparations." Science. 278(5335):117-120.
Tang and Cyster, 1999, "Chemokine Up-regulation and activated T cell attraction by maturing dendritic cells." Science. 284(5415):819-822.
Tartour and Fridman, 2000, "Cancer vaccines 2000." Immunol Lett. 74(1):1-3.
Tjoa and Murphy, 2000, "Development of dendritic-cell based prostate cancer vaccine." Immunol Lett 74(1):87-93.
Ullrich and Schlessinger, 1990, "Signal transduction by receptors with tyrosine kinase activity." Cell. 61(2):203-212.
Xie X, et al., 2001, "Robust prostate-specific expression for targeted gene therapy based on the human kallikrein 2 promoter." Hum Gene Ther. 12 (5):549-561.

\* cited by examiner

INDUCED ACTIVATION IN DENDRITIC CELLS

CROSS-REFERENCE TO RELATED APPLICATIONS

This application is a continuation application of U.S. patent application Ser. No. 14/643,989, filed Mar. 10, 2015, and entitled INDUCED ACTIVATION IN DENDRITIC CELLS, naming David Spencer, Brent Hanks, and Kevin Slawin as inventors, issued as U.S. Pat. No. 9,572,835, which is a continuation application of U.S. patent application Ser. No. 13/786,339, filed Mar. 5, 2013, and entitled INDUCED ACTIVATION IN DENDRITIC CELLS, naming David Spencer, Brent Hanks, and Kevin Slawin as inventors, issued as U.S. Pat. No. 8,999,949, which is a continuation application of U.S. patent application Ser. No. 12/165,360, filed Jun. 30, 2008, and entitled INDUCED ACTIVATION IN DENDRITIC CELLS, naming David Spencer, Brent Hanks, and Kevin Slawin as inventors, issued as U.S. Pat. No. 8,771,671, which is a continuation application of U.S. patent application Ser. No. 10/781,384, filed on Feb. 18, 2004, and entitled INDUCED ACTIVATION IN DENDRITIC CELLS, naming David Spencer, Brent Hanks, and Kevin Slawin as inventors, issued as U.S. Pat. No. 7,404,950, which is a non-provisional patent application claiming priority to U.S. Provisional Application No. 60/448,046, filed Feb. 18, 2003, which are all referred to and all incorporated by reference herein in their entirety.

STATEMENT REGARDING FEDERALLY SPONSORED RESEARCH

This invention was made with government support under Grant No. PC010463 awarded by the Department of Defense. The government has certain rights in the invention.

SEQUENCE LISTING

This application incorporates by reference the computer readable "Sequence Listing" that was filed on Feb. 18, 2004, in U.S. patent application Ser. No. 10/781,384, filed Feb. 18, 2004.

TECHNICAL FIELD

The present invention is drawn to compositions and methods to enhance an immune response. More particularly, the composition is an inducible co-stimulatory polypeptide and is induced by ligand oligomerization.

BACKGROUND OF THE INVENTION

Dendritic cells (DC) are unique among antigen-presenting cells (APC) by virtue of their potent capacity to activate immunologically naive T cells (Steinman, 1991). DC express constitutively, or after maturation, several molecules that mediate physical interaction with and deliver activation signals to responding T cells. These include class I and class II MHC molecules CDSO (B7-1) and CD86 (B7-2); CD40; CD11a/CD18 (LFA-1); and CD54 (ICAM-1) (Steinman, 1991; Steinman et al., 1995). DC also secrete, upon stimulation, several T cell-stimulatory cytokines, including IL-1-beta, IL-6, IL-8, macrophage-inflammatory protein-1-alpha (MIP-1-alpha), and MIP-1-delta (Matsue et al., 1992; Kitajima et al., 1995; Ariizumi et al., 1995; Caux et al., 1994; Heufler et al., 1992; Schreiber et al., 1992; Enk et al., 1992; Mohamadzadeh et al., 1996). Both of these properties, adhesion molecule expression and cytokine production are shared by other APC (e.g., activated macrophages and B cells), which are substantially less competent in activating naive T cells.

T cell activation is an important step in the protective immunity against pathogenic microorganisms (e.g., viruses, bacteria, and parasites), foreign proteins, and harmful chemicals in the environment. T cells express receptors on their surfaces (i.e., T cell receptors) that recognize antigens presented on the surface of antigen-presenting cells. During a normal immune response, binding of these antigens to the T cell receptor initiates intracellular changes leading to T cell activation. DC express several different adhesion (and co-stimulatory) molecules, which mediate their interaction with T cells. The combinations of receptors (on DC) and counter-receptors (on T cells) that are known to play this role include: a) class I MHC and CD8, b) class II MHC and CD4, c) CD54 (ICAM-1) and CD11 a/CD18 (LFA-1), d) ICAM-3 and CD11a/CD18, e) LFA-3 and CD2, f) CD80 (B7-1) and CD28 (and CTLA4), g) CD86 (B7-2) and CD28 (and CTLA4) and h) CD40 and CD40L (Steinman et al., 1995). Importantly, not only does ligation of these molecules promote physical binding between DC and T cells, it also transduces activation signals.

The dendritic cell (DC) orchestrates several critical steps in the development of an adaptive immune response. DCs communicate information regarding the antigenic state of the peripheral tissues to the local lymph nodes. Upon detection of both pathogen-derived and endogenous "danger signals", the DC physiologically adapts to its microenvironment by undergoing a genetic program known as "maturation" in order to direct an effective T cell response. The unique machinery of the DC allows it, not only to induce the activation of naïve T cells, but also to regulate their subsequent phenotype and function. These impressive attributes make the DC an ideal choice for their exploitation as natural adjuvants in cancer vaccine development. However, the limited successes of recent clinical trials indicate that current DC therapeutic strategies are in need of further refinement if DC immunotherapy is to be included in the cancer treatment arsenal alongside the more traditional modalities of chemo- and radiotherapy. This translation of DC vaccine development into the clinic will rely significantly upon advancements in our understanding of basic DC biology.

One of the critical deficiencies of DC-based vaccines is their transient nature. The activation state and the longevity of DCs are significantly limited. Less than 24 hours following exposure to bacteria-derived lipopolysaccharide (LPS), DCs terminate synthesis of the IL-12 cytokine and become refractory to further stimuli. This implies that the cytotoxic T lymphocyte (CTL) activation potential of DCs is severely compromised a relatively short time following its activation. Vaccine studies indicate that the survival of antigen-pulsed DCs within the draining lymph node is dramatically reduced 48 hours following their delivery and undetectable by 72 hours. These findings justify the need for alternative strategies for DC vaccine design, such as the development of genetically altered DCs that can circumvent physiological regulatory mechanisms and exhibit enhanced immunostimulatory properties for the treatment of cancer and other diseases.

BRIEF SUMMARY OF THE INVENTION

The present invention is directed to a composition and method that induces and/or activates antigen-presenting cells. The activated antigen-presenting cells can be used to enhance and/or regulate immune responses to a target antigen. More particularly, the present invention is drawn to compositions that are based on dendritic cells modified in vivo or ex vivo to express an inducible form of a co-stimulatory polypeptide molecule. The compositions of the present invention can be used to bolster the immune response of an immunocompromised subject, such as an HIV-infected subject. In certain embodiments, the present invention utilizes the power of CID to dimerize the co-stimulatory polypeptide.

Certain embodiments of the present invention include an expression construct comprising a polynucleotide promoter sequence, a polynucleotide sequence encoding a co-stimulatory polypeptide and a polynucleotide sequence encoding a ligand-binding region, all operatively linked. It is envisioned that the expression construct is comprised within a vector forming an expression vector; the vector is selected from the group consisting of a viral vector, a bacterial vector and a mammalian vector. Co-stimulatory polypeptides include, but are not limited to Pattern Recognition Receptors, C-reactive protein receptors (i.e., Nod1, Nod2, PtX3-R), TNF receptor (i.e., CD40, RANK/TRANCE-R, OX40, 4-1BB), and HSP receptors (Lox-1 and CD-91). In certain embodiments of the present invention, the expression construct and/or expression vector can be administered to a subject to ehance an immune response in the subject or bolster the immune response in the subject.

The expression construct may further include a second ligand-binding region, in which the ligand-binding region is a small molecule-binding domain, for example a FKBP binding domain. Yet further, the expression vector further comprises a polynucleotide sequence encoding a membrane targeting sequence, for example myristoylation-targeting sequence. In certain embodiments, the polynucleotide promoter sequence is selected from the group consisting a constitutive promoter (i.e., simian virus 40 (SV40) early promoter, a mouse mammary tumor virus promoter, a human immunodeficiency virus long terminal repeat promoter, a Moloney virus promoter, an avian leukemia virus promoter, an Epstein-Barr virus immediate early promoter, a Rous sarcoma virus promoter, a human action promoter, a human myosin promoter, a human hemoglobin promoter, cytomegalovirus (CMV) promoter, an EF1-alpha promoter, and a human muscle creatine promoter) an inducible promoter (i.e., metallothionein promoter, a glucocorticoid promoter, a progesterone promoter, and a tetracycline promoter) and a tissue specific promoter (i.e., dendritic cell (i.e., CD11c), PSA associated promoter or prostate-specific glandular kallikrein).

Other embodiments of the present invention comprise a transduced cell, in which the cell is transduced with the expression vector and/or expression construct of the present invention. More specifically, the cell is an antigen-presenting cell or an embryonic stem cell. It is contemplated that the transduced cell can be a pharmaceutical composition.

Other embodiments of the present invention include a fusion cell comprising a transduced antigen-presenting cell fused to a cell, wherein the transduced antigen-presenting cell comprises an expression vector and/or expression construct. More specifically, the cell is a tumor cell, for example a prostate tumor cell. It is contemplated that the fusion cell can be a pharmaceutical composition.

Another embodiment of the present invention is a pharmaceutical composition comprising the expression vector or expression construct and a pharmaceutically acceptable carrier, wherein said expression vector comprises a polynucleotide promoter sequence, a first polynucleotide sequence encoding a ligand-binding region, a second polynucleotide sequence encoding a ligand-binding region, a membrane-targeting sequence, and a polynucleotide sequence encoding a co-stimulatory polypeptide, all operatively linked.

Further embodiments of the present invention comprise a method of activating an antigen-presenting cell comprising the step of transducing the antigen-presenting cell with an expression vector, wherein the expression vector comprises a polynucleotide promoter sequence, a polynucleotide sequence encoding a ligand-binding region, and a polynucleotide sequence encoding a co-stimulatory polypeptide, all operatively linked; and activating the transduced antigen-presenting cell with ligand resulting in oligomerization. The co-stimulatory polypeptide includes, but is not limited to Pattern Recognition Receptors, C-reactive protein receptors (i.e., Nod1, Nod2, PtX3-R), TNF receptor (i.e., CD40, RANK/TRANCE-R, OX40, 4-1BB), and HSP receptors (Lox-1 and CD-91). More specifically, the co-stimulatory polypeptide is a CD40 cytoplasmic domain.

A further embodiment of the present invention comprises a method of modulating an immune response in a subject comprising the step of administering to the subject an expression vector of the present invention. The expression vector is expressed in dendritic cells and the vector comprises a polynucleotide promoter sequence, a polynucleotide sequence encoding a ligand-binding region, and a polynucleotide sequence encoding a co-stimulatory polypeptide, all operatively linked. The subject in whom the expression vector can be administered can be a subject that is immunocompromised.

Another embodiment comprises a method of modulating an immune response in a subject comprising the steps of: transducing an antigen-presenting cell with an expression vector, wherein the expression vector comprises a polynucleotide promoter sequence, a polynucleotide sequence encoding a ligand-binding region, and a polynucleotide sequence encoding a co-stimulatory polypeptide, all operatively linked; and administering to the subject transduced antigen-presenting cells, wherein the transduced antigen-presenting cells enhance the immune response in the subject. The transduced antigen-presenting cell is activated by administering a ligand that results in oligomerization. It is further envisioned that the transduced antigen present cells are administered to the subject simultaneously or subsequently to administration of an immunogenic composition.

Another embodiment of the present invention is a method of inducing a regulated immune response against an antigen in a subject comprising the steps of: transducing an antigen-presenting cell with an expression vector, wherein the expression vector comprising a polynucleotide promoter sequence, a polynucleotide sequence encoding a ligand-binding region, and a polynucleotide sequence encoding a co-stimulatory polypeptide, all operatively linked; loading transduced antigen-presenting cells with the antigen; administering transduced, loaded antigen-presenting cells to the subject thereby effecting a cytotoxic T lymphocyte and natural killer cell anti-tumor antigen immune response; and regulating the immune response induction directed toward tumor antigens with a ligand that results in oligomerization. The ligand is a protein or a non-protein. More particularly, the ligand is a non-protein, for example, a dimeric FK506 and/or dimeric FK506 analogs. The immune response is positively regulated by dimeric FK506 and/or dimeric FK506 analogs or is negatively regulated by monomeric FK506 and/or monomeric FK506 analogs. More specifically, the transduced, loaded antigen-presenting cells are administered to the subject intradermally, subcutaneously, intranodally or intralymphatically. It is envisioned that the antigen-presenting cells are transduced with the expression vector in vitro or ex vivo prior to administering to the subject.

Loading the antigen-presenting cells with an antigen can be accomplished utilizing standard methods, for example, pulsing, transducing, transfecting, and/or electrofusing. It is envisioned that the antigen can be nucleic acids (DNA or RNA), proteins, protein lysate, whole cell lysate, or antigen proteins linked to other proteins, i.e., heat shock proteins.

The antigens can be derived or isolated from a pathogenic microorganism such as viruses including HIV, influenza, Herpes simplex, human papilloma virus, Hepatitis B, Hepatitis C, EBV, Cytomegalovirus (CMV) and the like. The antigen may be derived or isolated from pathogenic bacteria such as from *Chlamydia, Mycobacteria, Legionella, Meningiococcus*, Group A *Streptococcus, Salmonella, Listeria, Hemophilus influenzae*, and the like. Still further, the antigen may be derived or isolated from pathogenic yeast including *Aspergillus*, invasive *Candida, Nocardia, Histoplasmosis, Cryptosporidia* and the like. The antigen may be derived or isolated from a pathogenic protozoan and pathogenic parasites including, but not limited to *Pneumocystis carinii, Trypanosoma, Leishmania, Plasmodium and Toxoplasma gondii*.

In certain embodiments, the antigen includes an antigen associated with a preneoplastic or hyperplastic state. Antigens may also be associated with, or causative of cancer. Such antigens are tumor specific antigen, tumor associated antigen (TAA) or tissue specific antigen, epitope thereof, and epitope agonist thereof. Such antigens include but are not limited to carcinoembryonic antigen (CEA) and epitopes thereof such as CAP-1, CAP-1-6D (46) and the like, MART-1, MAGE-1, MAGE-3, GAGE, GP-100, MUC-1, MUC-2, point mutated ras oncogene, normal and point mutated p53 oncogenes, PSMA, tyrosinase, TRP-1 (gp75), NY-ESO-1, TRP-2, TAG72, KSA, CA-125, PSA, HER-2/neu/c-erb/B2, BRC-I, BRC-II, bcr-abl, pax3-fkhr, ews-fli-1, modifications of TAAs and tissue specific antigen, splice variants of TAAs, epitope agonists, and the like.

Another embodiment is a method of treating and/or preventing a disease and/or disorder comprising administering to a subject an effective amount of an expression vector to treat and/or prevent the disease and/or disorder, wherein the expression vector comprises a polynucleotide promoter sequence, a polynucleotide sequence encoding a ligand-binding region, a second polynucleotide sequence encoding a ligand-binding region, a polynucleotide sequence encoding a membrane-targeting sequence, and a polynucleotide sequence encoding a co-stimulatory polypeptide, all operatively linked. The co-stimulatory polypeptide is a CD40 cytoplasmic domain.

In certain embodiments, the disease is a hyperproliferative disease, which can also be further defined as cancer. In still further embodiments, the cancer is melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder. The cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In other embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

Yet further, another embodiment is a method of treating a disease and/or disorder comprising administering to a subject an effective amount of a transduced antigen-presenting cell to treat the disease and/or disorder, wherein the transduced antigen-presenting cell is transduced with an expression vector comprising a polynucleotide promoter sequence, a first polynucleotide sequence encoding a ligand-binding region, a second polynucleotide sequence encoding a ligand-binding region, a polynucleotide sequence encoding a membrane-targeting sequence, and a polynucleotide sequence encoding a co-stimulatory polypeptide, all operatively linked. The co-stimulatory polypeptide is a member of the TNF Receptor family, more specifically; the co-stimulatory polypeptide is a CD40 cytoplasmic domain. The transduced antigen-presenting cells are administered to the subject intradermally, subcutaneously, or intranodally. The antigen-presenting cells are transduced with the expression vector in vitro prior to administering to the subject. The method may further comprise electrofusing the transduced antigen-presenting cell to a tumor cell. In certain embodiments, the tumor cell is a prostate tumor cell. The tumor cell is syngeneic, or allogeneic. The method may also further comprises transfecting the transduced antigen-presenting cell with tumor cell mRNA and/or pulsing the transduced antigen-presenting cell with tumor cell protein lysates and/or pulsing the transduced antigen-presenting cell with heat shock proteins linked to tumor cell polypeptides.

Another embodiment is a method of treating a subject with cancer comprising administering to the patient an effective amount of a transduced antigen-presenting cell to treat the cancer, wherein the transduced antigen-presenting cell is transduced with an expression vector comprising a polynucleotide promoter sequence, a first polynucleotide sequence encoding a ligand-binding region, a second polynucleotide sequence encoding a ligand-binding region, a polynucleotide sequence encoding a myristoylation-targeting sequence, and a polynucleotide sequence encoding a co-stimulatory polypeptide, all operatively linked; and administering at least one other anticancer treatment. The anticancer treatment is selected from the group consisting of chemotherapy, immunotherapy, surgery, radiotherapy, gene therapy and biotherapy.

Another embodiment is a transgenic mouse having incorporated into its genome an expression vector comprising a polynucleotide promoter sequence, a polynucleotide sequence encoding a CD40 cytoplasmic domain and a polynucleotide sequence encoding a ligand-binding region, all operatively linked. The ligand-binding region is a FKBP binding domain. The expression vector may further comprise a second ligand-binding region, whish is FKBP binding domain. Still further, the vector may comprise a polynucleotide sequence encoding a myristoylation-targeting sequence. The polynucleotide promoter sequence comprises CD11c. Embryonic stem cells and/or antigen-presenting cells may be isolated from the transgenic mouse.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

FIG. 1A is a schematic of endogenous CD40. FIG. 1B is a schematic of a Chemically Induced Dimerization System (CID) that utilizes a lipid-permeable organic dimerizer drug (AP20187) that binds with high affinity to drug binding domains. FIG. 1C provides a graph, a photograph of a Western blotl, and a schematic of a DNA construct for an NFκB-SEAP Reporter Assay in Jurkat TAg Cells.

FIG. 2A is a photograph of an anti-HA Western Blot Analysis of iCD40 D2SC/1 DC Clones. FIG. 2B is a photograph of anti-HA Immunofluorescence of D2SC/1.Hi (lt) and D2SC/1 (rt) FIG. 2C is a graph of results of an NFκB-SEAP Reporter Assay. FIG. 2D is a graph of results and a photograph that show induction of RelB and Sp1 in D2SC/1.Hi by AP20187. FIG. 2E is a graph of results and a photograph of results of assays where maximum concentrations of each agent (based on titrations) were co-incubated with iCD40 D2SC/1 for 24 hrs and nuclear lysates were analyzed by western blot. FIG. 2F is a photograph of results of pulse chase experiments that shows kinetics of RelB activation by iCD40 or other indicated treatments.

FIG. 3A provides graphs of flow cytometry of activation markers on D2SC/1 treated with control, AP20187, LPS, iCD40 expression, iCD40+AP20187. FIG. 3B is a graph of the reduction of phagocytosis of FITC-dextran after treatment with LPS or iCD40. FIG. 3C provides graphs and FACs sorting results showing activation of bulk lymph node cells or purified CD8 T cells by treated D2SC/1 cells.

FIG. 4A is a schema of iCD40.D2SC/1-based vaccines. FIG. 4B is a graph of results where iCD40.D2SC/1 cells were prepared for injection by in vitro LPS or iCD40 treatment, by in vivo iCD40 signaling, or by both in vitro and in vivo iCD40 signaling. After 10 days, splenocytes were isolated and assayed for antigen-specific proliferation. FIG. 4C provides a graph and FACs sorting results showing peptide epitope specificity, the percent of $K^d$LLO-specific T cells from vaccinated or control mice was calculated using tetramer staining. FIG. 4D is a graph of CTL activity from splenocytes of mice vaccinated with β-gal pulsed DCs treated as above using standard 5-day assay using β-gal expressing target cells. FIG. 4E is a graph and a schematic showing CTL activity assayed on LLO-expressing tumor cells (construct shown).

FIG. 5A is a Western blot (α-HA) of primary DCs infected with AD-iCD40-GFP. FIG. 5B provides flow cytometry analysis of transduced DCs. FIG. 5C provides two graphs and flow cytometry analysis of $K^b$, B7.2 and endogenous CD40 on iCD40-stimulated DCs. FIG. 5D provides a graph showing kinetics of IL-12 induction (ELISA) by iCD40 and LPS. FIG. 5E provides two graphs showing survival kinetics of DCs following CD40L or iCD40 stimulation.

FIG. 6A, which is a graph, and FIG. 6C, which provides FACs sorting analysis, show co-injection of an iCD40-expressing plasmid enhances antigen-specific CD8+ T cell Responses. iCD40 was subcloned into a PCMV-driven bicistronic vector co-expressing hrGFP. Gold micro-particles were coated with plasmid DNA encoding the SIINFEKL minigene, the iCD40-hrGFP construct, or both. DNA micro-particles were injected into mice in the abdomen (2×) and in each ear using a helium gene gun. DNA doses were kept constant at 2.5 μg per shot or 10 μg per mouse. AP20187 was injected i.p. 20 hours later into some groups. Spleens were harvested 12 days later and analyzed by two color flow analysis using PE-KbSIINFEKL tetramer/FITC-anti-CD8 staining. FIG. 6B is a graph that shows in vivo drug delivery enhances CD8+ T cell Activation. Splenocytes harvested above were co-incubated with 10 μg/mL SIINFEKL peptide overnight and analyzed for dual CD8+CD69+ surface expression by flow cytometry. Only viable cells were gated.

FIG. 7A provides two graphs showing the activation of CD8+ T cells and FIG. 7B is a chart or data showing the activation of (CD69+) CD8+ T cells following vaccination.

FIG. 8A provides two graphs showing endocytosis inhibition reduces CD40 downregulation. D2SC/1 cell lines were incubated with 250 μM cytochalasin B for 1 hour followed by a 30 min CD40L treatment. D2SC/1 cells were also treated with cytochalasin B, the DMSO solvent control, and CD40L alone. $K^+$-depletion of the D2SC/1 cell line was also carried out prior to CD40 surface staining and flow cytometry analysis. Only viable cells were gated for analysis. FIG. 8B provides flow cytometry analysis showing inhibition of lysosomal degradation enhances intracellular CD40 levels. D2SC/1 cell lines were incubated with 0.5 μM bafilomycin A inhibitor for 1 hour followed by intracellular staining for CD40 (Total CD40). Total CD40 is compared to surface CD40 fluorescence. FIG. 8C is a graph showing inhibition of endocytosis intensifies the CD40 activation signal in DC Lines. Staining and analysis of surface H-$2K^d$.

FIG. 9A is a schematic of Type I, II, and iCD40. FIG. 9B is a photograph of a Western blot showing IICD40-expressing DC lines do not express reduced levels of iCD40. The type II CD40 isoform was rt-PCR amplified from purified BMDCs, subcloned into a pEF-1α-driven myc-tagged ZeoR vector, and transfected into iCD40-expressing D2SC/1 cells. Double clonal stable lines were generated by G418/zeocin selection and limiting dilution. Resulting lines were screened for IICD40 expression by anti-myc western blot and analyzed for iCD40 expression by anti-HA western blots. FIG. 9C is a graph showing that Type II CD40 down-regulates surface expression of Type I CD40 in DC Lines. Empty vector control and IICD40-expressing D2SC/1 lines were analyzed for their surface expression of CD40 by flow cytometry. Only viable cells were gated for analysis. FIG. 9D provides two graphs showing the Type II CD40 isoform downmodulates Type I CD40 signaling, but not iCD40 signaling. iCD40-IICD40-expressing D2SC/1 cell lines were cultured in the presence of increasing concentrations of CD40L and the AP20187 drug followed by surface staining and flow analysis of H-2$K^d$.

DETAILED DESCRIPTION OF THE INVENTION

Figure 1A:
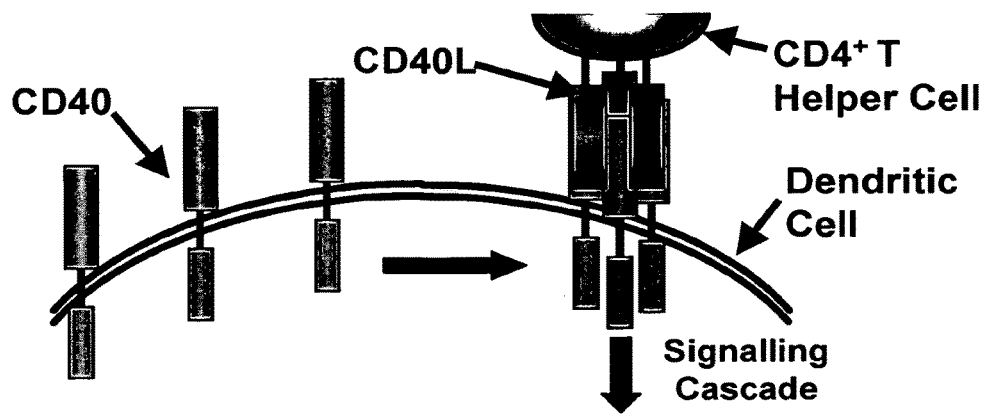
FIG. 1A-FIG. 1C show the chemically induced dimerization of CD40.

It is readily apparent to one skilled in the art that various embodiments and modifications can be made to the invention disclosed in this Application without departing from the scope and spirit of the invention.

I. Definitions

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "allogeneic" as used herein, refers to cell types or tissues that are antigenically distinct. Thus, cells or tissue transferred from the same species can be antigenically distinct.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates. Exemplary organisms include but are not limited to, *Helicobacters, Campylobacters, Clostridia, Corynebacterium diphtheriae, Bordetella pertussis*, influenza virus, parainfluenza viruses, respiratory syncytial virus, *Borrelia burgdorfei, Plasmodium*, herpes simplex viruses, human immunodeficiency virus, papillomavirus, *Vibrio cholera, E. coli*, measles virus, rotavirus, shigella, *Salmonella typhi, Neisseria gonorrhea*. Therefore, a skilled artisan realizes that any macromolecule, including virtually all proteins or peptides, can serve as antigens. Furthermore, antigens can be derived from recombinant or genomic DNA. A skilled artisan realizes that any DNA, which contains nucleotide sequences or partial nucleotide sequences of a pathogenic genome or a gene or a fragment of a gene for a protein that elicits an immune response results in synthesis of an antigen. Furthermore, one skilled in the art realizes that the present invention is not limited to the use of the entire nucleic acid sequence of a gene or genome. It is readily inherent that the present invention includes, but is not limited to, the use of partial nucleic acid sequences of more than one gene or genome and that these nucleic acid sequences are arranged in various combinations to elicit the desired immune response.

The term "antigen-presenting cell" is any of a variety of cells capable of displaying, acquiring, or presenting at least one antigen or antigenic fragment on (or at) its cell surface. In general, the term "antigen-presenting cell" can be any cell that accomplishes the goal of the invention by aiding the enhancement of an immune response (i.e., from the T-cell or -B-cell cell arms of the immune system) against an antigen or antigenic composition. Such cells can be defined by those of skill in the art, using methods disclosed herein and in the art. As is understood by one of ordinary skill in the art (see for example Kuby, 1993, incorporated herein by reference), and used herein certain embodiments, a cell that displays or presents an antigen normally or preferentially with a class II major histocompatibility molecule or complex to an immune cell is an "antigen-presenting cell." In certain aspects, a cell (e.g., an APC cell) may be fused with another cell, such as a recombinant cell or a tumor cell that expresses the desired antigen. Methods for preparing a fusion of two or more cells is well known in the art, such as for example, the methods disclosed in Goding, pp. 65-66, 71-74 1986; Campbell, pp. 75-83, 1984; Kohler and Milstein, 1975; Kohler and Milstein, 1976, Gefter et al., 1977, each incorporated herein by reference. In some cases, the immune cell to which an antigen-presenting cell displays or presents an antigen to is a CD4+TH cell. Additional molecules expressed on the APC or other immune cells may aid or improve the enhancement of an immune response. Secreted or soluble molecules, such as for example, cytokines and adjuvants, may also aid or enhance the immune response against an antigen. Such molecules are well known to one of skill in the art, and various examples are described herein.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "iCD40 molecule" is defined as an inducible CD40. This iCD40 can bypass mechanisms that extinguish endogenous CD40 signaling. The term "iCD40" embraces "iCD40 nucleic acids", "iCD40 polypeptides" and/or iCD40 expression vectors. Yet further, it is understood the activity of iCD40 as used herein is driven by CID.

As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There are times when the full or partial genomic sequence is preferred, such as where the non-coding regions are required for optimal expression or where non-coding regions such as introns are to be targeted in an antisense strategy.

The term ""dendritic cell" (DC) is an antigen presenting cell existing in vivo, in vitro, ex vivo, or in a host or subject, or which can be derived from a hematopoietic stem cell or a monocyte. Dendritic cells and their precursors can be isolated from a variety of lymphoid organs, e.g., spleen, lymph nodes, as well as from bone marrow and peripheral blood. The DC has a characteristic morphology with thin sheets (lamellipodia) extending in multiple directions away from the dendritic cell body. Typically, dendritic cells express high levels of MHC and costimulatory (e.g., B7-1 and B7-2) molecules. Dendritic cells can induce antigen specific differentiation of T cells in vitro, and are able to initiate primary T cell responses in vitro and in vivo.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. In the present invention, the term "therapeutic construct" may also be used to refer to the expression construct or transgene. One skilled in the art realizes that the present invention utilizes the expression construct or transgene as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra.

As used herein, the term "ex vivo" refers to "outside" the body. One of skill in the art is aware that ex vivo and in vitro can be used interchangeably.

As used herein, the term "functionally equivalent", refers to CD40 nucleic acid fragment, variant, or analog, refers to a nucleic acid that codes for a CD40 polypeptide that stimulates an immune response to destroy tumors or hyperproliferative disease. Preferably "functionally equivalent" refers to an CD40 polypeptide that is lacking the extracellular domain, but is capable of amplifying the T cell-mediated tumor killing response by upregulating dendritic cell expression of antigen presentation molecules.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

As used herein, the term "gene" is defined as a functional protein, polypeptide, or peptide-encoding unit. As will be understood by those in the art, this functional term includes genomic sequences, cDNA sequences, and smaller engineered gene segments that express, or is adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

The term "immunocompromised" as used herein is defined as a subject that has reduced or weakened immune system. The immunocompromised condition may be due to a defect or dysfunction of the immune system or to other factors that heighten susceptibility to infection and/or disease. Although such a categorization allows a conceptual basis for evaluation, immunocompromised individuals often do not fit completely into one group or the other. More than one defect in the body's defense mechanisms may be affected. For example, individuals with a specific T-lymphocyte defect caused by HIV may also have neutropenia caused by drugs used for antiviral therapy or be immunocompromised because of a breach of the integrity of the skin and mucous membranes. An immunocompromised state can result from indwelling central lines or other types of impairment due to intravenous drug abuse; or be caused by secondary malignancy, malnutrition, or having been infected with other infectious agents such as tuberculosis or sexually transmitted diseases, e.g., syphilis or hepatitis.

As used herein, the term "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

As used herein, the term "polynucleotide" is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, one skilled in the art is cognizant that polynucleotides include mutations of the polynucleotides, include but are not limited to, mutation of the nucleotides, or nucleosides by methods well known in the art.

As used herein, the term "polypeptide" is defined as a chain of amino acid residues, usually having a defined sequence. As used herein the term polypeptide is interchangeable with the terms "peptides" and "proteins".

As used herein, the term "promoter" is defined as a DNA sequence recognized by the synthetic machinery of the cell, or introduced synthetic machinery, required to initiate the specific transcription of a gene.

As used herein, the term "regulate an immune response" or "modulate an immune response" refers to the ability to modify the immune response. For example, the composition of the present invention is capable of enhancing and/or activating the immune response. Still further, the composition of the present invention is also capable of inhibiting the immune response. The form of regulation is determined by the ligand that is used with the composition of the present invention. For example, a dimeric analog of the chemical results in dimerization of the co-stimulatory polypeptide leading to activation of the DCs, however, a monomeric analog of the chemical does not result in dimerization of the co-stimulatory polypeptide, which would not activate the DCs.

The term "transfection" and "transduction" are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like.

As used herein, the term "syngeneic" refers to cells, tissues or animals that have genotypes. For example, identical twins or animals of the same inbred strain. Syngeneic and isogeneic can be used interchangeable.

The term "subject" as used herein includes, but is not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, the term "under transcriptional control" or "operatively linked" is defined as the promoter is in the correct location and orientation in relation to the nucleic acid to control RNA polymerase initiation and expression of the gene.

As used herein, the terms "treatment", "treat", "treated", or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e. g., reduce or eliminate the infection or prevent it from becoming worse.

As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a subject, the vaccine is able to provoke an immune response including, but not limited to, the production of antibodies, cytokines and/or other cellular responses.

II. Dendritic Cells

The innate immune system uses a set of germline-encoded receptors for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism (Janeway et al., 1989; Medzhitov et al., 1997).

The receptors of the innate immune system that recognize PAMPs are called Pattern Recognition Receptors (PRRs) (Janeway et al., 1989; Medzhitov et al., 1997). These receptors vary in structure and belong to several different protein families. Some of these receptors recognize PAMPs directly (e.g., CD14, DEC205, collectins), while others (e.g., complement receptors) recognize the products generated by PAMP recognition. Members of these receptor families can, generally, be divided into three types: 1) humoral receptors circulating in the plasma; 2) endocytic receptors expressed on immune-cell surfaces, and 3) signaling receptors that can be expressed either on the cell surface or intracellularly (Medzhitov et al., 1997; Fearon et al., 1996).

Cellular PRRs are expressed on effector cells of the innate immune system, including cells that function as professional antigen-presenting cells (APC) in adaptive immunity. Such effector cells include, but are not limited to, macrophages, dendritic cells, B lymphocytes and surface epithelia. This expression profile allows PRRs to directly induce innate effector mechanisms, and also to alert the host organism to the presence of infectious agents by inducing the expression of a set of endogenous signals, such as inflammatory cytokines and chemokines, as discussed below. This latter function allows efficient mobilization of effector forces to combat the invaders.

The primary function of dendritic cells (DCs) is to acquire antigen in the peripheral tissues, travel to secondary lymphoid tissue, and present antigen to effector T cells of the immune system (Banchereau, et al., 2000; Banchereau, et al., 1998). As DCs carry out their crucial role in the immune response, they undergo maturational changes allowing them to perform the appropriate function for each environment (Termeer, C. C. et al., 2000). During DC maturation, antigen uptake potential is lost, the surface density of major histocompatibility complex (MHC) class I and class II molecules increases by 10-100 fold, and CD40, costimulatory and adhesion molecule expression also greatly increases (Lanzavecchia, A. et al., 2000). In addition, other genetic alterations permit the DCs to home to the T cell-rich paracortex of draining lymph nodes and to express T-cell chemokines that attract naive and memory T cells and prime antigen-specific naïve THO cells (Adema, G. J. et al., 1997). During this stage, mature DCs present antigen via their MHC II molecules to CD4+ T helper cells, inducing the upregulation of T cell CD40 ligand (CD40L) that, in turn, engages the DC CD40 receptor. This DC:T cell interaction induces rapid expression of additional DC molecules that are crucial for the initiation of a potent CD8+ cytotoxic T lymphocyte (CTL) response, including further upregulation of MHC I and II molecules, adhesion molecules, costimulatory molecules (e.g., B7.1,B7.2), cytokines (e.g., IL-12) and anti-apoptotic proteins (e.g., Bcl-2) (Anderson, D. M., et al., 1997; Caux, C., et al., 1997; Ohshima, Y., et al., 1997; Sallusto, F., et al., 1998). CD8+ T cells exit lymph nodes, reenter circulation and home to the original site of inflammation to destroy pathogens or malignant cells.

One key parameter influencing the function of DCs is the CD40 receptor, serving as the "on switch" for DCs (Bennett, S. R. et al., 1998; Clark, S. R. et al., 2000; Fernandez, N. C., et al., 1999; Ridge, J. P. et al., 1998; Schoenberger, S. P., et al., 1998). CD40 is a 48-kDa transmembrane member of the TNF receptor superfamily (McWhirter, S. M., et al., 1999). CD40-CD40L interaction induces CD40 trimerization, necessary for initiating signaling cascades involving TNF receptor associated factors (TRAFs) (Ni, C. Z., et al., 2000; Pullen, S. S. et al., 1999). CD40 uses these signaling molecules to activate several transcription factors in DCs, including NFκB, AP-1, STAT3, and p38MAPK (McWhirter, S. M., et al., 1999).

The present invention contemplates a novel DC activation system based on recruiting signaling molecules or co-stimulatory polypeptides to the plasmid membrane of the DCs resulting in prolonged/increased activation and/or survival in the DCs. Co-stimulatory polypeptides include any molecule or polypeptide that activates the NFκB pathway, Akt pathway, and/or p38 pathway. The DC activation system is based upon utilizing a recombinant signaling molecule fused to a ligand-binding domains (i.e., a small molecule binding domain) in which the co-stimulatory polypeptide is activated and/or regulated with a ligand resulting in oligomerization (i.e., a lipid-permeable, organic, dimerizing drug). Other systems that may be used to crosslink or oligomerization of co-stimulatory polypeptides include antibodies, natural ligands, and/or artificial cross-reacting or synthetic ligands. Yet further, other dimerization systems contemplated include the coumermycin/DNA gyrase B system.

Co-stimulatory polypeptides that can be used in the present invention include those that activate NFκB and other variable signaling cascades for example the p38 pathway and/or Akt pathway. Such co-stimulatory polypeptides include, but are not limited to Pattern Recognition Receptors, C-reactive protein receptors (i.e., Nod1, Nod2, PtX3-R), TNF receptors (i.e., CD40, RANK/TRANCE-R, OX40, 4-1BB), and HSP receptors (Lox-1 and CD-91).

Pattern Recognition Receptors include, but are not limited to endocytic pattern-recognition receptors (i.e., mannose receptors, scavenger receptors (i.e., Mac-1, LRP, peptidoglycan, techoic acids, toxins, CD11c/CR4)); external signal pattern-recognition receptors (Toll-like receptors (TLR1, TLR2, TLR3, TLR4, TLR5, TLR6, TLR7, TLR8, TLR9, TLR10), peptidoglycan recognition protein, (PGRPs bind bacterial peptidoglycan, and CD14); and internal signal pattern-recognition receptors (i.e., NOD-receptors 1 & 2).

III. Engineering Expression Constructs

The present invention involves an expression construct encoding a co-stimulatory polypeptide and a ligand-binding domain, all operatively linked. More particularly, more than one ligand-binding domain is used in the expression construct. Yet further, the expression construct contains a membrane-targeting sequence. One with skill in the art realizes that appropriate expression constructs may include a co-stimulatory polypeptide element on either side of the above FKBP ligand-binding elements. The expression construct of the present invention may be inserted into a vector, for example a viral vector or plasmid.

A. Co-Stimulatory Polypeptides

In the present invention, co-stimulatory polypeptide molecules are capable of amplifying the T-cell-mediate response by upregulating dendritic cell expression of antigen presentation molecules. Co-stimulatory proteins that are contemplated in the present invention include, for example, but are not limited to the members of tumor necrosis factor (TNF) family (i.e., CD40, RANK/TRANCE-R, OX40, 4-1B), Toll-like receptors, C-reactive protein receptors, Pattern Recognition Receptors, and HSP receptors. Typically, the cytoplasmic domains from these co-stimulatory polypeptides are used in the expression vector. The cytoplasmic domain from one of the various co-stimulatory polypeptides, including mutants thereof, where the recognition sequence involved in initiating transcription associated with the cytoplasmic domain is known or a gene responsive to such sequence is known.

In specific embodiments of the present invention, the co-stimulatory polypeptide molecule is CD40. The CD40 molecule comprises a nucleic acid molecule which: (1) hybridizes under stringent conditions to a nucleic acid having the sequence of a known CD40 gene and (2) codes for an CD40 polypeptide. Preferably the CD40 polypeptide is lacking the extracellular domain. It is contemplated that other normal or mutant variants of CD40 can be used in the present invention. Exemplary polynucleotide sequences that encode CD40 polypeptides include, but are not limited to SEQ.ID.NO: 1 and CD40 isoforms from other species.

In certain embodiments, the present invention involves the manipulation of genetic material to produce expression constructs that encode an inducible form of CD40 (iCD40). Such methods involve the generation of expression constructs containing, for example, a heterologous nucleic acid sequence encoding CD40 cytoplasmic domain and a means for its expression, replicating the vector in an appropriate helper cell, obtaining viral particles produced therefrom, and infecting cells with the recombinant virus particles.

Thus, the preferable CD40 molecule of the present invention lacks the extracellular domain. In specific embodiments, the extracellular domain is truncated or removed. It is also contemplated that the extracellular domain can be mutated using standard mutagenesis, insertions, deletions, or substitutions to produce an CD40 molecule that does not have a functional extracellular domain. The preferred CD40 nucleic acid has the nucleic acid sequence of SEQ.ID.NO. 2. The CD40 nucleic acids of the invention also include homologs and alleles of a nucleic acid having the sequence of SEQ.ID.NO. 2, as well as, functionally equivalent fragments, variants, and analogs of the foregoing nucleic acids.

In the context of gene therapy, the gene will be a heterologous polynucleotide sequence derived from a source other than the viral genome, which provides the backbone of the vector. The gene is derived from a prokaryotic or eukaryotic source such as a bacterium, a virus, yeast, a parasite, a plant, or even an animal. The heterologous DNA also is derived from more than one source, i.e., a multigene construct or a fusion protein. The heterologous DNA also may include a regulatory sequence, which is derived from one source and the gene from a different source.

B. Ligand-Binding Domains

The ligand-binding ("dimerization") domain of the expression construct of this invention can be any convenient domain that will allow for induction using a natural or unnatural ligand, preferably an unnatural synthetic ligand. The ligand-binding domain can be internal or external to the cellular membrane, depending upon the nature of the construct and the choice of ligand. A wide variety of ligand-binding proteins, including receptors, are known, including ligand-binding proteins associated with the cytoplasmic regions indicated above. As used herein the term "ligand-binding domain can be interchangeable with the term "receptor". Of particular interest are ligand-binding proteins for which ligands (preferably small organic ligands) are known or may be readily produced. These ligand-binding domains or receptors include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like.

For the most part, the ligand-binding domains or receptor domains will be at least about 50 amino acids, and fewer than about 350 amino acids, usually fewer than 200 amino acids, either as the natural domain or truncated active portion thereof. Preferably the binding domain will be small (<25 kDa, to allow efficient transfection in viral vectors), monomeric (this rules out the avidin-biotin system), nonimmunogenic, and should have synthetically accessible, cell permeable, nontoxic ligands that can be configured for dimerization.

The receptor domain can be intracellular or extracellular depending upon the design of the expression construct and the availability of an appropriate ligand. For hydrophobic ligands, the binding domain can be on either side of the membrane, but for hydrophilic ligands, particularly protein ligands, the binding domain will usually be external to the cell membrane, unless there is a transport system for internalizing the ligand in a form in which it is available for binding. For an intracellular receptor, the construct can encode a signal peptide and transmembrane domain 5' or 3' of the receptor domain sequence or by having a lipid attachment signal sequence 5' of the receptor domain sequence. Where the receptor domain is between the signal peptide and the transmembrane domain, the receptor domain will be extracellular.

The portion of the expression construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding.

Antibodies and antibody subunits, e.g., heavy or light chain, particularly fragments, more particularly all or part of the variable region, or fusions of heavy and light chain to create high-affinity binding, can be used as the binding domain. Antibodies that are contemplated in the present invention include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen).

Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

C. Oligomerization

The transduced signal will normally result from ligand-mediated oligomerization of the chimeric protein molecules, i.e., as a result of oligomerization following ligand-binding, although other binding events, for example allosteric activation, can be employed to initiate a signal. The construct of the chimeric protein will vary as to the order of the various domains and the number of repeats of an individual domain.

For multimerizing the receptor, the ligand for the ligand-binding domains/receptor domains of the chimeric surface membrane proteins will usually be multimeric in the sense that it will have at least two binding sites, with each of the binding sites capable of binding to the receptor domain. Desirably, the subject ligands will be a dimer or higher order oligomer, usually not greater than about tetrameric, of small synthetic organic molecules, the individual molecules typically being at least about 150 D and fewer than about 5 kDa, usually fewer than about 3 kDa. A variety of pairs of synthetic ligands and receptors can be employed. For example, in embodiments involving natural receptors, dimeric FK506 can be used with an FKBP receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used. For embodiments involving unnatural receptors, e.g., antibody subunits, modified antibody subunits or modified receptors and the like, any of a large variety of compounds can be used. A significant characteristic of these ligand units is that they bind the receptor with high affinity and are able to be dimerized chemically.

In certain embodiments, the present invention utilizes the technique of chemically induced dimerization (CID) to produce a conditionally controlled protein or polypeptide. In addition to this technique being inducible, it also is reversible, due to the degradation of the labile dimerizing agent or administration of a monomeric competitive inhibitor.

CID system uses synthetic bivalent ligands to rapidly crosslink signaling molecules that are fused to ligand-binding domains CID. This system has been used to trigger the oligomerization and activation of cell surface (Spencer et al., 1993; Spencer et al., 1996; Blau et al., 1997), or cytosolic proteins (Luo et al., 1996; MacCorkle et al., 1998), the recruitment of transcription factors to DNA elements to modulate transcription (Ho et al., 1996; Rivera et al., 1996) or the recruitment of signaling molecules to the plasma membrane to stimulate signaling (Spencer et al., 1995; Holsinger et al., 1995).

The CID system is based upon the notion that surface receptor aggregation effectively activates downstream signaling cascades. In the simplest embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs and a myristoylation sequence to the cytoplasmic signaling domain of a target receptor, one can stimulate signaling in a dimerizer drug-dependent, but ligand and ectodomain-independent manner. This provides the system with temporal control, reversibility using monomeric drug analogs, and enhanced specificity. The high affinity of third-generation AP20187/AP1903 CIDs for their binding domain, FKBP12 permits specific activation of the recombinant receptor in vivo without the induction of non-specific side effects through endogenous FKBP12. In addition, the synthetic ligands are resistant to protease degradation, making them more efficient at activating receptors in vivo than most delivered protein agents.

The ligands used in the present invention are capable of binding to two or more of the ligand-binding domains. One skilled in the art realizes that the chimeric proteins may be able to bind to more than one ligand when they contain more than one ligand-binding domain. The ligand is typically a non-protein or a chemical. Exemplary ligands include, but are not limited to dimeric FK506 (e.g., FK1012).

Since the mechanism of CD40 activation is fundamentally based on trimerization, this receptor is particularly amenable to the CID system. CID regulation provides the system with 1) temporal control, 2) reversibility by addition of a non-active monomer upon signs of an autoimmune reaction, and 3) limited potential for non-specific side effects. In addition, inducible in vivo DC CD40 activation would circumvent the requirement of a second "danger" signal normally required for complete induction of CD40 signaling and would potentially promote DC survival in situ allowing for enhanced T cell priming. Thus, engineering DC vaccines to express iCD40 amplifies the T cell-mediated killing response by upregulating DC expression of antigen presentation molecules, adhesion molecules, TH1 promoting cytokines, and pro-survival factors.

Other dimerization systems contemplated include the coumermycin/DNA gyrase B system. Coumermycin-induced dimerization activates a modified Raf protein and stimulates the MAP kinase cascade. See Farrar et al., 1996.

D. Membrane-Targeting

A membrane-targeting sequence provides for transport of the chimeric protein to the cell surface membrane, where the same or other sequences can encode binding of the chimeric protein to the cell surface membrane. Any membrane-targeting sequence can be employed that is functional in the host and may, or may not, be associated with one of the other domains of the chimeric protein. Such sequences include, but are not limited to myristoylation-targeting sequence, palmitoylation targeting sequence, prenylation sequences (i.e., farnesylation, geranyl-geranylation, CAAX Box) or transmembrane sequences (utilizing signal peptides) from receptors.

E. Selectable Markers

In certain embodiments of the invention, the expression constructs of the present invention contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) are employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, βgal or chloramphenicol acetyltransferase (CAT).

F. Control Regions

1. Promoters

The particular promoter employed to control the expression of a polynucleotide sequence of interest is not believed to be important, so long as it is capable of directing the expression of the polynucleotide in the targeted cell. Thus, where a human cell is targeted, it is preferable to position the polynucleotide sequence-coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene products are toxic (add in more inducible promoters).

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

Similarly tissue specific promoters are used to effect transcription in specific tissues or cells so as to reduce potential toxicity or undesirable effects to non-targeted tissues. For example, promoters such as the PSA associated promoter or prostate-specific glandular kallikrein.

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitrypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 anti-chymotrypsin.

It is envisioned that any of the above promoters alone or in combination with another can be useful according to the present invention depending on the action desired. In addition, this list of promoters should not be construed to be exhaustive or limiting, those of skill in the art will know of other promoters that are used in conjunction with the promoters and methods disclosed herein.

2. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Any promoter/enhancer combination (as per the Eukaryotic Promoter Data Base EPDB) can be used to drive expression of the gene. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence is employed such as human or bovine growth hormone and SV40 polyadenylation signals. Also contemplated as an element of the expression cassette is a terminator. These elements can serve to enhance message levels and to minimize read through from the cassette into other sequences.

4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be in-frame with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements is used to create multigene, or polycistronic messages. IRES elements are able to bypass the ribosome-scanning model of 5' methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

IV. Methods of Gene Transfer

In order to mediate the effect of the transgene expression in a cell, it will be necessary to transfer the expression constructs of the present invention into a cell. Such transfer may employ viral or non-viral methods of gene transfer. This section provides a discussion of methods and compositions of gene transfer.

A transformed cell comprising an expression vector is generated by introducing into the cell the expression vector. Suitable methods for polynucleotide delivery for transformation of an organelle, a cell, a tissue or an organism for use with the current invention include virtually any method by which a polynucleotide (e.g., DNA) can be introduced into an organelle, a cell, a tissue or an organism, as described herein or as would be known to one of ordinary skill in the art.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials. In specific embodiments, the host cell is a dendritic cell, which is an antigen-presenting cell.

It is well within the knowledge and skill of a skilled artisan to determine an appropriate host. Generally this is based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, COS, CHO, Saos, and PC12. Examples of yeast strains include, but are not limited to, YPH499, YPH500 and YPH501.

A. Non-Viral Transfer

1. Ex vivo Transformation

Methods for transfecting vascular cells and tissues removed from an organism in an ex vivo setting are known to those of skill in the art. For example, canine endothelial cells have been genetically altered by retroviral gene transfer in vitro and transplanted into a canine (Wilson et al., 1989). In another example, Yucatan minipig endothelial cells were transfected by retrovirus in vitro and transplanted into an artery using a double-balloon catheter (Nabel et al., 1989). Thus, it is contemplated that cells or tissues may be removed and transfected ex vivo using the polynucleotides of the present invention. In particular aspects, the transplanted cells or tissues may be placed into an organism. Thus, it is well within the knowledge of one skilled in the art to isolate dendritic cells from an animal, transfect the cells with the expression vector and then administer the transfected or transformed cells back to the animal.

2. Injection

In certain embodiments, a polynucleotide may be delivered to an organelle, a cell, a tissue or an organism via one or more injections (i.e., a needle injection), such as, for example, subcutaneously, intradermally, intramuscularly, intravenously, intraperitoneally, etc. Methods of injection of vaccines are well known to those of ordinary skill in the art (e.g., injection of a composition comprising a saline solution). Further embodiments of the present invention include the introduction of a polynucleotide by direct microinjection. The amount of the expression vector used may vary upon the nature of the antigen as well as the organelle, cell, tissue or organism used.

Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair must be clipped in order to observe proper needle placement). Intranodal injection allows for direct delivery of antigen to lymphoid tissues. Intralymphatic injection allows direct administration of DCs.

3. Electroporation

In certain embodiments of the present invention, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

4. Calcium Phosphate

In other embodiments of the present invention, a polynucleotide is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

5. DEAE-Dextran

In another embodiment, a polynucleotide is delivered into a cell using DEAE-dextran followed by polyethylene glycol. In this manner, reporter plasmids were introduced into mouse myeloma and erythroleukemia cells (Gopal, 1985).

6. Sonication Loading

Additional embodiments of the present invention include the introduction of a polynucleotide by direct sonic loading. LTK-fibroblasts have been transfected with the thymidine kinase gene by sonication loading (Fechheimer et al., 1987).

7. Liposome-Mediated Transfection

In a further embodiment of the invention, a polynucleotide may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a polynucleotide complexed with Lipofectamine (Gibco BRL) or Superfect (Qiagen).

8. Receptor Mediated Transfection

Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a polynucleotide-binding agent. Others comprise a cell receptor-specific ligand to which the polynucleotide to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand is chosen to correspond to a receptor specifically expressed on the target cell population.

In other embodiments, a polynucleotide delivery vehicle component of a cell-specific polynucleotide-targeting vehicle may comprise a specific binding ligand in combination with a liposome. The polynucleotide(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which will preferably comprise one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

9. Microprojectile Bombardment

Microprojectile bombardment techniques can be used to introduce a polynucleotide into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

B. Viral Vector-Mediated Transfer

In certain embodiments, transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsulation is localized between 194-385 bp (0.5-1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity should be achieved.

2. Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

3. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1995 ; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996).

AAV-mediated efficient gene transfer and expression in the lung has led to clinical trials for the treatment of cystic fibrosis (Carter and Flotte, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

4. Other Viral Vectors

Other viral vectors are employed as expression constructs in the present invention. Vectors derived from viruses such as vaccinia virus (Ridgeway, 1988; Baichwal and Sugden, 1986; Coupar et al., 1988) canary pox virus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

V. Enhancement of an Immune Response

In certain embodiments, the present invention contemplates a novel DC activation strategy that incorporates the manipulation of signaling co-stimulatory polypeptides that activate NFκB pathways, Akt pathways, and/or p38 pathways. This DC activation system can be used in conjunction with or without standard vaccines to enhance the immune response since it replaces the requirement for CD4+ T cell help during APC activation (Bennett S. R. et al., 1998; Ridge, J. P. et al., 1998; Schoenberger, S. P., et al., 1998). Thus, the DC activation system of the present invention enhances immune responses by circumventing the need for the generation of MHC class II-specific peptides.

In specific embodiments, the DC activation is via CD40 activation. Thus, DC activation via endogenous CD40/CD40L interactions may be subject to downregulation due to negative feedback, leading rapidly to the "IL-12 burn-out effect". Within 7 to 10 hours after CD40 activation, an alternatively spliced isoform of CD40 (type II) is produced as a secretable factor (Tone, M., et al., 2001). Type II CD40 may act as a dominant negative receptor, downregulating signaling through CD40L and potentially limiting the potency of the immune response generated. Therefore, the present invention co-opts the natural regulation of CD40 by creating an inducible form of CD40 (iCD40), lacking the extracellular domain and activated instead by synthetic dimerizing ligands (Spencer, D. M. et al., 1993) through a technology termed chemically induced dimerization (CID).

The present invention comprises a method of enhancing the immune response in an subject comprising the step of administering either the expression vector, expression construct or transduced antigen-presenting cells of the present invention to the subject. The expression vector of the present invention encodes a co-stimulatory polypeptide, such as iCD40.

In certain embodiments the antigen-presenting cells are comprised in an animal, such as human, non-human primate, cow, horse, pig, sheep, goat, dog, cat, or rodent. The subject is a human, more preferably, a patient suffering from an infectious disease, and/or a subject that is immunocompromised, or is suffering from a hyperproliferative disease.

In further embodiments of the present invention, the expression construct and/or expression vector can be utilized as a composition or substance that activates antigen-presenting cells. Such a composition that "activates antigen-presenting cells" or "enhances the activity antigen-presenting cells" refers to the ability to stimulate one or more activities associated with antigen-presenting cells. Such activities are well known by those of skill in the art. For example, a composition, such as the expression construct or vector of the present invention, can stimulate upregulation of co-stimulatory molecules on antigen presenting cells, induce nuclear translocation of NF-κB in antigen presenting cells, activate toll-like receptors in antigen presenting cells, or other activities involving cytokines or chemokines.

An amount of a composition that activates antigen-presenting cells which "enhances" an immune response refers to an amount in which an immune response is observed that is greater or intensified or deviated in any way with the addition of the composition when compared to the same immune response measured without the addition of the composition. For example, the lytic activity of cytotoxic T cells can be measured, e.g., using a $^{51}$Cr release assay, with and without the composition. The amount of the substance at which the CTL lytic activity is enhanced as compared to the CTL lytic activity without the composition is said to be an amount sufficient to enhance the immune response of the animal to the antigen. In a preferred embodiment, the immune response in enhanced by a factor of at least about 2, more preferably by a factor of about 3 or more. The amount of cytokines secreted may also be altered.

The enhanced immune response may be an active or a passive immune response. Alternatively, the response may be part of an adaptive immunotherapy approach in which antigen-presenting cells are obtained with from a subject (e.g., a patient), then transduced with a composition comprising the expression vector or construct of the present invention. The antigen-presenting cells may be obtained from the blood of the subject or bone marrow of the subject. In certain preferred embodiments, the antigen-presenting cells are isolated from the bone marrow. In a preferred embodiment, the antigen-presenting cells are administered to the same or different animal (e.g., same or different donors). In a preferred embodiment, the subject (e.g., a patient) has or is suspected of having a cancer, such as for example, prostate cancer, or has or is suspected of having an infectious disease. In other embodiments the method of enhancing the immune response is practiced in conjunction with a known cancer therapy or any known therapy to treat the infectious disease.

The expression construct, expression vector and/or transduced antigen-presenting cells can enhance or contribute to the effectiveness of a vaccine by, for example, enhancing the immunogenicity of weaker antigens such as highly purified or recombinant antigens, reducing the amount of antigen required for an immune response, reducing the frequency of immunization required to provide protective immunity, improve the efficacy of vaccines in subjects with reduced or weakened immune responses, such as newborns, the aged, and immunocompromised individuals, and enhance the immunity at a target tissue, such as mucosal immunity, or promote cell-mediated or humoral immunity by eliciting a particular cytokine profile.

Yet further, an immunocompromised individual or subject is a subject that has a reduced or weakened immune response. Such individuals may also include a subject that has undergone chemotherapy or any other therapy resulting in a weakened immune system, a transplant recipient, a subject currently taking immunosuppressants, an aging individual, or any individual that has a reduced and/or impaired CD4 T helper cells. It is contemplated that the present invention can be utilize to ehance the amount and/or activty of CD4 T helper cells in an immunocompromised subject.

In specific embodiments, prior to administering the transduced antigen-presenting cell, the cells are challenged with antigens (also referred herein as "target antigens"). After challenge, the transduced, loaded antigen-presenting cells are administered to the subject parenterally, intradermally, intranodally, or intralymphatically. Additional parenteral routes include, but are not limited to subcutaneous, intramuscular, intraperitoneal, intravenous, intraarterial, intramyocardial, transendocardial, transepicardial, intrathecal, and infusion techniques.

The target antigen, as used herein, is an antigen or immunological epitope on the antigen, which is crucial in immune recognition and ultimate elimination or control of the disease-causing agent or disease state in a mammal. The immune recognition may be cellular and/or humoral. In the case of intracellular pathogens and cancer, immune recognition is preferably a T lymphocyte response.

The target antigen may be derived or isolated from a pathogenic microorganism such as viruses including HIV, (Korber et al, 1977) influenza, Herpes simplex, human papilloma virus (U.S. Pat. No. 5,719,054), *Hepatitis B* (U.S. Pat. No. 5,780,036), *Hepatitis C* (U.S. Pat. No. 5,709,995), EBV, *Cytomegalovirus* (CMV) and the like. Target antigen may be derived or isolated from pathogenic bacteria such as from *Chlamydia* (U.S. Pat. No. 5,869,608), *Mycobacteria*, *Legionella, Meningiococcus*, Group A *Streptococcus, Salmonella, Listeria, Hemophilus influenzae* (U.S. Pat. No. 5,955,596) and the like.

Target antigen may be derived or isolated from pathogenic yeast including *Aspergillus*, invasive *Candida* (U.S. Pat. No. 5,645,992), *Nocardia, Histoplasmosis, Cryptosporidia* and the like.

Target antigen may be derived or isolated from a pathogenic protozoan and pathogenic parasites including but not limited to *Pneumocystis carinii, Trypanosoma, Leishmania* (U.S. Pat. No. 5,965,242), *Plasmodium* (U.S. Pat. No. 5,589,343) and *Toxoplasma gondii*.

Target antigen includes an antigen associated with a preneoplastic or hyperplastic state. Target antigen may also be associated with, or causative of cancer. Such target antigen may be tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-1, CAP-1-6D (46) and the like (GenBank Accession No. M29540), MART-1 (Kawakami et al, 1994), MAGE-1 (U.S. Pat. No. 5,750,395), MAGE-3, GAGE (U.S. Pat. No. 5,648,226), GP-100 (Kawakami et al., 1992), MUC-1, MUC-2, point mutated ras oncogene, normal and point mutated p53 oncogenes (Hollstein et al., 1994), PSMA (Israeli et al., 1993), tyrosinase (Kwon et al. 1987) TRP-1 (gp75) (Cohen et al., 1990; U.S. Pat. No. 5,840,839), NY-ESO-1 (Chen et al., PNAS 1997), TRP-2 (Jackson et al., 1992), TAG72, KSA, CA-125, PSA, HER-2/neu/c-erb/B2, (U.S. Pat. No. 5,550,214), BRC-I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each.

For organisms that contain a DNA genome, a gene encoding a target antigen or immunological epitope thereof of interest is isolated from the genomic DNA. For organisms with RNA genomes, the desired gene may be isolated from cDNA copies of the genome. If restriction maps of the genome are available, the DNA fragment that contains the gene of interest is cleaved by restriction endonuclease digestion by methods routine in the art. In instances where the desired gene has been previously cloned, the genes may be readily obtained from the available clones. Alternatively, if the DNA sequence of the gene is known, the gene can be synthesized by any of the conventional techniques for synthesis of deoxyribonucleic acids.

Genes encoding an antigen of interest can be amplified by cloning the gene into a bacterial host. For this purpose, various prokaryotic cloning vectors can be used. Examples are plasmids pBR322, pUC and pEMBL.

The genes encoding at least one target antigen or immunological epitope thereof can be prepared for insertion into the plasmid vectors designed for recombination with a virus by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the DNA vectors used for recombination with a virus, then purified prior to insertion into the vectors at restriction endonuclease cleavage sites (cloning sites).

Antigen loading of dendritic cells with antigens may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide. Antigens from cells or MHC molecules may be obtained by acid-elution or other methods known in the art (see Zitvogel et al., 1996).

One skilled in the art is fully aware that activation of the co-stimulatory molecule of the present invention relies upon oligomerization of ligand-binding domains, for example CID, to induce its activity. In specific embodiments, the ligand is a non-protein. More specifically, the ligand is a dimeric FK506 or dimeric FK506 analogs, which result in enhancement or positive regulation of the immune response. The use of monomeric FK506 or monomeric FK506 analogs results in inhibition or reduction in the immune response negatively.

T-lymphocytes are activated by contact with the antigen-presenting cell that comprises the expression vector of the present invention and has been challenged, transfected, pulsed, or electrofused with an antigen.

Electrofusing in the present invention is a method of generating hybrid cells. There are several advantages in producing cell hybrids by electrofusion. For example, fusion parameters can be easily and accurately electronically controlled to conditions depending on the cells to be fused. Further, electrofusion of cells has shown to the ability to increase fusion efficiency over that of fusion by chemical means or via biological fusogens. Electrofusion is performed by applying electric pulses to cells in suspension. By exposing cells to an alternating electric field, cells are brought close to each other in forming pearl chains in a process termed dielectrophoresis alignment. Subsequent higher voltage pulses cause cells to come into closer contact, reversible electropores are formed in reversibly permeabilizing and mechanically breaking down cell membranes, resulting in fusion.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a naïve CD8 T cell that recognizes an antigen-MHC complex proliferates and differentiates into an effector cell called a cytotoxic CD8 T lymphocyte (CTL). CTLs eliminate cells of the body displaying antigen, such as virus-infected cells and tumor cells, by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemaglutinin-stimulated IL-2 expanded cell line established from PBMC (Bernard et al., 1998) or by T cells isolated from a previously immunized subject and restimulated for 6 days with DC infected with an adenovirus vector containing antigen using standard 4 h $^{51}$Cr release microtoxicity assays. One type of assay uses cloned T-cells. Cloned T-cells have been tested for their ability to mediate both perforin and Fas ligand-dependent killing in redirected cytotoxicity assays (Simpson et al., 1998). The cloned cytotoxic T lymphocytes displayed both Fas- and perforin-dependent killing. Recently, an in vitro dehydrogenase release assay has been developed that takes advantage of a new fluorescent amplification system (Page et al., 1998). This approach is sensitive, rapid, and reproducible and may be used advantageously for mixed lymphocyte reaction (MLR). It may easily be further automated for large-scale cytotoxicity testing using cell membrane integrity, and is thus considered in the present invention. In another fluorometric assay developed for detecting cell-mediated cytotoxicity, the fluorophore used is the non-toxic molecule AlamarBlue (Nociari et al., 1998). The AlamarBlue is fluorescently quenched (i.e., low quantum yield) until mitochondrial reduction occurs, which then results in a dramatic increase in the AlamarBlue fluorescence intensity (i.e., increase in the quantum yield). This assay is reported to be extremely sensitive, specific and requires a significantly lower number of effector cells than the standard $^{51}$Cr release assay.

Other immune cells that are induced by the present invention include natural killer cells (NK). NKs are lymphoid cells that lack antigen-specific receptors and are part of the innate immune system. Typically, infected cells are usually destroyed by T cells alerted by foreign particles bound the cell surface MHC. However, virus-infected cells signal infection by expressing viral proteins that are recognized by antibodies. These cells can be killed by NKs. In tumor cells, if the tumor cells lose expression of MHC I molecules, then it may be susceptible to NKs.

In further embodiments, the transduced antigen-presenting cell is transfected with tumor cell mRNA. The transduced transfected antigen-presenting cell is administered to an animal to effect cytotoxic T lymphocytes and natural killer cell anti-tumor antigen immune response and regulated using dimeric FK506 and dimeric FK506 analogs. The tumor cell mRNA is mRNA from a prostate tumor cell.

Yet further, the transduced antigen-presenting cell is pulsed with tumor cell lysates. The pulsed transduced antigen-presenting cells are administered to an animal to effect cytotoxic T lymphocytes and natural killer cell anti-tumor antigen immune response and regulated using dimeric FK506 and dimeric FK506 analogs. The tumor cell lysates is a prostate tumor cell lysate.

VI. Formulations and Routes for Administration to Patients

Where clinical applications are contemplated, it will be necessary to prepare pharmaceutical compositions—expression constructs, expression vectors, fused proteins, transduced cells, activated DCs, transduced and loaded DCs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For oral administration, the compositions of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

VII. Methods for Treating a Disease

The present invention also encompasses methods of treatment or prevention of a disease caused by pathogenic microorganisms and/or a hyperproliferative disease.

Diseases may be treated or prevented by use of the present invention include diseases caused by viruses, bacteria, yeast, parasites, protozoa, cancer cells and the like. The pharmaceutical composition of the present invention (transduced DCs, expression vector, expression construct, etc.) of the present invention may be used as a generalized immune enhancer (DC activating composition or system) and as such has utility in treating diseases. Exemplary disease that can be treated and/or prevented utilizing the pharmaceutical composition of the present invention include, but are not limited to infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

Preneoplastic or hyperplastic states which may be treated or prevented using the pharmaceutical composition of the present invention (transduced DCs, expression vector, expression construct, etc.) of the present invention include but are not limited to preneoplastic or hyperplastic states such as colon polyps, Crohn's disease, ulcerative colitis, breast lesions and the like.

Cancers which may be treated using the pharmaceutical composition of the present invention of the present invention include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases that may be treated using DC activation system of the present invention include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In the method of treatment, the administration of the pharmaceutical composition (expression construct, expression vector, fused protein, transduced cells, activated DCs, transduced and loaded DCs) of the invention may be for either "prophylactic" or "therapeutic" purpose. When provided prophylactically, the pharmaceutical composition of the present invention is provided in advance of any symptom. The prophylactic administration of pharmaceutical composition serves to prevent or ameliorate any subsequent infection or disease. When provided therapeutically, the pharmaceutical composition is provided at or after the onset of a symptom of infection or disease. Thus the present invention may be provided either prior to the anticipated exposure to a disease-causing agent or disease state or after the initiation of the infection or disease.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the novel unit dose of an inoculum of this invention are dictated by and are dependent upon the unique characteristics of the pharmaceutical composition and the particular immunologic effect to be achieved.

An effective amount of the pharmaceutical composition would be the amount that achieves this selected result of enhancing the immune response, and such an amount could be determined as a matter of routine by a person skilled in the art. For example, an effective amount of for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

A. Genetic Based Therapies

Specifically, the present inventors intend to provide, to a cell, an expression construct capable of providing a co-stimulatory polypeptide, such as CD40 to the cell, such as an antigen-presenting cell and activating CD40. The lengthy discussion of expression vectors and the genetic elements employed therein is incorporated into this section by reference. Particularly preferred expression vectors are viral vectors such as adenovirus, adeno-associated virus, herpes virus, vaccinia virus and retrovirus. Also preferred is lysosomal-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

B. Cell Based Therapy

Another therapy that is contemplated is the administration of transduced antigen-presenting cells. The antigen-presenting cells may be transduced in vitro. Formulation as a pharmaceutically acceptable composition is discussed above.

In cell based therapies, the transduced antigen-presenting cells may be transfected with target antigen nucleic acids, such as mRNA or DNA or proteins; pulsed with cell lysates, proteins or nucleic acids; or electrofused with cells. The cells, proteins, cell lysates, or nucleic acid may derive from cells, such as tumor cells or other pathogenic microorganism, for example, viruses, bacteria, protozoa, etc.

C. Combination Therapies

In order to increase the effectiveness of the expression vector of the present invention, it may be desirable to combine these compositions and methods of the invention with an agent effective in the treatment of the disease.

In certain embodiments, anti-cancer agents may be used in combination with the present invention. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

In further embodiments antibiotics can be used in combination with the pharmaceutical composition of the present invention to treat and/or prevent an infectious disease. Such antibiotics include, but are not limited to, amikacin, aminoglycosides (e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixin defensins, prothionamide, pyrazinamide, pyrimethamine sulfadiazine, quinolones (e.g., ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with the expression vector effective to kill or inhibit proliferation of a cancer cell and/or microorganism. This process may involve contacting the cell(s) with an agent(s) and the pharmaceutical composition of the present invention at the same time or within a period of time wherein separate administration of the pharmaceutical composition of the present invention and an agent to a cell, tissue or organism produces a desired therapeutic benefit. This may be achieved by contacting the cell, tissue or organism with a single composition or pharmacological formulation that includes both the pharmaceutical composition of the present invention and one or more agents, or by contacting the cell with two or more distinct compositions or formulations, wherein one composition includes the pharmaceutical composition of the present invention and the other includes one or more agents.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be co-current with and/or follow the other agent(s) by intervals ranging from minutes to weeks. In embodiments where the pharmaceutical composition of the present invention, and other agent(s) are applied separately to a cell, tissue or organism, one would generally ensure that a significant period of time did not expire between the times of each delivery, such that the pharmaceutical composition of the present invention and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the pharmaceutical composition of the present invention. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition of the present invention and one or more agents may be employed.

VIII. Transgenic Animals

Detailed methods for generating non-human transgenic animal are described herein. Any non-human animal can be used in the methods described herein. Preferred mammals are rodents, e.g., rats or mice.

A transgenic mouse describes an mouse that has had genes from another organism inserted into its genome through recombinant DNA techniques. The transgenic mouse may contain material from an unrelated organism, such as from a virus, plant, or human. Thus, in an exemplary embodiment, the "transgenic non-human animals" of the invention are produced by introducing transgenes into the germline of the non-human animal.

Introduction of the transgene into the embryo can be accomplished by any means known in the art such as, for example, microinjection, electroporation, or lipofection. For example, the CD40 gene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is within the scope of this invention. One common method is to incubate the embryos in vitro for about 1-7 days, depending on the species, and then reimplant them into the surrogate host.

Embryonic target cells at various developmental stages can also be used to introduce transgenes. Different methods are used depending on the stage of development of the embryonic target cell. The specific line(s) of any animal used to practice this invention are selected for general good health, good embryo yields, good pronuclear visibility in the embryo, and good reproductive fitness. In addition, the haplotype is a significant factor.

Embryonic stem cells, sometimes referred to as ES cells, are derived from inner cell mass (ICM) of fertilized eggs in blastocyst phase, and can be cultured and maintained in vitro while being kept in an undifferentiated state. Embryonic stem cells are extremely useful biological materials for preparing transgenic animals. For example, a gene knockout mouse in which a specific gene is inactivated can be produced by replacing an active gene in an embryonic stem cell chromosome with an inactivated gene by means of a homologous recombination system.

The progeny of the transgenically manipulated embryos can be tested for the presence of the CD40 construct by Southern blot analysis of the segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals can be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity.

n certain embodiments of the invention, transgenic mice are produced which contain an expression vector comprising a polynucleotide promoter sequence, a polynucleotide sequence encoding a CD40 cytoplasmic domain and a polynucleotide sequence encoding a dimeric ligand-binding region, all operatively linked. These mice may be used to obtain antigen-presenting cells, such as dendritic cells, which express the CD40 cytoplasmic domain.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Development of Techniques for Efficient Isolation of DCs

Bone marrow from the tibias and femurs of C57BL/6 mice was cultured in RPMI supplemented with GM-CSF and IL-4 (Inaba, K. et al., 1992). Bone marrow cultures were maintained for a total of 6 days in 24 well plates while one-half of each well was replenished with fresh media and cytokines on day 3. On the final day of culture, cells were washed from the plates, co-incubated with anti-CD11c microbeads (Miltenyi Biotec, Bergisch Gladbach, Germany), and applied to two consecutive magnetic columns. Splenic DCs were subjected to microbead purification immediately following collagenase treatment of splenic tissue. Based on flow cytometry analysis, the DC purity of the final cell suspension was consistently >95% for bone marrow-derived DCs and >80% for splenic DCs.

EXAMPLE 2

Development of Techniques for Efficient Cellular Electrofusion

Two Jurkat T cell populations were individually stained with distinct lipophilic dyes, fluorescing at different wavelengths (DiI and DiO). These cell populations were mixed and fused using the BTX2001 electrofusion instrument at different D.C. voltages. Fusion efficiency was analyzed by flow cytometry. Electrofusion of Jurkat TAg cells using a 275 V D.C. generated viable hybrid yields of around 60%.

EXAMPLE 3

Construction of an Inducible CD40 Vector

Figure 1B:
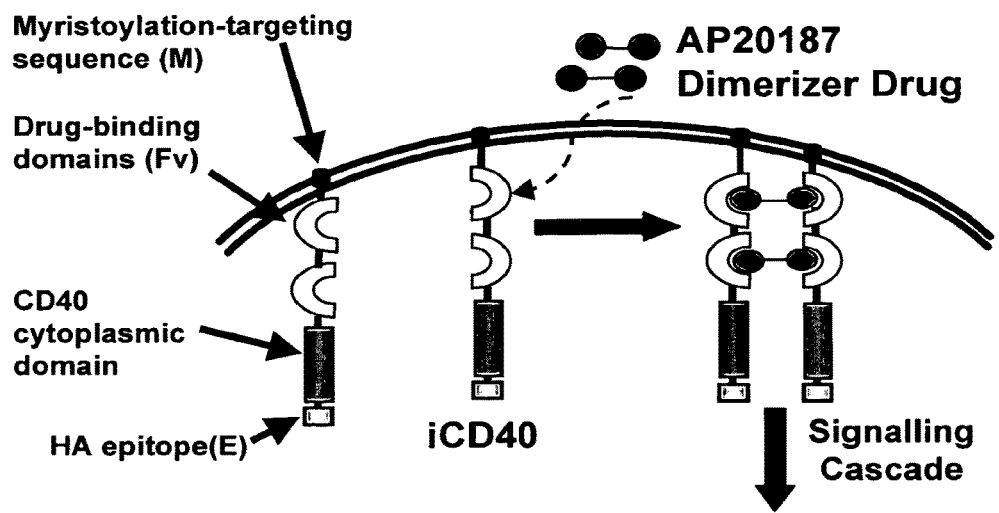
Figure 1C:
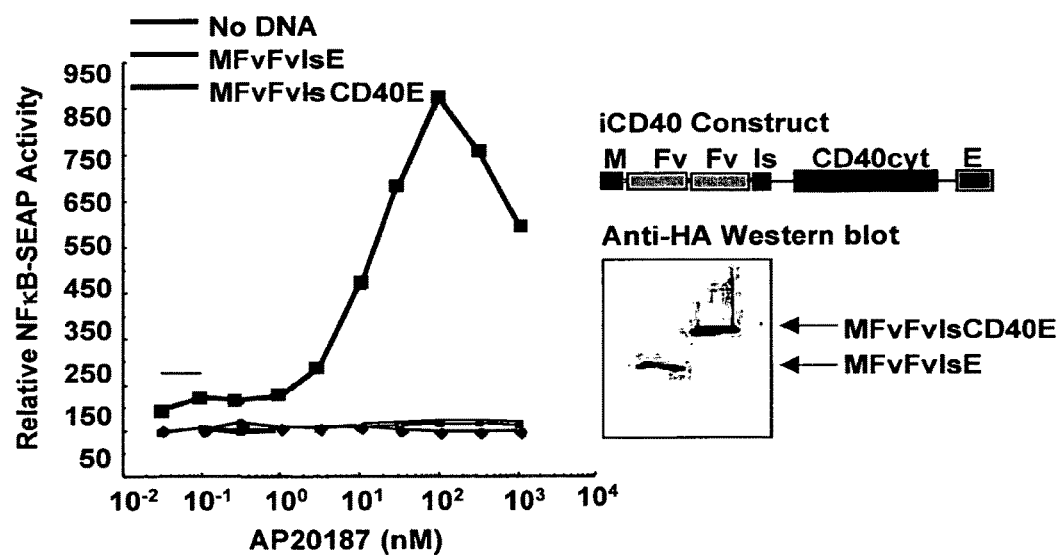

An inducible CD40 receptor based on chemical-induced dimerization (CID) and patterned after endogenous CD40 activation was produced to specifically target DCs (FIG. 1A). The recombinant CD40 receptor, termed iCD40, was engineered by rt-PCR amplifying the 228 bp CD40 cytoplasmic signaling domain from purified murine bone marrow-derived DCs (>95% CD11c+) and sub-cloning the resulting DNA fragment either downstream (i.e., M-FvFv-lsCD40-E) or upstream (M-CD40-FvFvls-E) of tandem copies of the dimerizing drug binding domain, FKBP12(V36) (FIG. 1B). Membrane localization was achieved with a myristoylation-targeting domain (M) and an HA epitope (E) tag was present for facile identification. To determine if the transcripts were capable of activating NFκB, the constructs were transiently transfected into Jurkat T cells and NFκB reporter assays were preformed in the presence of titrated dimerizer drug, AP20187 (FIG. 1C). FIG. 1C showed that increasing levels of AP20187 resulted in significant upregulation of NFκB transcriptional activity compared to the control vector, M-FvFvls-E, lacking CD40 sequence. Since the membrane-proximal version of iCD40, M-CD40-FvFvls-E, was less responsive to AP20187 in this assay system, the M-FvFvlsCD40-E construct was used in further studies, and heretofore referred to as "iCD40". This decision was reinforced by the crystallographic structure of the CD40 cytoplasmic tail, which reveals a hairpin conformation that could be deleteriously altered by the fusion of a heterologous protein to its carboxyl-terminus (Ni 2000). The data also showed high drug dose suppression over 100 nM, likely due to the saturation of drug binding domains. This same phenomenon has been observed in other cell types expressing limiting levels of the iCD40 receptor. These results suggested that iCD40 was capable of inducing CID-dependent nuclear translocation of the NFκB transcription factor.

Once the Ad-iCD40-GFP virus was demonstrated to successfully transduce 293T cells and to induce the expression of both iCD40 and GFP transgenes, bone marrow-derived dendritic cells were transduced with efficiencies ranging between 25-50% under serum-free conditions. The results have demonstrated that iCD40-expressing primary DCs exhibited an upregulation in maturation markers (e.g., CD86, CD40) and an enhanced ability to synthesize the IL-12 cytokine when treated with CID. In addition, CID-treated iCD40-expressing primary DCs survived longer in culture and were capable of inducing a more robust CTL response in vivo compared to non-transduced DC and Ad-GFP-transduced DC controls.

EXAMPLE 4

Cell Fusion

TRAMP-C2 murine prostate cancer cell line is cultured in high glucose media with insulin and DHT and with Cell Tracker Green Dye (CMFDA, Molecular Probes, Eugene, Oreg.). Isolated DCs that are stained with Cell Tracker Orange Dye (CMTMR, Molecular Probes, Eugene, Oreg.) are fused to g-irradiated TRAMP-C2 cells using the lab's BTX Electro-Cell Manipulator 2001 instrument (Genetronics, San Diego, Calif.), which applies an alternating current to dimerize cells at the center of an electrical field. A high voltage direct current pulse is then released which fuses the membranes of the dimerized cells, subjecting cells to harsh fusogenic conditions for shorter periods of time and producing higher hybrid yields than the standard polyethylene glycol fusion. Although irradiated, the hybrid cells survive for several days.

EXAMPLE 5

CTL/IFN-γ Assay

Splenocytes and 4-6 lymph nodes are incubated with mitomycin C-treated (and washed 8×) TRAMP-B7 cells (obtained from Jim Allison, UCB). After 7 days expanded/viable T cells are Ficoll-purified and stimulated with TRAMP-C2-B7 a second time. After 7 additional days, dilutions of TRAMP-C2 cells (pre-incubated for 2 days with 1 ng/ml IFNγ to boost MHC) are incubated with T cells and analyzed for de novo IFNγ production. Alternatively, target cells will be pre-loaded with $^{51}$Cr for true CTL assays.

EXAMPLE 6

Determine Whether iCD40 Activation in situ Can Increase Anti-Tumor Immunity

Cultured proliferating DCs are transduced with adenovirus expressing iCD40 and then fused with irradiated TRAMP-C2 cells, as before. For −6 h timepoints, DC:TRAMP heterokaryon are maintained in culture media supplemented with the dimerizer AP20187 for 6 hours prior to vaccine preparation and administration. For all other CID timepoints (0, 6, 12 and 24 h post-vaccination), dimerizer AP20187 are delivered to vaccinated and control mice by i.p. injection. An additional control group receives DC/iCD40:TRAMP hybrids but no CID. Two weeks after a booster vaccine, mice will be challenged with 2×10$^6$ s.c. TRAMP-C2 cells as before. The efficacy of iCD40 stimulation in situ versus in vitro is correlated with measurements of tumor incidence and size and by CTL assays after DC/iCD40:tumor vaccination in the presence or absence of CID.

EXAMPLE 7

Transfection of DCs with mRNAs from Tumor Cells

Using the methods of Gilboa and colleagues (Gilboa, et al., 1998; Boczkowski, D., et al., 1996), cDNAs made from TRAMP-C2 cells are amplified and subcloned into an expression vector. Following transcription in a reticulocyte lysate, mRNA is purified using a poly-T primer and magnetic bead separation. A number of lipid-based transfection protocols (e.g., FuGene6, Superfectin) are currently available, and the most effective method based on control transfections of freshly amplified DCs using a reporter plasmid are used.

EXAMPLE 8

Pulsing of DCs with Peptides from Rumor Cells

To increase the likelihood of transferring relevant tumor-derived peptides, capable of binding to MHC molecules, DCs are pulsed with peptides derived from TRAMP-C2 cells. Since MHC levels are extremely low on cultured TRAMP-derived cells, MHC levels on tumor cells are boosted using 5 ng/ml murine IFN-γ. MHC-derived peptides are purified using HPLC and acid-treated MHC using previously described methods (Nair, S. K. et al., 1997). Finally, DCs are initially treated with anti-sense against the TAP peptide transporter to increase the density of "empty" MHC on the surface as previously described (Nair, S. K. et al., 1996).

EXAMPLE 9

Pulsing of DCs with Other Antigens

Active specific immunotherapy using vaccines consisting of isolated murine tumor-derived HSPPC-96 was demonstrated against murine tumors (Tamura, Y. et al., 1997). The gp96 itself is non-polymorphic but acts as a chaperone for tightly bound immunogenic peptides, which are believed to represent the full cellular repertoire of immunogens. Thus, gp96 proteins are purified using an affinity column and used to prime DCs.

EXAMPLE 10 iCD40 Activates NFκB in DCs

Figure 2A:
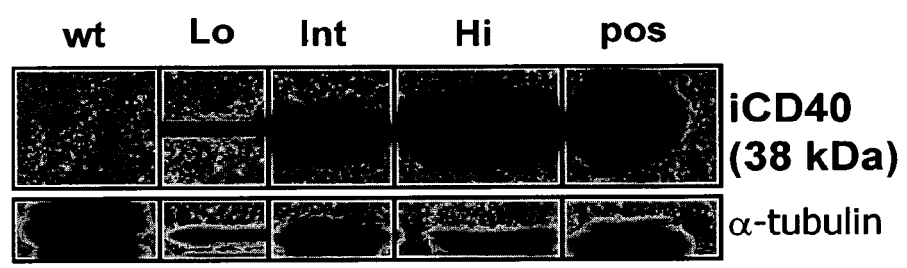
FIG. 2A-FIG. 2F show inducible CD40 initiates a potent NFkB signal in DCs.
Figure 2B:
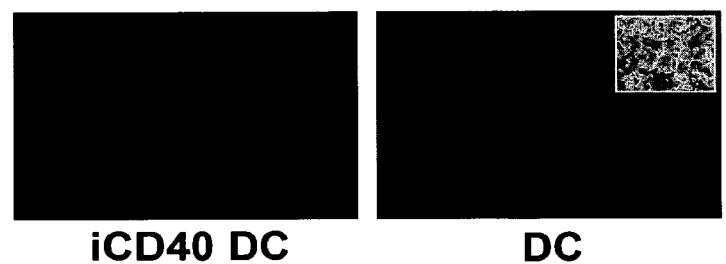

The physiological response of iCD40 was evaluated in the immature DC line, D2SC/1 (Lutz 1994), which maintains a stable phenotype over prolonged culture periods. The use of this DC line avoided confounding maturation effects that often occur spontaneously in primary DCs during typical culturing conditions. iCD40 was subcloned into a bicistronic vector co-expressing the Neo$^R$ gene and the resulting vector was electroporated into D2SC/1 cells. D2SC/1 DCs stably expressing the iCD40 transgene were selected in culture by G418, and clonal lines were derived by limiting dilution. Screening by probing for the HA-epitope tag allowed for high (Hi), intermediate (Int), and low (Lo) iCD40-expressing D2SC/1 DC clones (iCD40 DCs) to be selected for further analysis (FIG. 2A). Additional immunofluorescence experiments were performed to verify the membrane localization of iCD40 (FIG. 2B).

Figure 2C:
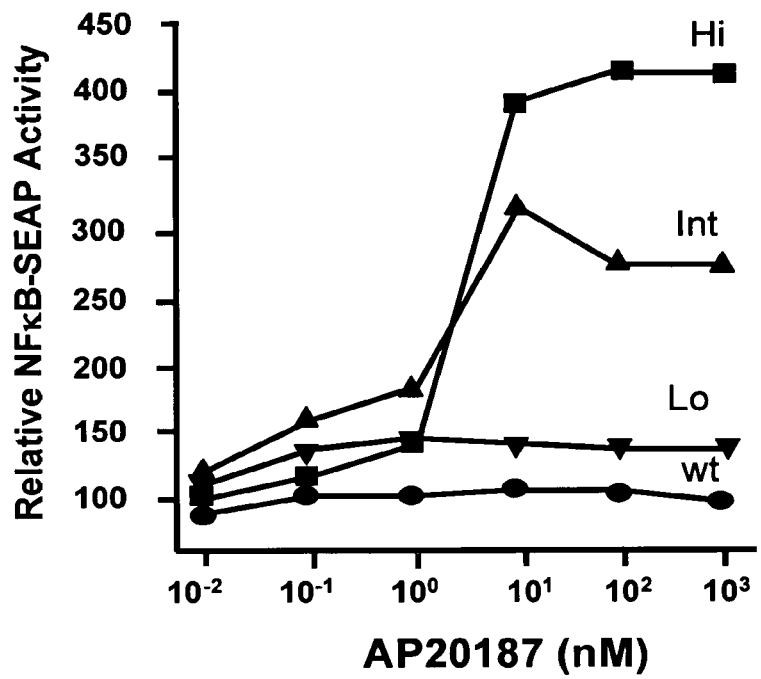
Figure 2D:
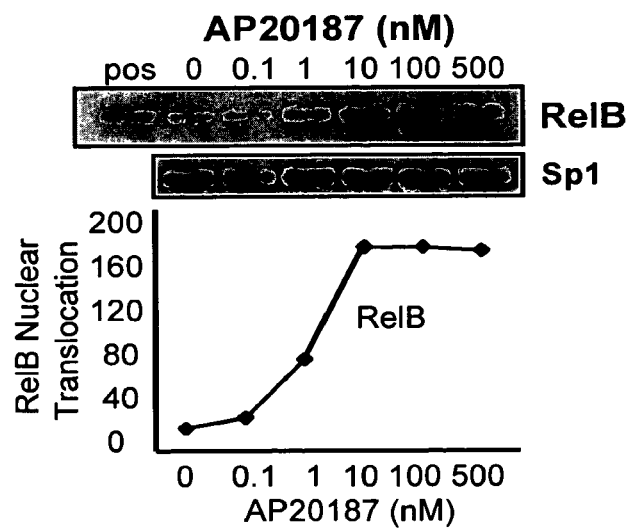

Reporter assays were carried out in these cell lines to determine whether iCD40 could also induce NFκB activation in DCs. Increasing AP20187 concentrations resulted in consistent elevation of NFκB activity that was further reflected in the levels of transgene expression by the respective DC lines (FIG. 2C). Several studies have identified that the RelB subunit of NFκB plays a significant role in the DC maturation program (Pettit 1997; Martin 2003). Indeed, nuclear localization of RelB correlated with the mature DC state and RelB$^{-/-}$ DCs exhibited a constitutively immature phenotype. Therefore, as a surrogate marker for DC activation, the nuclear translocation of RelB was analyzed by western blot in iCD40 DCs exposed to log dilutions of AP20187 (FIG. 2D). Additional results further confirmed that iCD40 triggered the nuclear translocation of DC-expressed RelB in a CID-dependent manner.

Figure 2E:
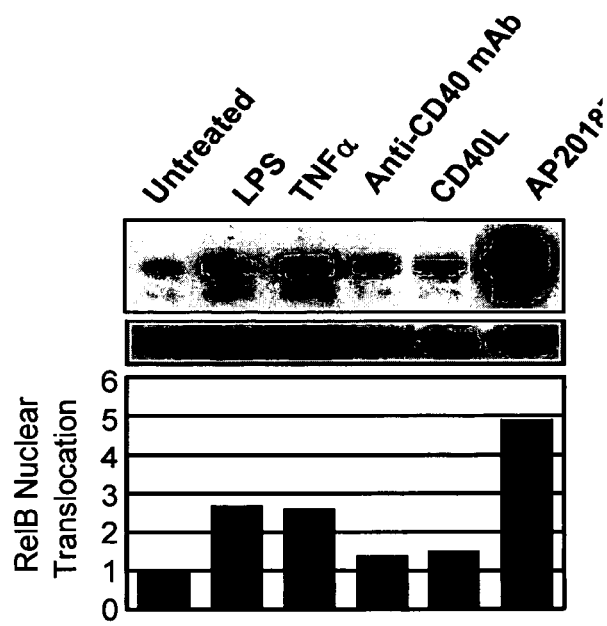
Figure 2F:
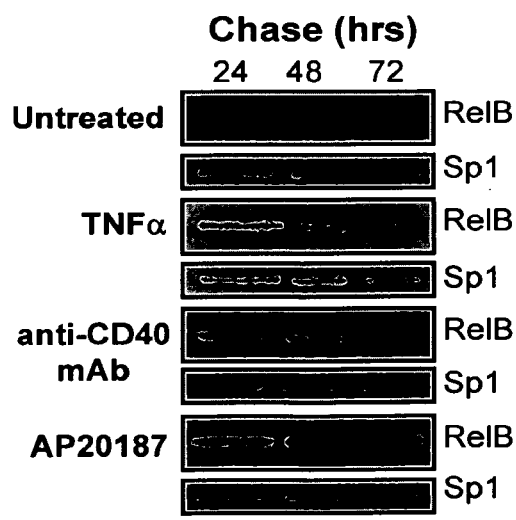

DC activation potency of iCD40 was compared with other traditional DC maturation stimuli, such as LPS, TNFα, anti-CD40 mAb, and CD40L. For the most informative comparison, each agent was titrated to determine the optimal concentration for RelB induction in iCD40 DCs and these concentrations were utilized to directly compare RelB activation by these different factors (FIG. 2E). The data clearly indicated that drug-dependent RelB induction in iCD40 DCs is superior to LPS, TNFα, anti-CD40 mAb, and CD40L. Pulse-chase experiments further revealed that the AP20187 dimerizer drug stimulated a more prolonged and durable RelB nuclear signal than TNFα or the anti-CD40 mAb (FIG. 2F). While TNFα-mediated RelB induction terminated after 24 hrs and anti-CD40 mAb induced RelB up to 48 hrs, the iCD40 receptor stimulated the RelB maturation pathway for at least 72 hrs in the presence of dimerizer drug. These results suggested that upon drug-mediated stimulation, iCD40 DCs are capable of maintaining a hyper-extended activation state.

EXAMPLE 11 iCD40 Induces DC Activation

Figure 3A:
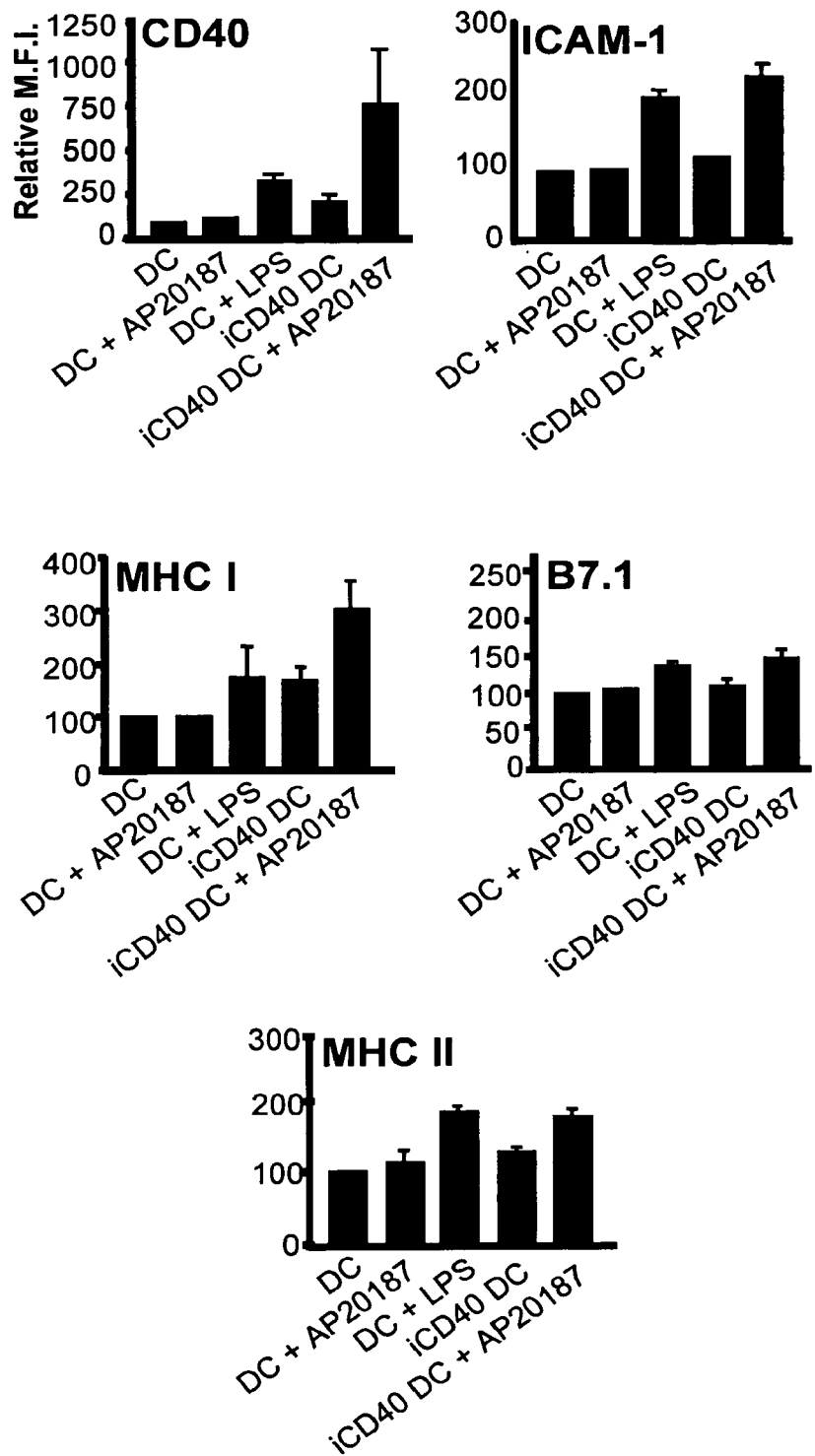
FIG. 3A-FIG. 3C show inducible CD40 triggers DC maturation and activation.

A component of the DC maturation program includes the upregulation of several surface molecules that participate in the process of T cell stimulation by direct involvement in antigen presentation and costimulation. Therefore, iCD40 DCs were treated with AP20187 and the surface expression of several of maturation markers, including, ICAM-1 (CD54), B7.1 (CD80), MHC class I K$^d$, MHC class II I-A$^d$ and endogenous CD40 (FIG. 3A) were analyzed by flow cytometry. Exposure of these DCs to CID resulted in significant elevations in the expression of each of these immunostimulatory proteins over untreated iCD40 DCs and the parental D2SC/1 line. This observed increase in the fluorescence intensity of these mature DC markers was comparable to that of LPS (from E. coli)-treated DCs. Only minimal basal signaling of the iCD40 receptor was detectable in untreated iCD40 DCs and drug treatment of the parental control D2SC/1 line had no observable effect. Moreover, when iCD40 DCs were pre-treated with an excess of a monomeric form of the drug, dimerizer drug-dependent upregulation of these surface markers was completely abolished, indicating that physical aggregation of the CD40 cytoplasmic domain was absolutely required for inducing the mature DC phenotype in the D2SC/1 line.

Figure 3B:
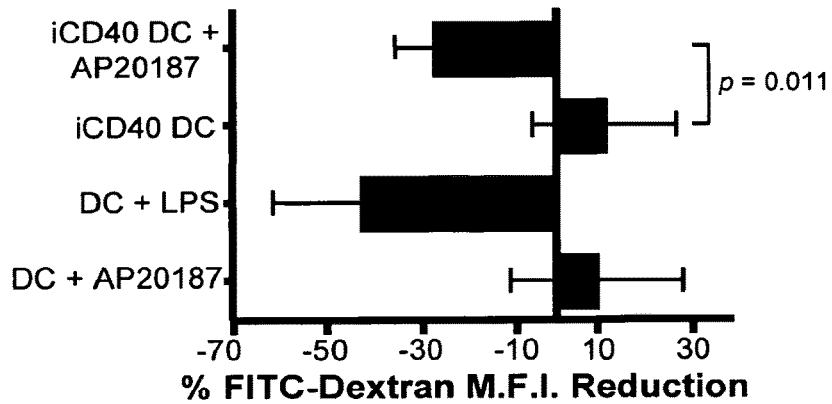

When DCs undergo maturation, they also exhibit functional alterations. These changes include a reduced capacity to uptake molecules from their microenvironment and a concomitant enhancement of their ability to stimulate T cell activation. Drug-induced modification of D2SC/1 DC receptor-mediated endocytosis was investigated by measuring the uptake of a FITC-tagged dextran molecule in iCD40 DCs and the parental D2SC/1 line. (FIG. 3B). CID-mediated activation of iCD40 DCs resulted in the reduced uptake of FITC-dextran to levels comparable to that of LPS-treated DCs at 37° C. Performing this same series of experiments at 0° C. resulted in minimal uptake of the FITC-dextran molecule, confirming that iCD40 activation is also capable of regulating the antigen uptake function of this DC line.

Figure 3C:
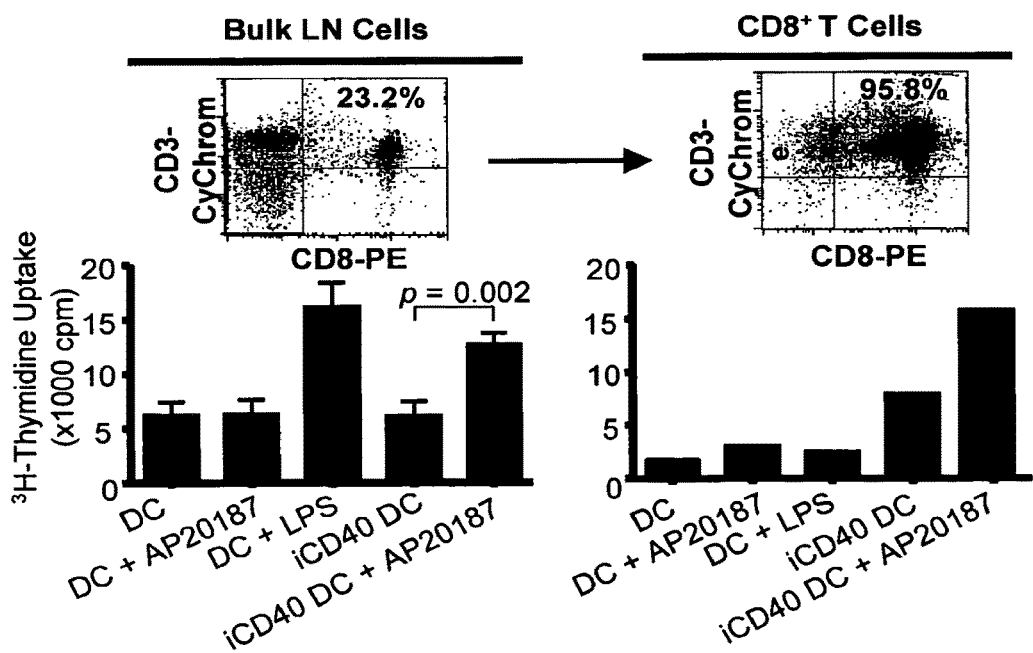

The initial approach to the determination of the T cell stimulation capacity of iCD40 DCs involved the co-incubation of mitomycin C-treated D2SC/1 DCs with syngeneic lymph node (LN)-derived cells in vitro. This mixed lymphocyte reaction (MLR) assay measured the ability of iCD40 DCs to induce a syngeneic T cell proliferative response to bovine serum-derived xenogeneic antigens (FIG. 3C). The results indicated that CID-treated iCD40 DCs were capable of inducing T cell proliferation to levels similar to that of LPS-treated DCs in vitro. In order to investigate whether this T cell activation effect was dependent on CD4+ T cell help, CD8+ T cells from LN tissue (>95%) were purified and the $^3$H-thymidine-based proliferation assay was repeated (FIG. 3C). The data showed that iCD40 DCs were capable of inducing CD8+ T cell proliferation in a CD4+-independent manner as opposed to LPS-treated DCs that failed to circumvent the requirement for CD4+ T cell-derived helper signals. These results demonstrated that iCD40-expressing DCs that have been pre-exposed to the dimerizer drug exhibited greater T cell stimulation capacity in vitro. Furthermore, the CD4+-depletion data inferred that the iCD40 receptor may be capable of substituting for CD4+ T cell help in DC-based vaccination strategies.

EXAMPLE 12

In vivo Drug-Mediated Activation of iCD40 DCs Following Vaccination

Figure 4A:
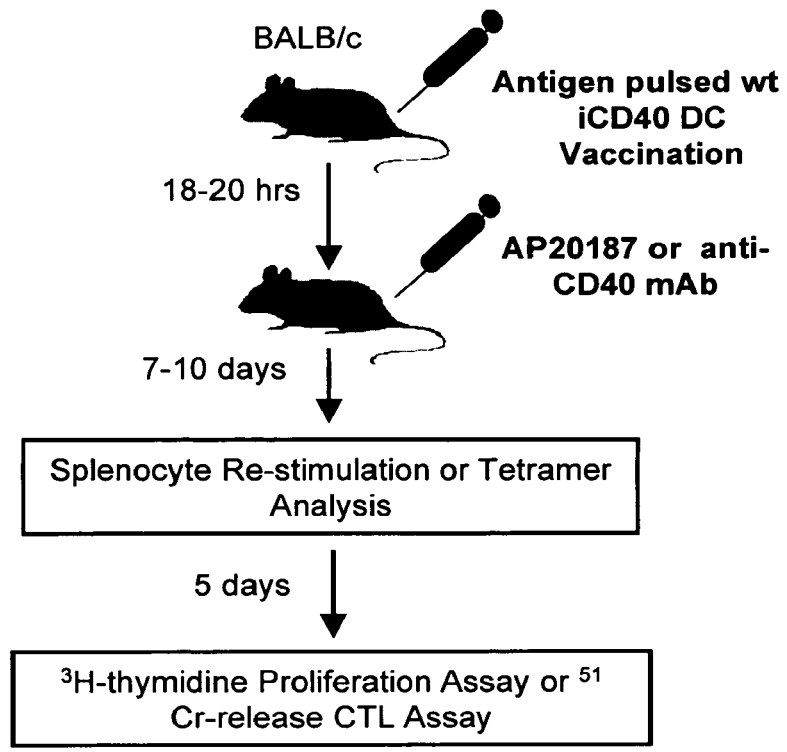
FIG. 4A-4E show in vivo drug-mediated activation of iCD40 DCs following vaccination induces an enhanced antigen-specific T cell response.
Figure 4B:
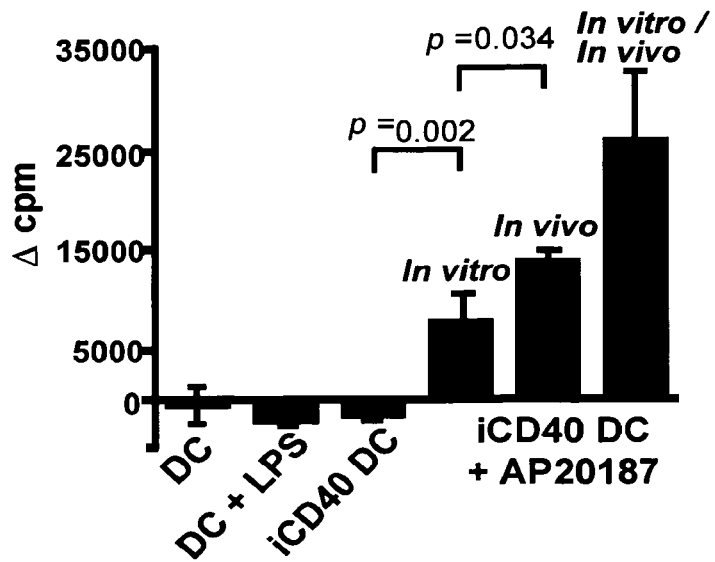
Figure 4C:
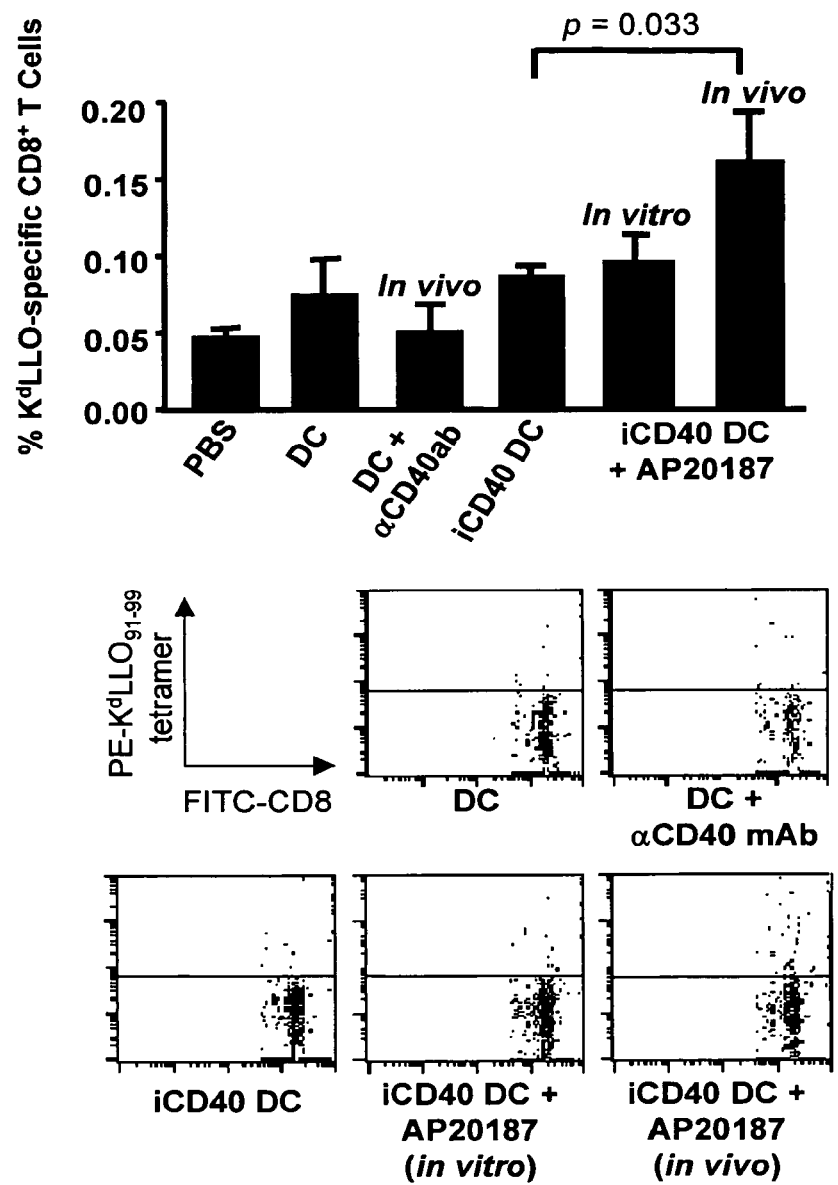

Since in vitro conditions may not necessarily mirror the more physiologically relevant conditions in vivo, the ability of iCD40 DCs to induce an antigen-specific T cell response in vivo following drug-mediated activation pre- or post-vaccine delivery was investigated. $1 \times 10^6$ parental and iCD40-expressing D2SC/1 DCs were pulsed with the H-2K$^d$-restricted peptide antigen, LLO$_{91-99}$, derived from the listeriolysin O protein of Listeria monocytogenes ±LPS, or AP20187, and injected intraperitoneally (i.p.) into syngeneic BALB/c mice. A subset of mice receiving LLO$_{91-99}$-pulsed DCs, were injected i.p. with either AP20187 or anti-CD40 mAb ~20 hours following the initial vaccination. Finally, splenocytes were harvested from LLO-primed mice 10 days later and co-cultured with mitomycin C-treated LLO$_{91-99}$-pulsed and non-pulsed DCs for an additional 5 days before being evaluated for the uptake of $^3$H-thymidine (FIG. 4A). The results indicated that in vivo activation of iCD40 DCs by AP20187 injection significantly enhanced the resulting T cell response relative to in vitro iCD40 activation prior to DC vaccine delivery (FIG. 4B). Furthermore, the combined pre- and post- activation of iCD40 DCs resulted in an additive T cell proliferative effect, suggesting that the in vitro activation of DCs did not confer adverse effects, such as attenuation of their migrational capacity. As opposed to the in vitro T cell proliferation assay discussed above, iCD40 stimulation of DCs in vivo resulted in a significantly more robust T cell response compared to LPS-treated DCs. Moreover, using an H-2K$^d$-LLO$_{91-99}$-specific tetramer, it was determined that a significant fraction of the responding T cell population was specific for the K$^d$-restricted peptide epitope originally used to load the DC-based vaccine (FIG. 4C,D).

Figure 4D:
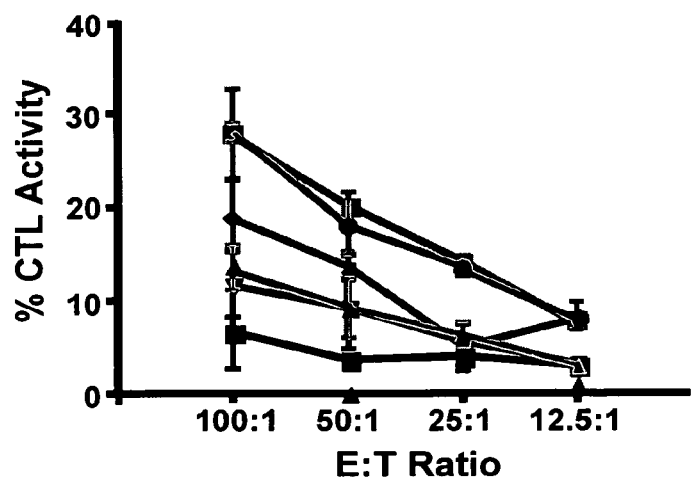
Figure 4E:
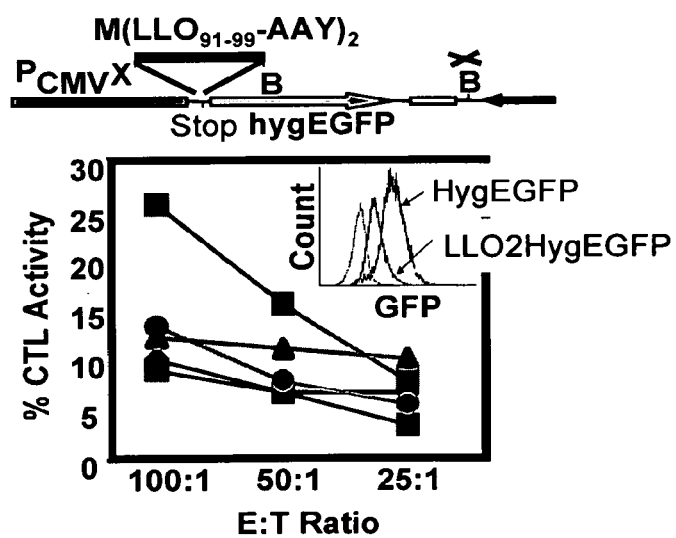

While tetramer analysis is a powerful aid in quantitating T cell populations, it does not reflect T cell effector function. In order to investigate the functionality of the T cells that respond to iCD40 DC antigen presentation, a P815-derived tumor cell line (P13.1), which ectopically expresses the β-galactosidase (βgal) protein as a surrogate tumor antigen, was utilized. After vaccinating BALB/c mice with βgal-loaded DCs and following the aforementioned culture protocol, a $^{51}$Cr-release cytotoxic T lymphocyte (CTL) assay was performed to assess the ability of the stimulated T cells to destroy βgal-expressing tumor cells. Consistent with the in vivo T cell proliferation data presented above, the delivery of AP20187 following DC administration resulted in improved tumor cell killing relative to non-activated or pre-activated DCs (FIG. 4D). To further study the CTL response to iCD40-expressing DCs, an LLO$_{91-99}$-expressing A20 lymphoma line was generated by cloning in-frame two tandem LLO$_{91-99}$ minigenes upstream of a HygGFP fusion protein. This strategy allowed for selection of LLO$_{91-99}$-expressing A20 tumor cells in culture with hygromycin and for tracking LLO$_{91-99}$ expression by flow cytometry analysis of enhanced green fluorescent protein (EGFP) (FIG. 4E). The LLO$_{91-99}$-expressing construct also included two adjacent AAY amino acid sequences after each minigene to improve proteosomal processing efficiency of MHC class I-restricted peptides. Despite flow cytometry profiles indicating that fusion of the LLO$_{91-99}$ peptide upstream of HygGFP destabilized the functionality of either the HygR gene or the fluorescence intensity of EGFP, the A20-LLO tumor line still exhibited greatly enhanced sensitivity to CTL-mediated killing following priming by LLO$_{91-99}$-loaded AP20187-exposed iCD40 DCs.

EXAMPLE 13 iCD40 Activates Primary Bone Marrow-Derived DCs

Figure 5A:
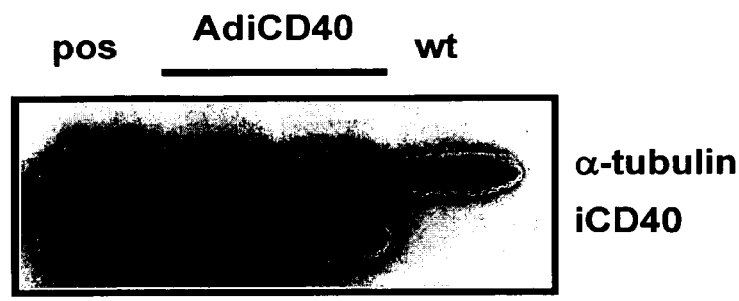
FIG. 5A-5E show iCD40 activates primary DCs and prolongs their longevity.
Figure 5B:
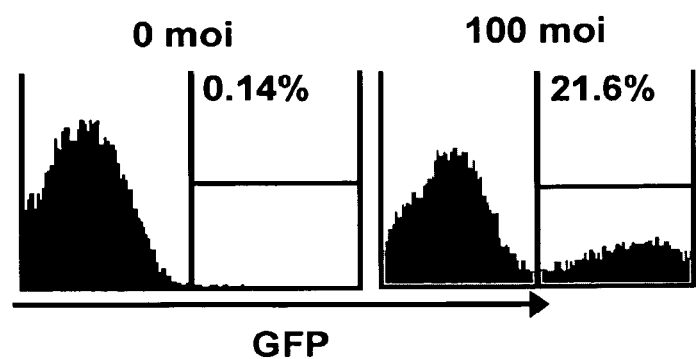
Figure 5C:
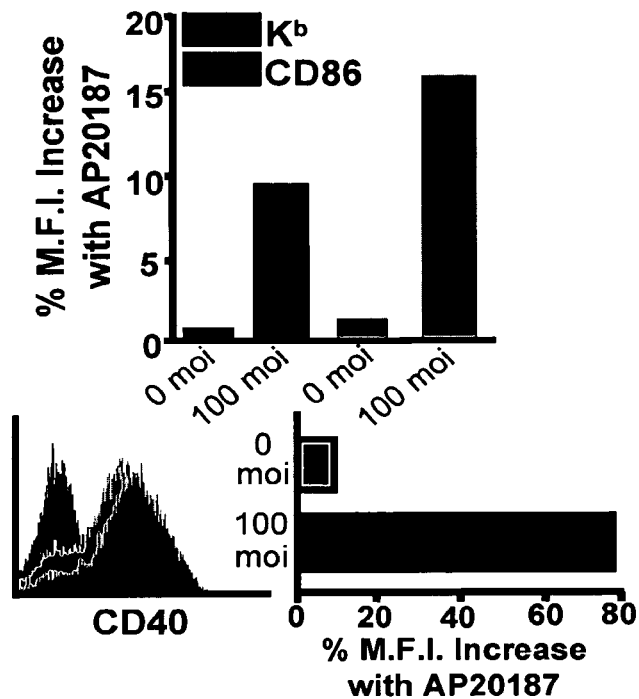
Figure 5D:
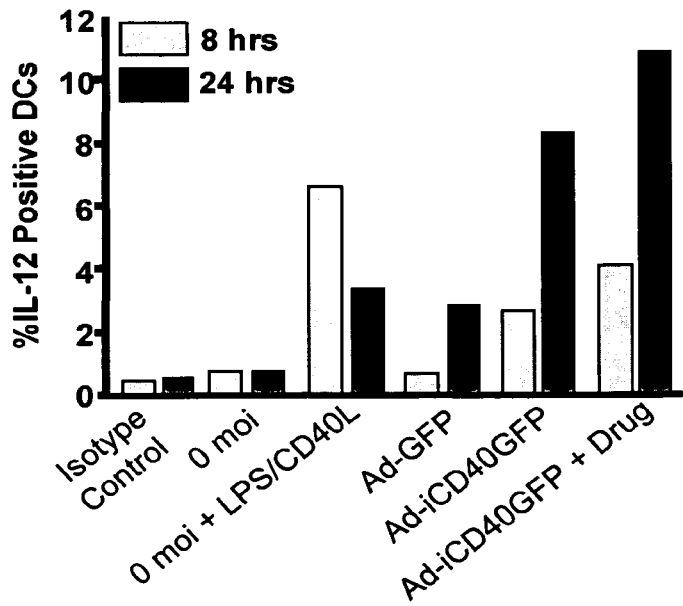

While D2SC/1 cells possess many characteristics of freshly isolated DCs, it was important to examine iCD40 functionality in primary bone marrow-derived DCs (BM-DCs) by utilizing an iCD40-expressing adenovirus. A viral region E1 and E3-deleted, replication-deficient type 5 adenoviral vector was engineered to express both iCD40 and EGFP under the control of the CMV early/immediate promoter/enhancer. Ad-iCD40-GFP successfully transduced and expressed the iCD40 transgene, as well as the EGFP marker, in purified BMDCs (FIG. 5A,B). Titrating Ad-iCD40-GFP while measuring iCD40-induced upregulation of B7.2 (CD86), showed that maximum drug-mediated iCD40 activation occurred at around 100 moi and proceeded asymptotically to plateau at higher viral titers. Although the effects were modest, AP20187 induced the surface expression of MHC class I K$^b$, B7.2, as well as endogenous CD40 on iCD40-expressing BMDCs at 100 moi but not on non-transduced DCs (FIG. 5C). The effects of Ad-iCD40-GFP on BMDCs were studied by using intracellular cytokine staining to evaluate DC expression of the TH1-polarizing cytokine, IL-12. The results confirmed numerous previous reports that an empty adenoviral vector can contribute to background fluorescence readings by stimulating the production of low levels of this cytokine (FIG. 5D) (Korst 2002). These data also revealed that the iCD40 transgene could generate a significant level of basal signaling at these titers even in the absence of CID. However, AP20187 exposure of these iCD40-expressing DCs managed to reproducibly overcome these cumulative effects to further increase the percentage of IL-12$^+$ DCs. Interestingly, the stimulation of IL-12p70/p40 synthesis with LPS and CD40L peaked at 8 hrs and decreased thereafter, while the percentage of IL-12+ DCs continued to increase until at least 24 hrs following adenoviral transduction. Previous work by Langenkamp et al. (Langenkamp 2000)has demonstrated that prolonged treatment of DCs with LPS exhausted their capacity for cytokine production. These results imply that iCD40, as opposed to the LPS danger signal, was capable of promoting and maintaining a more durable IL-12 response by BMDCs.

Figure 5E:
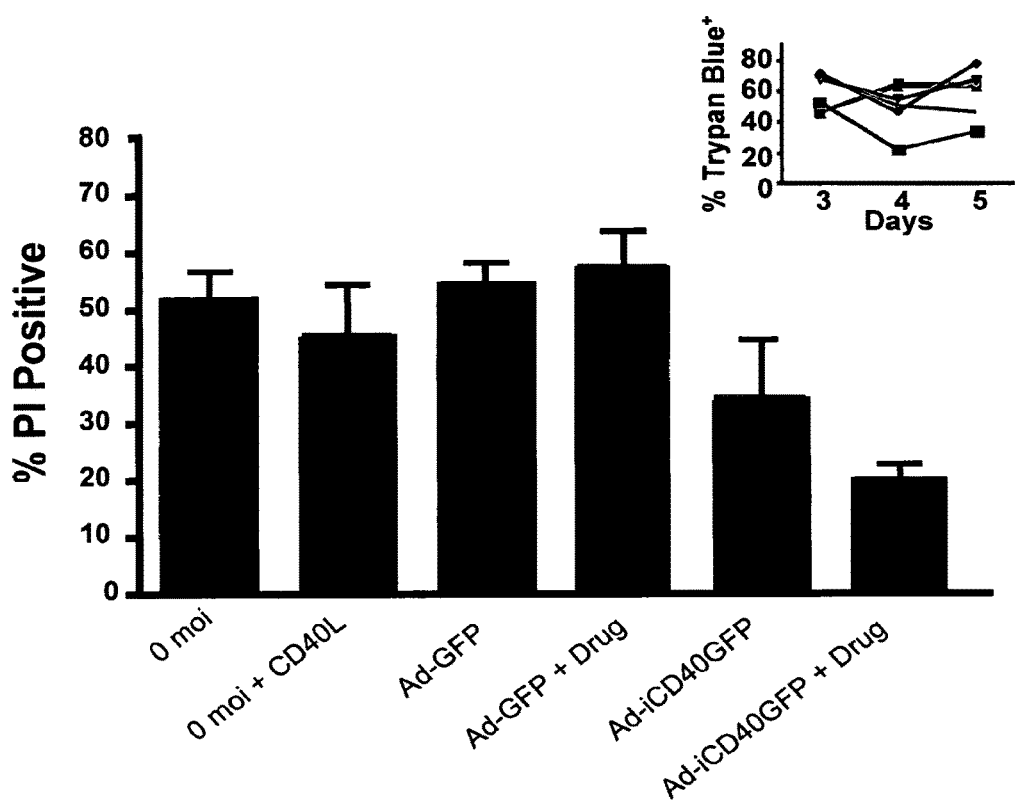

In addition to DC activation state, DC longevity is another critical variable that influences the generation of T cell-dependent immunity. In fact, CTL-mediated killing of DCs is considered to be a significant mechanism for modulating immune responses while protecting the host from autoimmune pathologies. Other work has established that CD40 stimulation of DCs prolongs their survival by a variety of mechanisms, including upregulation of the anti-apoptotic protein bcl-$X_L$ and the granzyme B inhibitor spi-6 (Medema 2001; Miga 2001). The effects of iCD40 relative to CD40L on DC survival were compared in an in vitro serum-starvation culture assay (FIG. 5E). By analyzing the membrane compromised propidium iodide (PI)-positive cell population by flow cytometry, it was determined that iCD40 expressing-BMDCs exhibited greater longevity under these conditions compared to non-transduced DCs treated with CD40L. This effect was iCD40-dependent since Ad-GFP-transduced DCs failed to reflect improved survival under these conditions. These results also showed that exposure of iCD40 BMDCs to the AP20187 dimerizer drug even further enhanced this survival effect relative to untreated BMDCs.

Despite the unintended maturation induced by the adenoviral vector and the enhanced basal signaling effects of iCD40 in primary BMDCs, enhanced DC activation in the presence of AP20187 was consistently detected. Overall, these data suggest that an inducible CD40 receptor designed to respond to a pharmacological agent was capable of maintaining primary DCs in a sustained state of activation compared to the more transient effects of CD40L stimulation. These data were consistent with earlier findings describing only short-term DC modulation for stimuli that target endogenous CD40.

EXAMPLE 14 iCD40 Activation Switch Functions as a Potent Adjuvant for DNA Vaccines

Figure 6A:
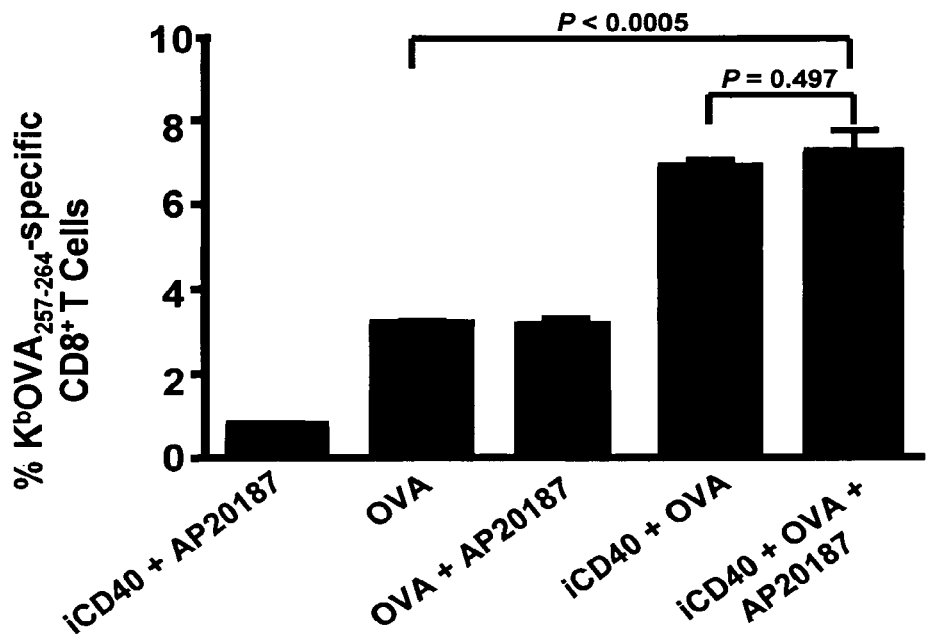
FIG. 6A-6B show iCD40 augments the immunogenicity of DNA vaccines in vivo.
Figure 6B:
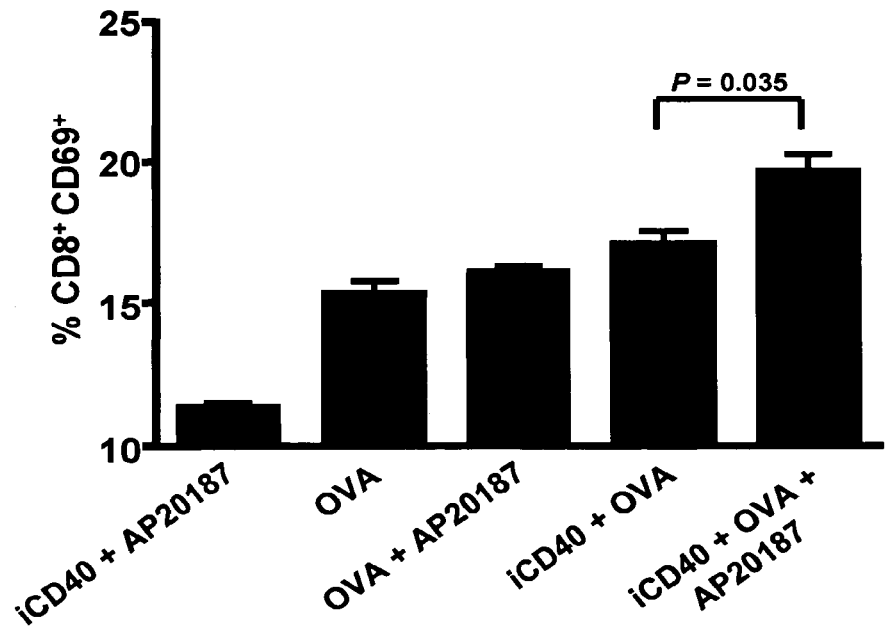
Figure 6C:
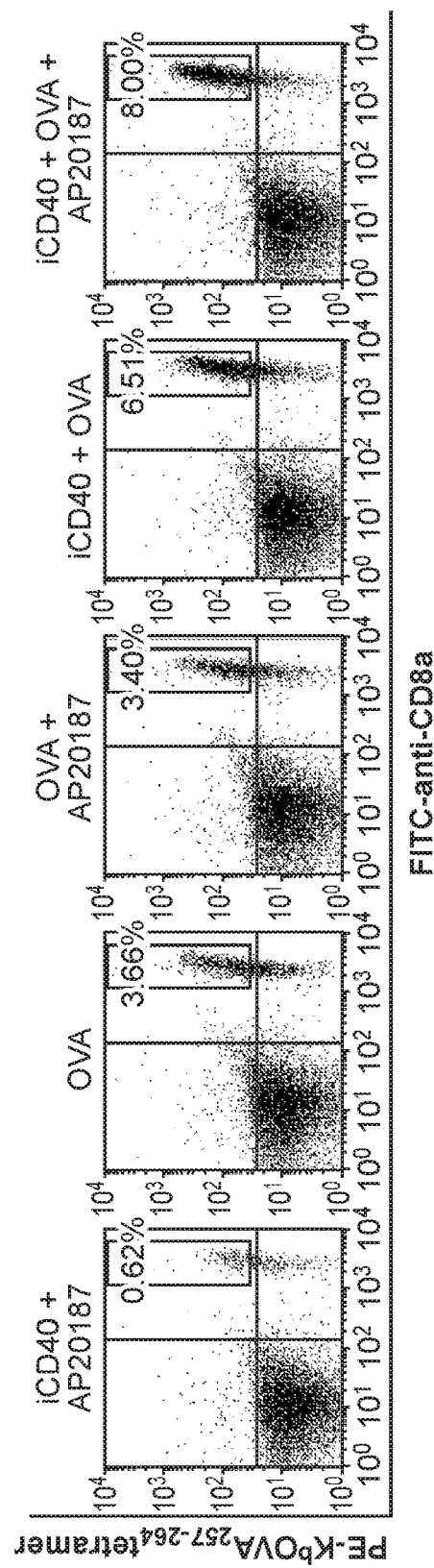

Previous studies have demonstrated that DCs play a critical role in the processing and presentation of DNA vaccines to responding T cells. Therefore, in order to examine the effects of iCD40 on primary DC functionality in vivo, the iCD40 activation switch was incorporated into a gene gun-dependent DNA vaccination protocol (Singh 2002). Gold micro-particles were coated with an OVA257-264 minigene plasmid in the presence and absence of a bicistronic vector co-expressing iCD40 with the hrGFP reporter. Biolistic transfection of C57BL/6 mice with the OVA257-264 minigene resulted in a ~3-fold enhancement in the percent of OVA257-264-specific CD8+ T cells, while the inclusion of the iCD40-expressing vector dramatically increased this same CD8+ T cell population by an additional ~2-fold (FIG. 6A,C). Although AP20187 did not further stimulate the expansion of OVA257-264-specific CD8+ T cells, i.p. administration of the dimerizer drug ~20 hours post-vaccination did enhance the percentage of activated CD69+ CD8+ T cells (FIG. 6B).

Figures 7A, 7B:
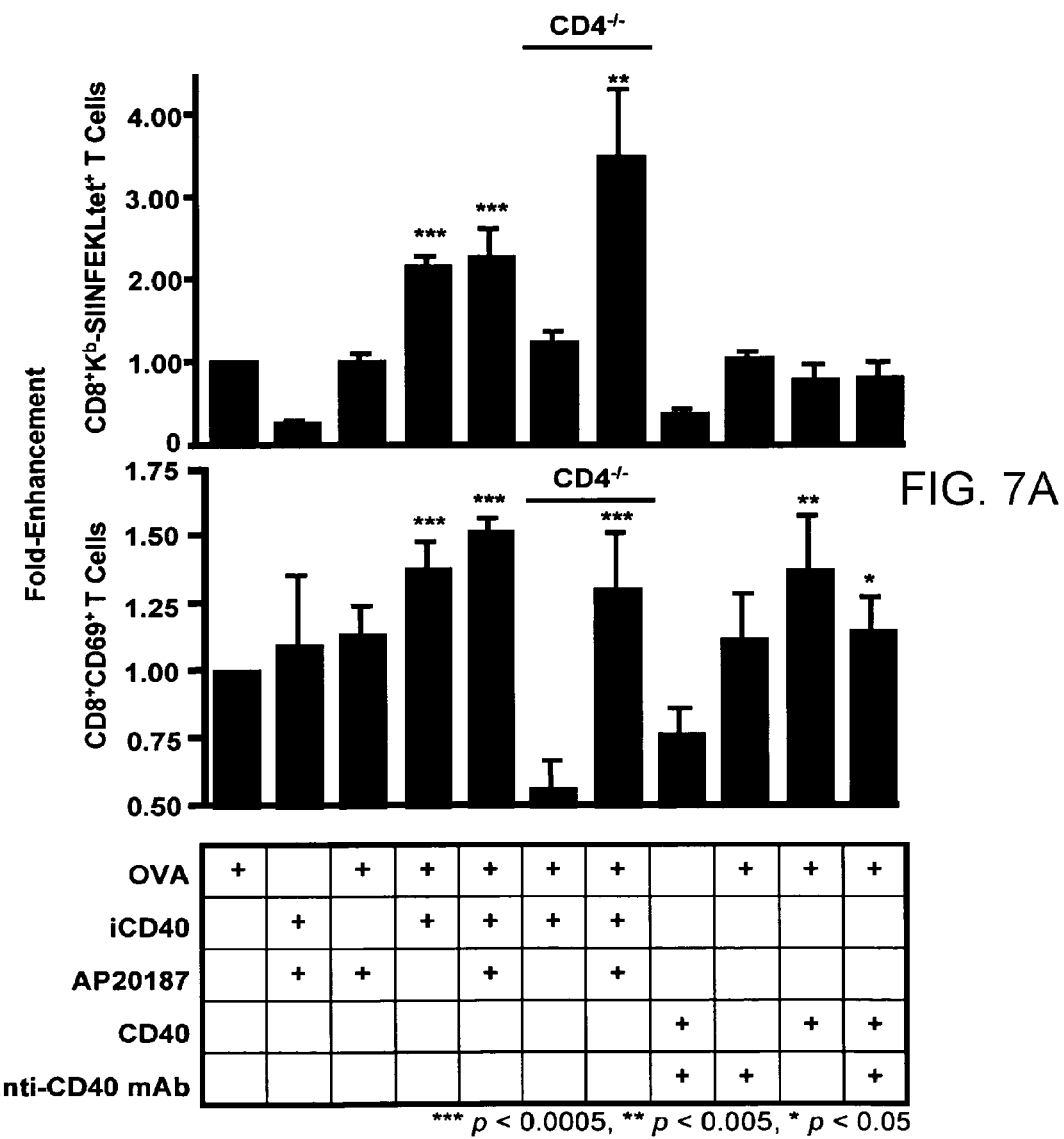
FIG. 7A-FIG. 7B show iCD40 enhancement of DNA vaccination.

In order to demonstrate the effectiveness of the iCD40 system in the absence of CD4+ T helper cells. Wildtype (C57BL/6) and CD4-knockout (T helper cell deficient) mice were vaccinated using the above Gene Gun DNA vaccination protocol. FIG. 7A shows that the enhancement of antigen-specific CD8+T cell population existed in mice ~14 days following vaccination. FIG. 7B shows the enhancement of activated (CD69+) CD8+ T cells ~14 days following vaccination. All the data was normalized to the antigen OVA alone. The data further demonstrated the enhanced potency of the drug-regulated iCD40 system relative to the full-length CD40 receptor and the agonistic anti-CD40 monoclonal antibody.

Thus, these results demonstrated the efficacy of the iCD40 activation switch in vivo, and showed that iCD40 can still upregulate CD8+ T cell responses in the absence of CD4+ T helper cells.

EXAMPLE 15

Insulated iCD40 Receptor is Resistant to Ligand-Induced Downregulation and to Negative Feedback Inhibition Mediated by the Type II CD40 Isoform The data presented above implies that the drug-regulated iCD40 receptor is capable of delivering a more potent stimulatory signal to DCs than the activation of endogenous CD40. It was determined that the underlying cause for this difference was based on the lack of an extracellular domain, making iCD40 resistant to both ligand-induced receptor downregulation and to interference by dominant negative receptors.

Figure 8A:
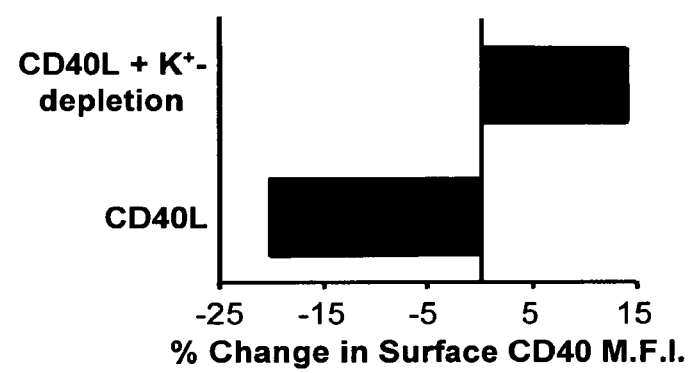
FIG. 8A-FIG. 8C show CD40L downregulates and reduces the signaling capacity of CD40.
Figure 8A:
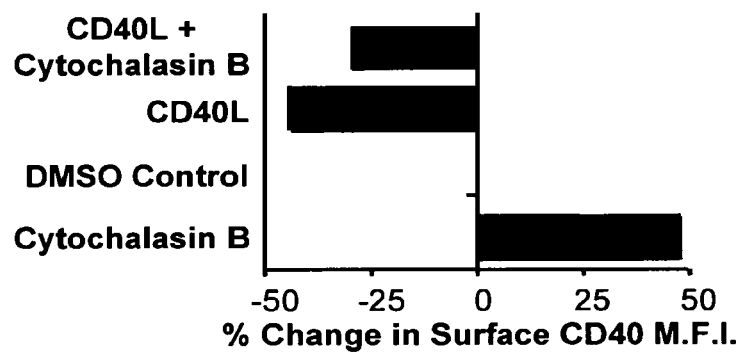
Figure 8B:
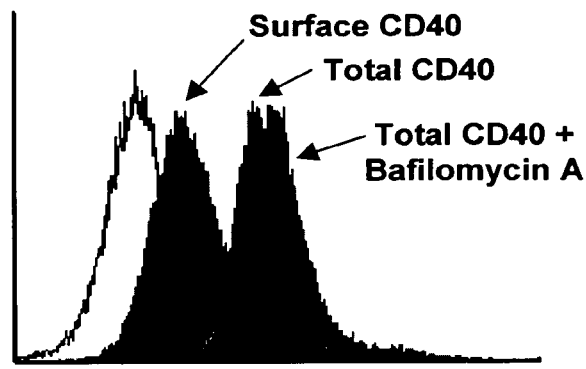
Figure 8C:
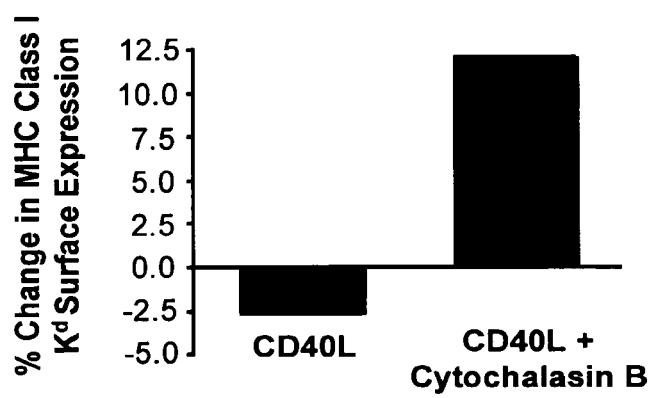

To initially investigate the potential downregulation of surface CD40 upon ligand engagement, flow cytometric analysis of DC surface expression of CD40 was monitored in the presence and absence of CD40L. Addition of CD40L promptly reduced the mean fluorescence intensity of CD40 on the D2SC/1 DC line with rapid kinetics. Inhibition studies showed this process was sensitive to both the endocytosis inhibitor, cytocholasin B, as well as to intracellar potassium-depletion, suggesting that the mechanisms of receptor-mediated endocytosis played a role in CD40 regulation (FIG. 8A). Furthermore, treatment of the D2SC/1 line with the endosomal $H^+$ATPase inhibitor balifomycin $A_1$ enhanced total CD40 levels based on intracellular staining assays. Overall, these results suggested that upon ligand engagement, CD40 was taken up by endocytosis and degraded by lysosomal proteolytic processing (FIG. 8B). Additional work indicates that the inhibition of CD40 endocytosis enhances its signaling capacity (FIG. 8C).

Figure 9A:
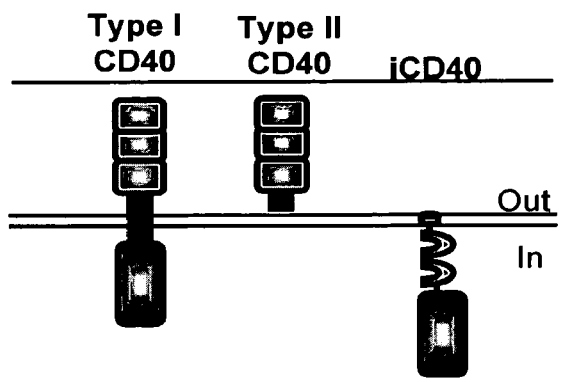
FIG. 9A-FIG. 9D show iCD40 circumvents negative feedback inhibition by the Type II CD40 (IICD40) isoform.
Figure 9B:
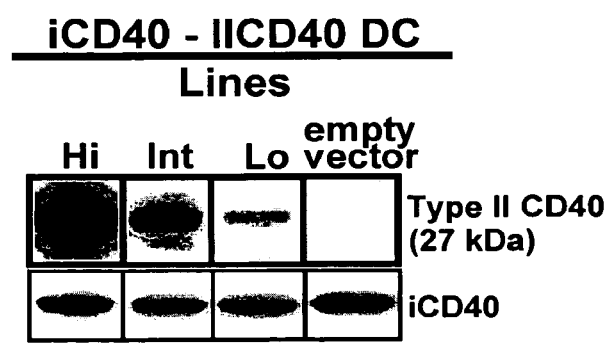
Figure 9C:
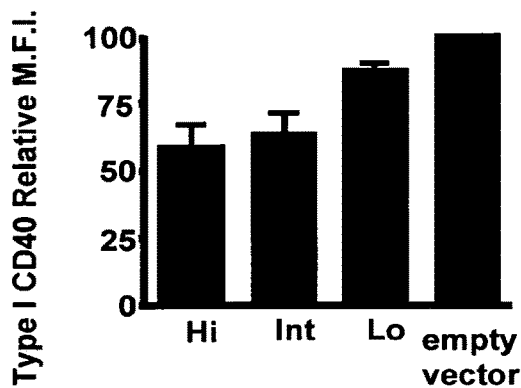

Expression of the truncated "type II" isoform of CD40, which lacks both a transmembrane and cytoplasmic domain, was upregulated in response to DC maturation (FIG. 9A). Previous work has shown that the type II CD40 isoform abrogated surface expression, as well as total cellular expression, of type I CD40 (Tone et al. 2001). It was hypothesized that this inhibitory mechanism involved homotypic interactions between the extracellular domains of the type I and II CD40 isoforms, however, no direct evidence was presented to provide further insight into this regulatory pathway. Therefore, it was posited that iCD40 would be resistant to type II CD40-mediated inhibition due to the absence of a ligand-binding ectodomain. To investigate the potential regulation of endogenous type I CD40 and iCD40 by this alternatively spliced gene product, the type II CD40 isoform was rt-PCR-amplified from purified bone marrow-derived murine DCs and sub-cloned into a ZeoR-expressing vector in-frame with the c-myc-derived epitope tag. This construct was used to generate clonal "double-stable" DCs that expressed both iCD40 and type II CD40 (IICD40) by selecting cell lines in G418 and zeocin-containing media. High (hi), intermediate (int), and low (lo) IICD40-expressing DC lines were selected by anti-myc western blot analysis for further study (FIG. 9B). An anti-HA blot of these same iCD40-IICD40 DC lines demonstrated that the total cellular expression of iCD40 was not affected by over-expression of the IICD40 transgene (FIG. 9B). However, flow cytometry analysis of type I CD40 surface expression demonstrated a reduction in the mean fluorescence intensity of this receptor in IICD40-expressing DC lines (FIG. 9C). Moreover, the predicted inverse relationship was found to exist between the expression level of type II CD40 and the expression of type I CD40. These data was consistent with that of previous work that demonstrated IICD40-mediated type I CD40 downregulation in a macrophage cell line.

Figure 9D:
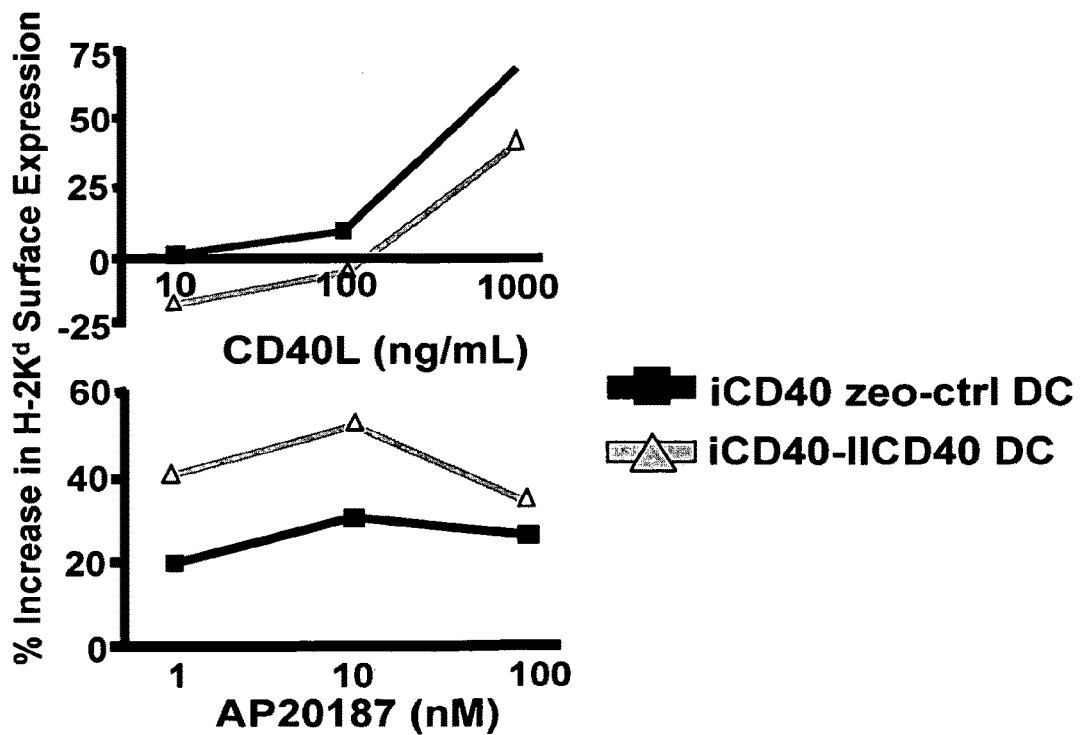

To expand upon these findings, the effects of CD40L and AP20187 titrations on each of the IICD40 lines were analyzed based on the hypothesis that IICD40-mediated type I CD40 downregulation should blunt the DC response to CD40L but not to AP20187 (FIG. 9D). Using MHC class I H-2K$^d$ surface expression as a reporter, the results revealed that IICD40 shifted the dose-response curve such that elevated amounts of CD40L were required to initiate signaling through the CD40 axis while, in contrast, AP20187 induced even higher levels of H-2K$^d$ than the empty vector control. Overall, these data confirmed the findings of Tone et al. and supported the notion that type I CD40-IICD40 interactions occurred via the homologous extracellular domains of these receptors. Furthermore, these results suggested that the iCD40 receptor switch was capable of circumventing negative feedback regulatory mechanisms involving dominant negative CD40 isoforms.

EXAMPLE 16

Generation of a CD11c Construct in Order to Generate a DC-Specific iCD40 Transgenic Mouse To generate a DC-specific iCD40-expressing transgenic mouse. iCD40 was subcloned into a vector containing the DC-specific CD11c promoter and purified by CsCl gradient ultracentrifugation. After sequencing, the vector was shown to induce the expression of iCD40 in 293T cells. DNA microinjections were performed in C57BL/6 mice.

Bone marrow-derived DCs were isolated from PCR-positive offspring for anti-HA western blots. Although iCD40 protein expression was found in all mice, the levels varied from barely detectable to easily detectable. These mice are currently being bred for functional experiments, but early results show pronounced expansion of splenic DCs in iCD40-expressing mice, with increased activation of T cells following CID administration.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Adema, G. J., et al., Nature, 1997, Jun. 12. 387: p. 713-7.
Amara, J. F., N. L. Hum Gene Ther, 1999, Nov. 1. 10: p. 2651-5.
Anderson, D. M., et al., Nature, 1997, Nov. 13. 390: p. 175-9.
Banchereau, J. a. S., R., Science, 1998, 392: 245-252.
Banchereau, J. and R. M. Steinman, Nature, 1998, Mar. 19. 392: p. 245-52.
Banchereau, J., et al., Annu Rev Immunol, 2000, 18: p. 767-811.
Bander, N. H., et al., Prostate, 1997, Dec. 1. 33: p. 233-9.
Bennett, S. R., et al., . Nature, 1998, Jun. 4. 393: p. 478-80.
Boczkowski, D., et al., J Exp Med, 1996. 184(2): p. 465-72.
Caux, C., et al., J Exp Med, 1994, Oct. 1. 180: p. 1263-72.
Chen et al PNAS 94: 1914-1918, 1997
Clackson, T., et al., Proc Natl Acad Sci USA, 1998. 95: p. 10437-10442.
Clarke, S. R., J Leukoc Biol, 2000, May 67: p. 607-14.
Cohen et al Nucleic Acid Res. 18:2807-2808, 1990
Farrar, M. A., Nature, 1996, Sep. 12. 383: p. 178-81.
Fearon et al. (1996) Science 272: 50-3.
Fernandez, N. C., et al., . Nat Med, 1999, Apr. 5: p. 405-11.
Gilboa, E., et al., Cancer Immunol Immunother, 1998, Apr. 46: p. 82-7.
Hermans, I., et al., Journal of Immunology, 2000, 164: 3095-3101.
Hollstein et al Nucleic Acids Res. 22:3551-3555, 1994
Inaba, K., et al., J Exp Med, 1992, Dec. 1. 176: p. 1693-702.
Israeli et al Cancer Res. 53:227-230, 1993
Jackson et al EMBOJ, 11:527-535, 1992
Janeway et al., (1989) Cold Spring Harb. Symp. Quant. Biol. 54: 1-13.
Kawakami et al Proc. Nat'l Acad. Sci. USA 91:6458-6462, 1992
Kawakami et al, J. Exp. Med. 180:347-352, 1994.
Korber et al, eds HIV Molecular Immunology Database, Los Alamos National Laboratory, Los Alamos, N. Mex. 1977
Korst, R., et al., Molecular Therapy, 2002, 5(3): 307-315.
Kugler, A., et al., Nat Med, 2000, Mar. 6: p. 332-6.
Kwon et al PNAS 84:7473-7477, 1987
Langenkamp, A., et al., Nature Immunology, 2000, 1(4): 311-316.
Lanzavecchia, A. and F. Sallusto, Science, 2000. 290: p. 92-96.
Lutz, M., et al., Journal of Immunological Methods, 1994, 174: 269-279.
Maldonado-Lopez, R., et al., J Exp Med, 1999, Feb. 1. 189: p. 587-92.
Martin, E., et al., Immunity, 2003, 18: 155-167.
McWhirter, S. M., et al., Proc Natl Acad Sci USA, 1999, Jul. 20. 96: p. 8408-13.
Medema, J., et al., Journal of Experimental Medicine, 2001, 194(5): 657-667.
Medzhitov et al. (1997) Curr. Opin. Immunol. 94: 4-9.
Miga, A., et al., European Journal of Immunology, 2001, 31: 959-965.
Morse, M. A., et al., Cancer Res, 1999, Jan. 1. 59: p. 56-8.
Nair, S. K., Gene Ther, 1998, Nov. 5: p. 1445-6.
Nair, S. K., D. Snyder, and E. Gilboa, J Immunol, 1996. 156(5): p. 1772-80.
Nair, S. K., et al., Eur J Immunol, 1997. 27(3): p. 589-97.
Ni, C., et al., PNAS, 2000, 97(19): 10395-10399.
Ni, C. Z., et al., Proc Natl Acad Sci USA, 2000, Sep. 12. 97: p. 10395-9.
Ohshima, Y., et al., J Immunol, 1997, Oct. 15. 159: p. 3838-48.
O'Sullivan, B. J. and R. Thomas, The Journal of Immunology, 2002, 168: 5491-5498.
Ouaaz, F., et al., Immunity, 2002, 16: 257-270.

Pettit, A., et al., Journal of Immunology, 1997, 159: 3681-3691.
Pirtskhalaishvili, G., et al., J Immunol, 2000, Aug. 15. 165: p. 1956-64.
Pound, C. R., et al., JAMA, 1999, May 5. 281: p. 1591-7.
Pound, C. R., et al., Urol Clin North Am, 1997, May. 24: p. 395-406.
Pulendran, B., et al., Proc Natl Acad Sci USA, 1999, Feb. 2. 96: p. 1036-41.
Pullen, S. S., et al., J Biol Chem, 1999, May 14. 274: p. 14246-54.
Putzer, B. M., et al., Proc Natl Acad Sci USA, 1997, Sep. 30. 94: p. 10889-94.
Ridge, J. P., D. R. F, and P. Nature, 1998, Jun. 4. 393: p. 474-8.
Rissoan, M. C., et al., Science, 1999, Feb. 19. 283: p. 1183-6.
Sallusto, F., et al., Eur J Immunol, 1998, Sep. 28: p. 2760-9.
Schoenberger, S. P., et al., Nature, 1998, Jun. 4. 393: p. 480-3.
Schuler, G. and R. M. J Exp Med, 1997, Oct. 20. 186: p. 1183-7.
Shariat, S. F., et al., Can. Res., 2001. 61(6).
Simons, J. W., et al., Cancer Res, 1999, Oct. 15. 59: p. 5160-8.
Slovin, S. F., et al., Semin Urol Oncol, 1998, Feb. 16: p. 53-9.
Spencer, D. M., et al., Curr Biol, 1996. 6(7): p. 839-47.
Spencer, D. M., et al., Science, 1993. 262: p. 1019-1024.
Steinman, R. a. P., M. Journal of Clinical Investigation, 2002, 109: 1519-1526.
Tamura, Y., et al., Science, 1997, Oct. 3. 278: p. 117-20.
Tang, H. L. and J. G. Cyster, Science, 1999, Apr. 30. 284: p. 819-22.
Tartour, E. and W. H. Fridman, Immunol Ltrs, 2000. 74: p. 1-3.
Termeer, C. C., et al., J Immunol, 2000, Aug. 15. 165: p. 1863-70.
Timmerman, J. M. and R. Levy, Annu Rev Med, 1999, 50: p. 507-29.
Tjoa, B. A. and G. P. Murphy, Immunol Ltrs, 2000. 74: p. 87-93.
Tone, M., et al., Proc Natl Acad Sci USA, 2001. 98(4): p. 1751-1756.
U.S. Pat. No. 4,514,506
U.S. Pat. No. 5,550,214
U.S. Pat. No. 5,648,226
U.S. Pat. No. 5,709,995
U.S. Pat. No. 5,719,054
U.S. Pat. No. 5,750,395
U.S. Pat. No. 5,780,036
U.S. Pat. No. 5,840,839
U.S. Pat. No. 5,869,608
U.S. Pat. No. 5,955,596
Ullrich, A. and J. Schlessinger, Cell, 1990. 61: p. 203-212.
Wong, P., Immunity, 2003, 188: 499-511.
Xie, X., et al., Hum Gene Ther, 2001. 12(5).
Zitvogel L, et al., J Exp Med 1996. 183:87-97.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An ex vivo nucleic acid comprising a polynucleotide promoter sequence operatively linked to a polynucleotide sequence encoding a chimeric protein comprising
   (a) a CD40 cytoplasmic polypeptide region lacking the CD40 extracellular domain, and
   (b) a ligand binding region comprising a FKBP12(V36) polypeptide.

2. The nucleic acid of claim 1, wherein the nucleic acid is isolated.

3. The nucleic acid of claim 1, wherein the ligand binding region comprises two or more FKBP12(V36) polypeptides.

4. The nucleic acid of claim 3, wherein the ligand binding region is amino terminal to the CD40 cytoplasmic polypeptide region of the chimeric protein.

5. The nucleic acid of claim 1, wherein the nucleic acid is contained within a vector.

6. The nucleic acid of claim 5, wherein the nucleic acid is contained within a viral vector.

7. The nucleic acid of claim 5, wherein the nucleic acid is contained within a plasmid vector.

8. An ex vivo antigen-presenting cell transduced or transfected with the nucleic acid of claim 5.

9. An ex vivo nucleic acid comprising a polynucleotide promoter sequence operatively linked to a polynucleotide sequence encoding a chimeric protein comprising
   (a) a CD40 cytoplasmic polypeptide region lacking the CD40 extracellular domain, and
   (b) an FK506 ligand binding polypeptide region that binds to AP1903 or AP20187.

10. The nucleic acid of claim 9, wherein the FK506 ligand binding region comprises two or more FK506 ligand binding polypeptides.

11. The nucleic acid of claim 9, wherein the nucleic acid is isolated.

12. The nucleic acid of claim 9, wherein the ligand binding polypeptide region is amino terminal to the CD40 cytoplasmic polypeptide region of the chimeric protein.

13. The nucleic acid of claim 9, wherein the nucleic acid is contained within a vector.

14. The nucleic acid of claim 13, wherein the nucleic acid is contained within a viral vector.

15. The nucleic acid of claim 13, wherein the nucleic acid is contained within a plasmid vector.

16. An ex vivo antigen-presenting cell transduced or transfected with the nucleic acid of claim 13.

* * * * *

SEQUENCE LISTING

```
<160> NUMBER OF SEQ ID NOS: 4

<210> SEQ ID NO 1
<211> LENGTH: 228
<212> TYPE: DNA
<213> ORGANISM: Mouse

<400> SEQUENCE: 1
tatatcaaaa aggtggtcaa gaaaccaaag gataatgaga tgttacccccc tgcggctcga      60 cggcaagatc cccaggagat ggaagattat cccggtcata acaccgctgc tccagtgcag     120
gagacactgc acgggtgtca gcctgtcaca caggaggatg gtaaagagag tcgcatctca     180
gtgcaggagc ggcaggtgac agacagcata gccttgaggc ccctggtc                  228

<210> SEQ ID NO 2
<211> LENGTH: 76
<212> TYPE: PRT
<213> ORGANISM: Mouse

<400> SEQUENCE: 2

Tyr Ile Lys Lys Val Val Lys Lys Pro Lys Asp Asn Glu Met Leu Pro
1               5                   10                  15

Pro Ala Ala Arg Arg Gln Asp Pro Gln Glu Met Glu Asp Tyr Pro Gly
            20                  25                  30
```

His Asn Thr Ala Ala Pro Val Gln Glu Thr Leu His Gly Cys Gln Pro
 35                  40                  45

Val Thr Gln Glu Asp Gly Lys Glu Ser Arg Ile Ser Val Gln Glu Arg
 50                  55                  60

Gln Val Thr Asp Ser Ile Ala Leu Arg Pro Leu Val
 65                  70                  75

<210> SEQ ID NO 3
<211> LENGTH: 1579
<212> TYPE: DNA
<213> ORGANISM: Mouse

<400> SEQUENCE: 3
tgccctgcat ggtgtctttg cctcggctgt gcgcgctatg ggctgcttg ttgacagcgg      60 tccatctagg gcagtgtgtt acgtgcagtg acaaacagta cctccacgat ggccagtgct    120
gtgatttgtg ccagccagga agccgactga caagccactg cacagctctt gagaagaccc    180
aatgccaccc atgtgactca ggcgaattct cagcccagtg aacagggag attcgctgtc     240 accagcacag acactgtgaa cccaatcaag ggcttcgggt taagaaggag ggcaccgcag    300
aatcagacac tgtctgtacc tgtaaggaag acaacactg caccagcaag gattgcgagg     360
catgtgctca gcacacgccc tgtatccctg ctttggagt tatggagatg ccactgaga      420 ccactgatac cgtctgtcat ccctgcccag tcggcttctt ctccaatcag tcatcacttt    480
tcgaaaagtg ttatccctgg acaagctgtg aggataagaa cttggaggtc ctacagaaag    540
gaacgagtca gactaatgtc atctgtggtt taaagtcccg gatgcgagcc ctgctggtca    600
ttcctgtcgt gatgggcatc ctcatcacca ttttcggggt gtttctctat atcaaaaagg    660
tggtcaagaa accaaaggat aatgagatgt accccctgc ggctcgacgg caagatcccc     720
aggagatgga agattatccc ggtcataaca ccgctgctcc agtgcaggag acactgcacg    780
ggtgtcagcc tgtcacacag gaggatggta agagagtcg catctcagtg caggagcggc    840
aggtgacaga cagcatagcc ttgaggcccc tggtctgaac cctggaactg ctttggaggc    900
gatggctgct tgctgacctt tgaagtttga gatgagccaa acagagccc agtgcagcta     960 actctcatgc ctgcccctg tcatttctca acttgctttt taaggatgga gggaaagctc    1020
gggcatcggg aggtccacag tgatatctac caagtgcagc agtgcaggac ccagagttgt    1080
cttgctgcgg cgttcactgt aaggagtcgt ggctacagga gtccgtggcc cgcagcttgt    1140
gctcgtagag ggcacctggt tgccatcagc agggtactgg ctaaataaat ctgtaattat    1200
ttatacaatg gcatctcaga aactctagca ggtggggcag aaaacaggta gtggaatgat    1260
gggtagagaa acagctttta aaacacattc caaggcaggt aagatggctt ttgtgggtaa    1320
aggagcttgc tgcccaaacc cggttacctg attttgatcc ctgggacttc atggtaaaag   1380
ggagagaacc aaatccagag ggttgtcatt tgacctccat gtgtgctctg tggtaatgta   1440
ccccgtgtgt gcacatgtgc acatatccta aaatggatgt ggtggtgtat tgtagaaatt   1500
atttaatccg ccctgggttt ctacctgtgt gttaccattt agttcttgaa taaagacaca   1560
ctcaaccttt atatttaca                                                1579

<210> SEQ ID NO 4
<211> LENGTH: 289
<212> TYPE: PRT
<213> ORGANISM: Mouse

```
<400> SEQUENCE: 4

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
                20                  25                  30

His Asp Gly Gln Cys Cys Asp Leu Cys Gln Pro Gly Ser Arg Leu Thr
            35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
                100                 105                 110

Ser Lys Asp Cys Glu Ala Cys Ala Gln His Thr Pro Cys Ile Pro Gly
            115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val Ile Pro Val Val Met Gly Ile Leu Ile Thr Ile
            195                 200                 205

Phe Gly Val Phe Leu Tyr Ile Lys Lys Val Val Lys Lys Pro Lys Asp
    210                 215                 220

Asn Glu Met Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln Val Thr Asp Ser Ile Ala Leu Arg Pro Leu
    275                 280                 285

Val
```